(12) United States Patent
Brousmiche et al.

(10) Patent No.: US 10,092,894 B2
(45) Date of Patent: Oct. 9, 2018

(54) CHROMATOGRAPHIC MATERIALS FOR THE SEPARATION OF UNSATURATED MOLECULES

(71) Applicant: Waters Technologies Corporation, Milford, MA (US)

(72) Inventors: Darryl W. Brousmiche, Grafton, MA (US); Jacob N. Fairchild, Upton, MA (US); Jason F. Hill, Milford, MA (US); Giorgis Isaac, Marlborough, MA (US); Michael F. Morris, Ashland, MA (US); Kevin D. Wyndham, Upton, MA (US)

(73) Assignee: Waters Technologies Corporation, Milford, MA (US)

( * ) Notice: Subject to any disclaimer, the term of this patent is extended or adjusted under 35 U.S.C. 154(b) by 387 days.

(21) Appl. No.: 14/194,686

(22) Filed: Mar. 1, 2014

(65) Prior Publication Data
US 2014/0319057 A1    Oct. 30, 2014

Related U.S. Application Data

(63) Continuation-in-part of application No. PCT/US2013/041221, filed on May 15, 2013, and a (Continued)

(51) Int. Cl.
*B01J 20/283* (2006.01)
*B01J 20/284* (2006.01)
(Continued)

(52) U.S. Cl.
CPC .......... *B01J 20/283* (2013.01); *B01D 15/26* (2013.01); *B01D 15/30* (2013.01); *B01D 15/305* (2013.01);
(Continued)

(58) Field of Classification Search
None
See application file for complete search history.

(56) References Cited

U.S. PATENT DOCUMENTS 4,017,528 A   4/1977  Unger et al.
4,415,631 A   11/1983  Schutijser
(Continued)

FOREIGN PATENT DOCUMENTS

WO   WO-2008/103423 A1   8/2008
WO   2010/061367 A2   6/2010
(Continued)

OTHER PUBLICATIONS

International Search Report and Written Opinion, International Application No. PCT/US2013/41221, International Filing Date May 13, 2013.
(Continued)

*Primary Examiner* — Kara Graber
(74) *Attorney, Agent, or Firm* — Deborah M. Vernon; Rebecca N. Barnes; Womble Bond Dickinson (US) LLP

(57) ABSTRACT

The present disclosure relates to a method of separating a compound of interest, particularly unsaturated compound(s) of interest, from a mixture. The compound is separated using a column having a chromatographic stationary phase material for various different modes of chromatography containing a first substituent and a second substituent. The first substituent minimizes compound retention variation over time under chromatographic conditions. The second substituent chromatographically and selectively retains the compound by incorporating one or more aromatic, polyaromatic, heterocyclic aromatic, or polyheterocyclic aromatic hydrocarbon groups, each group being optionally substituted with an aliphatic group.

8 Claims, 39 Drawing Sheets

Related U.S. Application Data continuation-in-part of application No. PCT/US2013/041207, filed on May 15, 2013.

(60) Provisional application No. 61/647,303, filed on May 15, 2012.

(51) Int. Cl.

| | |
|---|---|
| B01J 20/285 | (2006.01) |
| B01J 20/282 | (2006.01) |
| B01J 20/28 | (2006.01) |
| C07F 7/18 | (2006.01) |
| B01D 15/26 | (2006.01) |
| B01J 20/288 | (2006.01) |
| B01D 15/30 | (2006.01) |
| B01D 15/32 | (2006.01) |
| B01D 15/40 | (2006.01) |
| B01D 53/02 | (2006.01) |
| B01J 20/22 | (2006.01) |
| B01J 20/289 | (2006.01) |
| B01J 20/30 | (2006.01) |
| B01J 20/32 | (2006.01) |

(52) U.S. Cl.
CPC ......... *B01D 15/322* (2013.01); *B01D 15/40* (2013.01); *B01D 53/025* (2013.01); *B01J 20/22* (2013.01); *B01J 20/28004* (2013.01); *B01J 20/288* (2013.01); *B01J 20/289* (2013.01); *B01J 20/28016* (2013.01); *B01J 20/28042* (2013.01); *B01J 20/28057* (2013.01); *B01J 20/28059* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28073* (2013.01); *B01J 20/28076* (2013.01); *B01J 20/28078* (2013.01); *B01J 20/28083* (2013.01); *B01J 20/28085* (2013.01); *B01J 20/3085* (2013.01); *B01J 20/3204* (2013.01); *B01J 20/3246* (2013.01); *B01J 20/3285* (2013.01); *B01J 20/3293* (2013.01); *C07F 7/1836* (2013.01); *B01J 20/282* (2013.01); *B01J 20/284* (2013.01); *B01J 20/285* (2013.01); *B01J 20/32* (2013.01); *B01J 20/3206* (2013.01); *B01J 20/3208* (2013.01); *B01J 20/3234* (2013.01); *B01J 2220/54* (2013.01); *B01J 2220/80* (2013.01)

(56) References Cited

U.S. PATENT DOCUMENTS

| | | |
|---|---|---|
| 4,767,670 A | 8/1988 | Cox et al. |
| 4,835,058 A * | 5/1989 | Komiya .............. B01J 20/3204 210/198.2 |
| 5,374,755 A | 12/1994 | Neue et al. |
| 6,528,167 B2 | 3/2003 | O'Gara |
| 6,686,035 B2 | 2/2004 | Jiang et al. |
| 7,008,542 B2 | 3/2006 | Belew et al. |
| 7,125,488 B2 | 10/2006 | Li |
| 7,175,913 B2 | 2/2007 | O'Gara |
| 7,250,214 B2 | 7/2007 | Walter et al. |
| 2005/0242038 A1 | 11/2005 | Chen |
| 2006/0207923 A1 | 9/2006 | Li |
| 2007/0090052 A1 | 4/2007 | Broske et al. |
| 2007/0135304 A1 | 6/2007 | Walter et al. |
| 2007/0141325 A1 | 6/2007 | O'Gara et al. |
| 2007/0189944 A1 | 8/2007 | Kirkland et al. |
| 2007/0215547 A1 | 9/2007 | O'Gara |
| 2008/0203027 A1 | 8/2008 | Liu et al. |
| 2008/0223786 A1 | 9/2008 | Xu et al. |
| 2008/0293959 A1 | 11/2008 | Liu et al. |
| 2009/0127177 A1 | 5/2009 | Jiang et al. |
| 2009/0209722 A1 | 8/2009 | Jiang et al. |
| 2011/0049056 A1 | 3/2011 | Wyndham et al. |
| 2012/0055860 A1 | 3/2012 | Wyndham |
| 2012/0273404 A1 | 11/2012 | Wyndham et al. |
| 2013/0112605 A1 | 5/2013 | Wyndham et al. |

FOREIGN PATENT DOCUMENTS

| | | |
|---|---|---|
| WO | WO-2011017418 A1 | 2/2011 |
| WO | WO-2013/173494 A1 | 11/2013 |

OTHER PUBLICATIONS

International Search Report and Written Opinion, Internatioanl Application No. PCT/US2013/41207, International Filing Date May 15, 2013.

Chen et al., "Factors that Influence the Cutaneous Synthesis and Dietary Sournces of Vitamin D", Archives of Biochemistry and Biophysics, 2007, vol. 460, pp. 213-217.

Dermody et al., "Interactions Between Organized, Surface-Confined Monolayers and Vapor-Phase Probe Molecules. 11. Synthesis, Characteriztion, and Chemical Sensitivity of Self-Assembled Polydiacetylene/Calix[n]arene Bilayers", J.Am. Chem. Soc, 1996, vol. 118, pp. 11912-11917.

Fang et al., "Surface-Directed DNA Condensation in the Absence of Soluble Multivalent Cations", Nucleic Acids Reseaerch, 1998, vol. 26, No. 2, pp. 588-593.

Gao et al., "Immobilization of Pyrene via Diethylenetriamine on Quartz Plate Surace for Recognition of Dicarboxylic Acids". Applied Surface Science , 2006. vol. 252, pp. 3884-3893.

Kall et al., "Determination of Total Vitamin B6 in Foods by Isocratic HPLC: a Comparions with Microbiological Analysis", Food Chemistry, 82, 2003, pp. 315-327.

Lei et al., "Synthesis of Polymer-Supported Anthracene and Its Application s a Dienophile Scavenger", Organic Letters, 2004, vol. 6, No. 5, pp. 795-798.

Ollevier et al., "Bismuth Triflate-Catalyzed Mild and Efficient Epoxide Opening by Aromatic Amines Under Aqueous Conditions", Tetrahedron Letters, 2004, vol. 45, pp. 49-52.

International Search Report for International Application PCT/US15/17972; International Application Filing Date: Feb. 27, 2015.

Written Opinion from the International Bureau dated Jun. 8, 2015 for International Application No. PCT/US15/17972.

* cited by examiner

32 Lipid Species in GLC85 Standard

Position (isomeric) of double bonds

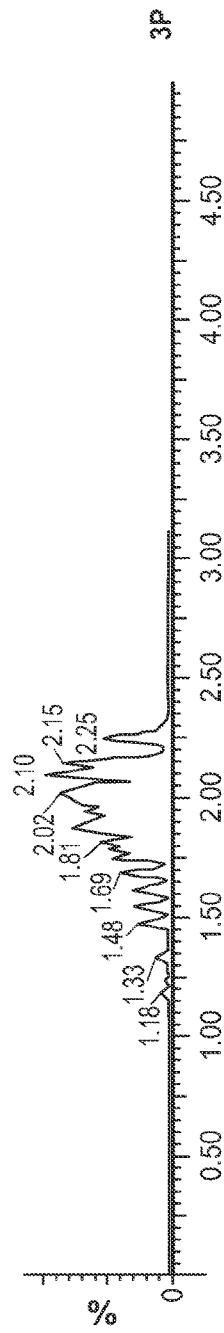
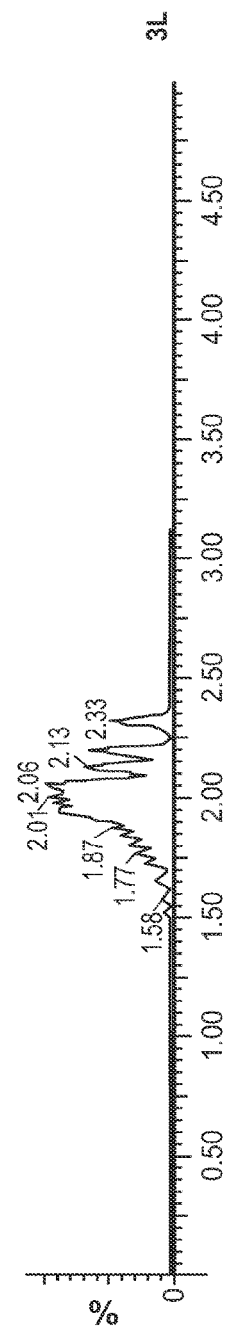
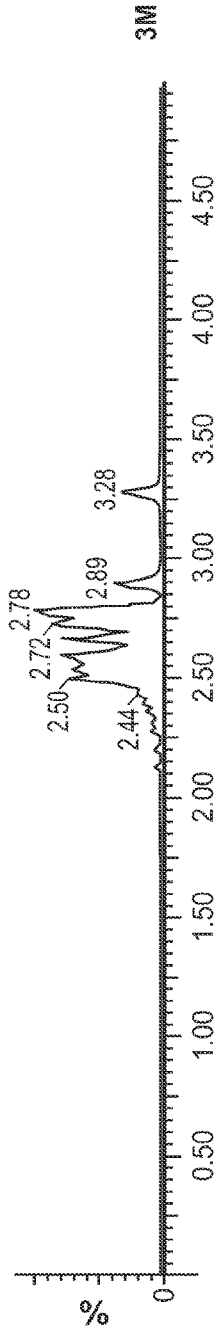
FIG. 17A Lipids Profile with Various Materials
FIG. 17B
FIG. 17C

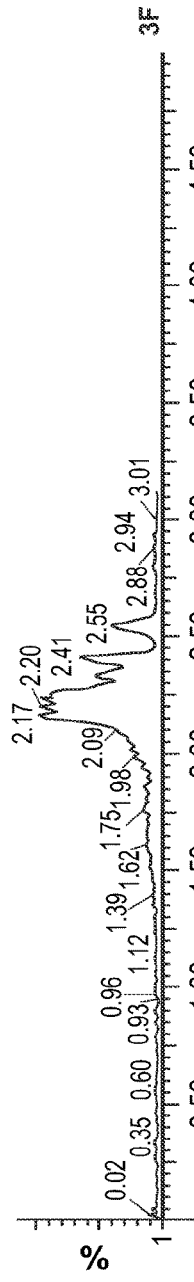
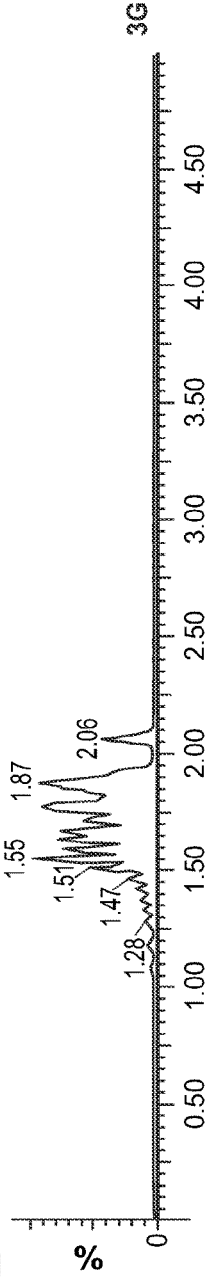
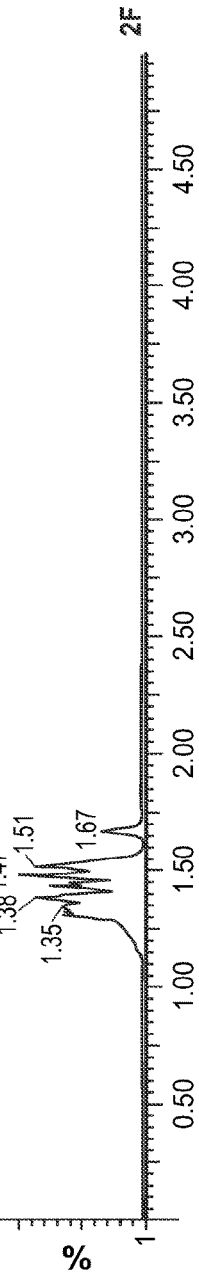
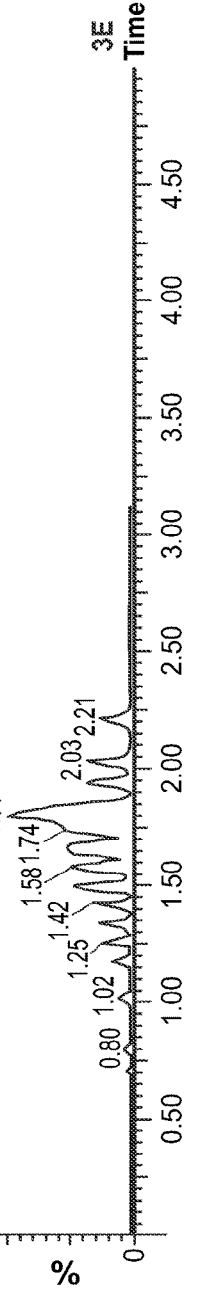
FIG. 17D
FIG. 17E
FIG. 17F
FIG. 17G

Using Material 3A

Using Material 3L

Using Material 3M

Using Material 3F

Using Material 3G

Using Material 2F

Using Material 3E

CHROMATOGRAPHIC MATERIALS FOR THE SEPARATION OF UNSATURATED MOLECULES

CROSS REFERENCE TO RELATED APPLICATIONS

This application is a continuation-in-part of International Patent Application Nos. PCT/US2013/041211, filed May 15, 2013, and PCT/US2013/041207, filed May 15, 2013, which claim priority to Provisional Application No. 61/647,303, filed May 15, 2012, each application of which is incorporated herein by reference in its entirety.

FIELD OF THE INVENTION

The present disclosure relates generally to chromatographic materials for the separation of unsaturated molecules. The present disclosure relates more particularly, in various embodiments, to chromatographic materials for normal phase chromatography, high-pressure liquid chromatography, solvated gas chromatography, supercritical fluid chromatography, sub-critical fluid chromatography, carbon dioxide based chromatography, hydrophilic interaction liquid chromatography and hydrophobic interaction liquid chromatography that mitigate or avoid retention drift or change while exhibiting useful overall retention for the separation of unsaturated molecules, as well as corresponding apparatuses, kits, methods of manufacture, and methods of use.

BACKGROUND OF THE INVENTION

Chromatography is the collective term for a set of laboratory techniques for the separation of mixtures. The mixture is dissolved in a mobile phase, which carries it through a stationary phase. The various constituents of the mixture travel at different speeds, causing them to separate. The separation is based on differential partitioning between the mobile and stationary phases. Subtle differences in a compound's partition coefficient result in differential retention on the stationary phase, thus changing the separation. Chromatography is useful for the separation of compounds that are structurally related, such as regio-isomers, chiral, diastereomers, etc. Some techniques, including SFC, are known for being particularly useful for separating structurally related vitamins, natural products and chemical materials. Often, however, chromatographic techniques are insufficient to separate all structurally related compounds. For example, critical pairs of related vitamins (e.g., D2 and D3, K1 and K2) are difficult to separate/resolve.

Packing materials for fluid or liquid chromatography can be generally classified into two types: organic materials (e.g., polydivinylbenzene) and inorganic materials (e.g., silica). Many organic materials are chemically stable against strongly alkaline and strongly acidic mobile phases, allowing flexibility in the choice of mobile phase composition and pH. However, organic chromatographic materials can result in columns with low efficiency, particularly with low molecular-weight analytes. Many organic chromatographic materials not only lack the mechanical strength of typical chromatographic silica and also shrink and swell when the composition of the mobile phase is changed.

Silica is widely used in High Performance Liquid Chromatography (HPLC), Ultra High Performance Liquid Chromatography (UHPLC), and Supercritical Fluid Chromatography (SFC). Some applications employ silica that has been surface-derivatized with an organic functional group such as octadecyl (C18), octyl (C8), phenyl, amino, cyano, and the like. As stationary phases for HPLC, these packing materials can result in columns that have high efficiency and do not show evidence of shrinking or swelling.

Hybrid materials can provide solutions to certain chromatographic problems experienced with silica based packing materials. Hybrid materials can provide improvements including improved high and low pH stability, mechanical stability, peak shape when used at pH 7, efficiency, retentivity, and desirable chromatographic selectivity.

However, potential problems can exist for conventional hybrid materials and silica materials in other applications. One problem is poor peak shape for bases when used at low pH, which can negatively impact loadability and peak capacity when used at low pH. Another problem is a change in acidic and basic analyte retention times (denoted 'drift') after a column is exposed to repeated changes in mobile phase pH (e.g., switching repeatedly from pH 10 to 3).

Another problem is retention drift or change, for example in chromatography modes with little water (e.g., less than 5%, less than 1%). For example, retention drift or change is observed under standard SFC conditions for both silica and organic-inorganic hybrid (e.g., BEH Technology™ materials available from Waters Technologies Corporation, Milford Mass.) based chromatographic phases, bonded and unbonded. Other SFC stationary phases can also exhibit similar retention drift or change.

SUMMARY OF THE INVENTION

In various aspects and embodiments, the present disclosure provides chromatographic materials for normal phase chromatography, high-pressure liquid chromatography, solvated gas chromatography, supercritical fluid chromatography, sub-critical fluid chromatography, carbon dioxide based chromatography, hydrophilic interaction liquid chromatography and hydrophobic interaction liquid chromatography that mitigate or avoid retention drift or change while exhibiting useful overall retention for the separation of unsaturated molecules, as well as corresponding apparatuses, kits, methods of manufacture, and methods of use.

The present disclosure includes various additional advantages, including but not limited to, the ability to selection/design selectivity through selection/design of the chemical modifications.

In one embodiment, the present disclosure relates to a method of separating a compound of interest from a mixture, the method comprising providing a mixture containing the compound of interest, introducing a portion of the mixture to a chromatographic system having a chromatographic column, and eluting the separated compound of interest from the column, wherein the column has a stationary phase having the following structure (i):

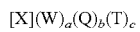

$$[X](W)_a(Q)_b(T)_c \qquad (i)$$

wherein X is a chromatographic substrate containing silica, metal oxide, an inorganic-organic hybrid material, a group of block copolymers, or combinations thereof, W is selected from the group consisting of hydrogen and hydroxyl, wherein W is bound to the surface of X, Q is a first substituent which minimizes analyte retention variation over time under chromatographic conditions having low water concentrations, T is a second substituent which chromatographically retains the analyte, wherein T has one or more aromatic, polyaromatic, heterocyclic aromatic, or polyheterocyclic aromatic hydrocarbon groups, each group being optionally substituted with an aliphatic group; and b and c are positive numbers, 0.05≤(b/c)≤100, and a≥0.

In some embodiments, Q has the following structure (ii):

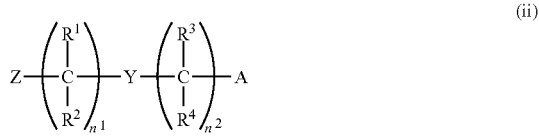

wherein n1 is an integer from 1-30, n2 is an integer from 1-30, $R^1$, $R^2$, $R^3$ and $R^4$ are each independently selected from the group consisting of hydrogen, hydroxyl, fluoro, methyl, ethyl, n-propyl, iso-propyl, n-butyl, iso-butyl, tert-butyl, lower alkyl, a protected or deprotected alcohol, and a zwitterion, Z is either (a) a surface attachment group having the formula $(B^1)_x(R^5)_y(R^6)_z$Si—, wherein x is an integer from 1-3, y is an integer from 0-2, z is an integer from 0-2, and x+y+z=3, $R^5$ and $R^6$ are each independently selected from the group consisting of methyl, ethyl, n-propyl, iso-propyl, n-butyl, iso-butyl, tert-butyl, substituted or unsubstituted aryl, cyclic alkyl, branched alkyl, lower alkyl, a protected or deprotected alcohol, a zwitterion group and a siloxane bond, and $B^1$ is a siloxane bond, or (b) an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage, or (c) an adsorbed, surface group that is not covalently attached to the surface of the material, Y is an embedded polar functionality, a bond or an aliphatic group, and A is selected from the group consisting of an hydrophilic terminal group, a functionizable group, hydrogen, hydroxyl, fluoro, methyl, ethyl, n-propyl, iso-propyl, n-butyl, iso-butyl, tert-butyl, a lower alkyl and a polarizable group.

In some embodiments, T has the following structure (iii):

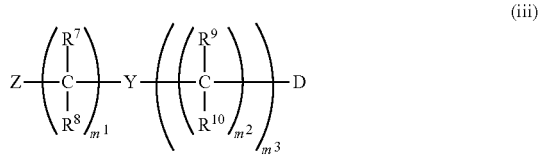

wherein $m^1$ is an integer from 1-30, $m^2$ is an integer from 1-30, $m^3$ is an integer from 1-3, $R^7$, $R^8$, $R^9$ and $R^{10}$ are each independently selected from the group consisting of hydrogen, hydroxyl, fluoro, methyl, ethyl, n-propyl, iso-propyl, n-butyl, iso-butyl, tert-butyl, lower alkyl, a protected or deprotected alcohol, a zwitterion, an aromatic hydrocarbon group and a hetercyclic aromatic hydrocarbon group, Z is (a) a surface attachment group having the formula $(B^1)_x(R^5)_y(R^6)_z$Si—, wherein x is an integer from 1-3, y is an integer from 0-2, z is an integer from 0-2, and x+y+z=3, $R^5$ and $R^6$ are each independently selected from the group consisting of methyl, ethyl, n-propyl, iso-propyl, n-butyl, iso-butyl, tert-butyl, substituted or unsubstituted aryl, cyclic alkyl, branched alkyl, lower alkyl, a protected or deprotected alcohol, a zwitterion group and a siloxane bond, and $B^1$ is a siloxane bond, (b) an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage, or (c) an adsorbed, surface group that is not covalently attached to the surface of the material, Y is an embedded polar functionality, a bond or an aliphatic group, D is selected from the group consisting of a bond, N, O, S, —$(CH_2)_{0-12}$—N—$R^{11}R^{12}$, —$(CH_2)_{0-12}$—O—$R^{11}$, —$(CH_2)_{0-12}$—S—$R^{11}$, —$(CH_2)_{0-12}$—N—$(CH_2)_{0-12}$—$R^{11}R^{12}$, —$(CH_2)_{0-12}$—O—$(CH_2)_{0-12}$—$R^{11}$, —$(CH_2)_{0-12}$—S—$(CH_2)_{0-12}$—$R^{11}$, —$(CH_2)_{0-12}$—S(O)$_{1-2}$—$(CH_2)_{0-12}$—N—$R^{11}R^{12}$, —$(CH_2)_{0-12}$—S(O)$_{1-2}$—$(CH_2)_{0-12}$—O—$R^{11}$, —$(CH_2)_{0-12}$—S(O)$_{1-2}$—$(CH_2)_{0-12}$—S—$R^{11}$, —$(CH_2)_{0-12}$—S(O)$_{1-2}$—$(CH_2)_{0-12}$—N—$(CH_2)_{0-12}$—$R^{11}R^{12}$, —$(CH_2)_{0-12}$—S(O)$_{1-2}$—$(CH_2)_{0-12}$—O—$(CH_2)_{0-12}$—$R^{11}$, —$(CH_2)_{0-12}$—S(O)$_{1-2}$—$(CH_2)_{0-12}$—S—$(CH_2)_{0-12}$—$R^{11}$, $R^{11}$ is a first mono-aromatic, polyaromatic, heterocyclic aromatic, or polyheterocyclic aromatic group, $R^{12}$ is a hydrogen, an aliphatic group or a second mono-aromatic, polyaromatic, heterocyclic aromatic, or polyheterocyclic aromatic group, wherein $R^{11}$ and $R^{12}$ are optionally substituted with an aliphatic group. Various fractions of Q, T, or both can be polymerized.

In another embodiment, the present disclosure relates to method for separating a lipid, vitamin or polycyclic aromatic hydrocarbon from a mixture.

In another embodiment, the present disclosure relates to a chromatographic stationary phase having the following structure (i):

$$[X](W)_a(Q)_b(T)_c \quad\quad (i)$$

wherein X is a chromatographic substrate containing silica, metal oxide, an inorganic-organic hybrid material, a group of block copolymers, or combinations thereof, W is selected from the group consisting of hydrogen and hydroxyl, wherein W is bound to the surface of X, Q is a first substituent which minimizes analyte retention variation over time under chromatographic conditions having low water concentrations, T is a second substituent which chromatographically retains the analyte, wherein T has one or more mono-aromatic, polyaromatic, heterocyclic aromatic, or polyheterocyclic aromatic groups, each group being optionally substituted with an aliphatic group; and b and c are positive numbers, 0.05≤(b/c)≤100, and a≥0.

In another embodiment, the present disclosure relates to a column, capillary column, monolithic column, microfluidic device or apparatus for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography comprising a housing having at least one wall defining a chamber having an entrance and an exit, and a stationary phase having the above structure, i.e. (i), disposed therein, wherein the housing and stationary phase are adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography.

In another embodiment, the present disclosure relates to a kit for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography comprising a housing having at least one wall defining a chamber having an entrance and an exit, and a stationary phase having the above structure, i.e. (i), disposed therein, wherein the housing and stationary phase are adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography; and instructions for performing normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography with the housing and stationary phase.

In another embodiment, the present disclosure relates to a method for preparing a stationary phase having the above structure, i.e. (i), comprising reacting a chromatographic substrate with a silane coupling agent having a pendant reactive group, reacting a second chemical agent comprising one or more aromatic, polyaromatic, heterocyclic aromatic, or polyheterocyclic aromatic hydrocarbon groups with the pendant reactive group; and neutralize any remaining unreacted pendant reactive groups, thereby producing the stationary phase.

In another embodiment, the present disclosure relates to a method for preparing a stationary phase having the above structure, i.e. (i), comprising oligomerizing a silane coupling agent having a pendant reactive group, reacting a core surface with the oligomerized silane coupling agent, reacting a second chemical agent comprising one or more aromatic, polyaromatic, heterocyclic aromatic, or polyheterocyclic aromatic hydrocarbon groups with the pendant reactive group; and neutralize any remaining unreacted pendant reactive groups, thereby producing the stationary phase.

In another embodiment, the present disclosure relates to a method for mitigating or preventing retention drift in normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography comprising chromatographically separating a sample using a chromatographic device comprising a chromatographic stationary phase having the above structure, i.e. (i), disposed therein, thereby mitigating or preventing retention drift.

The present disclosure advantageously mitigates or avoids retention drift or change while exhibiting useful overall retention, particularly for unsaturated molecules or compounds of interest. For example, in SFC, retention drift or change can be (among various other theories) attributed to alkoxylation of solvent accessible silanols on the particle under the standard $CO_2$/MeOH mobile phase (and/or by other alcohol co-solvents) utilized for SFC. This is a problem, as users observe a change in the chromatography (e.g., retention time) obtained on their SFC system as the column ages, and again when a new, non-alkoxylated column is put on the system.

In various aspects and embodiments, the present disclosure provides various solutions to such retention drift or change and related problems (e.g., retention, peak shape, and the like) through selection and/or modification of the chromatographic material. For example, the invention includes specialized functionalization of a chromatographic core surface (e.g., with particular functional groups, and combinations thereof), which essentially prevent chromatographic interaction between and analyte and the chromatographic core surface, which maintaining desired interaction between the analyte and the chromatographic material.

In other various aspects and embodiments, the present disclosure relates to chromatographic materials having greatly reduced secondary interactions with the base particle surface (e.g., unwanted interactions, non-specific adsorption). Secondary interactions of analyte with the material surface can occur due to silanols, pendant hydrophobic groups and polymer or hybrid backbone chains.

In various aspects and embodiments, the present disclosure provides numerous advantages. For example, the present disclosure can provide for a stationary phase capable of resolving analytes across all classes (e.g., acidic, basic and neutral), particularly unsaturated analytes, with superior retention, peak capacity and peak shape, peak shape for bases being of lesser importance. In various examples, the present disclosure can effectively masks silanols from the analytes of interest producing a predictable and stable chromatographic separation. In various examples, the present disclosure can effectively eliminate retention drift or change due to unwanted support surface interactions with analyte. The present disclosure can be especially effective at masking silanols on silica or silica hybrid materials. In various examples, the present disclosure can improve peak capacity and tailing across all analyte classes, but especially with bases. In various examples, the present disclosure can avoid pore clogging, despite bonding with oligomeric siloxanes (e.g., as compared to conventional polymeric coatings of porous silica materials, which can result in clogging of the pores greatly decreasing the available surface area of the materials and leading to inhomogeneous surfaces—despite the promotion of oligomerization of silanes in the present disclosure there is no evidence of pore clogging or decreased surface area).

The present disclosure provides advantages over the prior art based on its unique chemistry and performance properties. For example, the liquid separations of unsaturated compounds usually involves separations performed on C18 bonded phases, such as ACQUITY UPC²® HSS C18 SB. On that material, alkyl chains are the retention selectors resulting in high methylene/hydrophobic selectivity, but little shape/isomeric selectivity. The present disclosure provides retention selectors capable of both methylene/hydrophobic selectivity and shape/isomeric selectivity. For example, stationary phases of the present disclosure are exceptional at retaining and separating fat-soluble vitamins, lipids and metabolites as well as providing enhanced shape/isomeric selectivity as compared to C18 bonded phases.

The present disclosure is described in further detail by the drawings and examples below, which are used only for illustration purposes and are not limiting.

BRIEF DESCRIPTION OF THE DRAWINGS

The present disclosure can be more readily understood in the context of the following drawings and Detailed Description. It will be understood by a practitioner of ordinary skill in the art that the following drawings are not necessarily to scale, emphasis instead being placed on illustrating the inventive concepts of the present invention.

FIG. 17A shows a chromatogram of various lipids using a 1-aminoanthracene based stationary phase as described in Examples 3 and 10.

FIG. 17B shows a chromatogram of various lipids using a 2-picolylamine based stationary phase as described in Examples 3 and 10.

FIG. 17C shows a chromatogram of various lipids using a pyridine based stationary phase as described in Examples 3 and 10.

FIG. 17D shows a chromatogram of various lipids using a 6-aminoquinoline based stationary phase as described in Examples 3 and 10.

FIG. 17E shows a chromatogram of various lipids using an aniline based stationary phase as described in Examples 3 and 10.

FIG. 17F shows a chromatogram of various lipids using a GPTMS based stationary phase as described in Examples 3 and 10.

FIG. 17G shows a chromatogram of various lipids using a 4-n-octylaniline based stationary phase as described in Examples 3 and 10.

DETAILED DESCRIPTION OF THE INVENTION

Figure 1B:
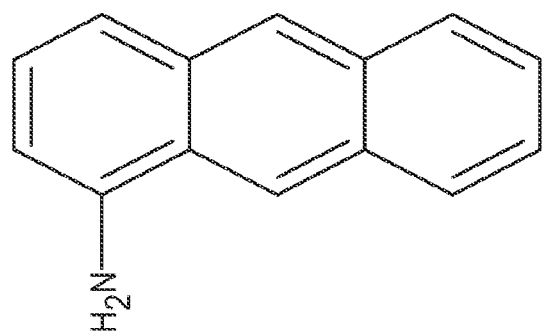
FIGS. 1A and 1B shows the structure of glycidoxypropyltrimethoxysilane (GPTMS) (FIG. 1A) and 1-aminoanthracene (FIG. 1B).

In various aspects and embodiments, the present disclosure provides chromatographic materials for normal phase chromatography, high-pressure liquid chromatography, solvated gas chromatography, supercritical fluid chromatography, sub-critical fluid chromatography, carbon dioxide based chromatography, hydrophilic interaction liquid chromatography and hydrophobic interaction liquid chromatography that mitigate or avoid retention drift or change while exhibiting useful overall retention for the separation of unsaturated molecules, as well as corresponding apparatuses, kits, methods of manufacture, and methods of use. In some embodiments, the present disclosure also provides retention and separation of structurally related compounds, such as critical pairs which are difficult to separate.

The present disclosure advantageously mitigates or avoids retention drift or change while exhibiting useful overall retention. For example, in SFC, retention drift or change can be (among various other theories) attributed to alkoxylation of solvent accessible silanols on the particle under the standard $CO_2$/MeOH mobile phase (and/or by other alcohol co-solvents) utilized for SFC. This is a problem, as users observe a change in the chromatography (e.g., retention time) obtained on their SFC system as the column ages, and again when a new, non-alkoxylated column is put on the system.

In various aspects and embodiments, the present disclosure provides various solutions to such retention drift or change and related problems (e.g., retention, peak shape, and the like) through selective modification of chromatographic materials and/or resolution of mixtures of unsaturated compounds of interest.

Definitions

In various aspects and embodiments, the present invention provides for mitigating or preventing retention drift or change. "Retention drift" or "retention change" can include an undesired difference in elution time between chromatographic runs or experiments (e.g., in run 1, peak x elutes at time y, but in run 1+n, peak x elutes at time z). Thus, retention drift or change can result in undesired effects including experimental noise, irreproducibility, or failure. Accordingly, in a broad sense, mitigating or preventing retention drift or change includes addressing or counteracting an undesired difference in elution times between chromatographic runs, to the extent that the chromatographic experiment provides and chromatographically acceptable result.

In some embodiments, mitigating or preventing retention drift or change is not constant an absolute or constant value. For example, the amount of retention drift or change the can occur while still achieving a chromatographically acceptable result can vary depending upon the acceptable error or variance in a given experiment, the complexity of a sample (e.g., number and/or separation of peaks). The amount of retention drift or change the can occur while still achieving a chromatographically acceptable result can vary depending upon the duration or required reproducibility a given experiment (e.g., if reproducibility is required over a greater number of runs, the allowable retention drift or change between runs can be smaller). Therefore, it should be clear that mitigating or preventing retention drift or change does not necessarily mean the absolute elimination of retention drift or change.

In some embodiments, mitigating or preventing retention drift or change can be quantified. For example, retention drift or change can be measured for a single peak, or averaged over a set of peaks. Retention drift or change can be measured over a given period of time or number of runs. Retention drift or change can be measured relative to a standard value, starting value, or between two or more given runs.

Furthermore, retention drift or change can be quantified by a standardized test. For example, the Average % Retention Change can be calculated by taking the percent difference of the average absolute peak retentions measured from the day 3, 10 or 30 chromatographic tests from the average absolute peak retentions measured on the day one chromatographic test. For each day tested, the columns can be equilibrated under one set of test conditions followed by multiple injections of a first test mix and then equilibrated under a second set of condition followed by multiple injections of a second test mix.

In accordance with this standardized test, mitigating or preventing retention drift or change can comprises a retention drift or change of ≤5% over 30 days, ≤4% over 30 days, ≤3% over 30 days, ≤2% over 30 days, ≤1% over 30 days, ≤5% over 10 days, ≤4% over 10 days, ≤3% over 10 days, ≤2% over 10 days, ≤1% over 10 days, ≤5% over 3 days, ≤4% over 3 days, ≤3% over 3 days, ≤2% over 3 days, ≤1% over 3 days, ≤5% over 30 runs, ≤4% over 30 runs, ≤3% over 30 runs, ≤2% over 30 runs, ≤1% over 30 runs, ≤5% over 10 runs, ≤4% over 10 runs, ≤3% over 10 runs, ≤2% over 10 runs, ≤1% over 10 runs, ≤5% over 3 runs, ≤4% over 3 runs, ≤3% over 3 runs, ≤2% over 3 runs, or ≤1% over 3 runs.

In other embodiments, mitigating or preventing retention drift or change can comprises a retention drift or change of ≤5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1% over 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 days (or runs).

"High Purity" or "high purity chromatographic material" includes a material which is prepared from high purity precursors. In certain aspects, high purity materials have reduced metal contamination and/or non-diminished chromatographic properties including, but not limited to, the acidity of surface silanols and the heterogeneity of the surface.

"Chromatographic surface" includes a surface which provides for chromatographic separation of a sample. In certain aspects, the chromatographic surface is porous. In some aspects, a chromatographic surface can be the surface of a particle, a superficially porous material or a monolith. In certain aspects, the chromatographic surface is composed of the surface of one or more particles, superficially porous materials or monoliths used in combination during a chromatographic separation. In certain other aspects, the chromatographic surface is non-porous.

"Ionizable modifier" includes a functional group which bears an electron donating or electron withdrawing group. In certain aspects, the ionizable modifier contains one or more carboxylic acid groups, amino groups, imido groups, amido groups, pyridyl groups, imidazolyl groups, ureido groups, thionyl-ureido groups or aminosilane groups, or a combination thereof. In other aspects, the ionizable modifier contains a group bearing a nitrogen or phosphorous atom having a free electron lone pair. In certain aspects, the ionizable modifier is covalently attached to the material surface and has an ionizable group. In some instances it is attached to the chromatographic material by chemical modification of a surface hybrid group.

"Hydrophobic surface group" includes a surface group on the chromatographic surface which exhibits hydrophobicity. In certain aspects, a hydrophobic group can be a carbon bonded phase such as a $C_4$ to $C_{18}$ bonded phase. In other aspects, a hydrophobic surface group can contain an embedded polar group such that the external portion of the hydrophobic surface maintains hydrophobicity. In some instances it is attached to the chromatographic material by chemical modification of a surface hybrid group. In other instances the hydrophobic group can be $C_4$-$C_{30}$, embedded polar, chiral, phenylalkyl, or pentafluorophenyl bonding and coatings.

"Chromatographic core" includes chromatographic materials, including but not limited to an organic material such as silica or a hybrid material, as defined herein, in the form of a particle, a monolith or another suitable structure which forms an internal portion of the materials of the present disclosure. In certain aspects, the surface of the chromatographic core represents the chromatographic surface, as defined herein, or represents a material encased by a chromatographic surface, as defined herein. The chromatographic surface material can be disposed on or bonded to or annealed to the chromatographic core in such a way that a discrete or distinct transition is discernible or can be bound to the chromatographic core in such a way as to blend with the surface of the chromatographic core resulting in a gradation of materials and no discrete internal core surface. In certain embodiments, the chromatographic surface material can be the same or different from the material of the chromatographic core and can exhibit different physical or physiochemical properties from the chromatographic core, including, but not limited to, pore volume, surface area, average pore diameter, carbon content or hydrolytic pH stability.

"Hybrid," including "hybrid inorganic/organic material," includes inorganic-based structures wherein an organic functionality is integral to both the internal or "skeletal" inorganic structure as well as the hybrid material surface. The inorganic portion of the hybrid material can be, e.g., alumina, silica, titanium, cerium, or zirconium or oxides thereof, or ceramic material. "Hybrid" includes inorganic-based structures wherein an organic functionality is integral to both the internal or "skeletal" inorganic structure as well as the hybrid material surface. As noted above, exemplary hybrid materials are shown in U.S. Pat. Nos. 4,017,528, 6,528,167, 6,686,035 and 7,175,913, the contents of which are incorporated herein by reference in their entirety.

The term "alicyclic group" includes closed ring structures of three or more carbon atoms. Alicyclic groups include cycloparaffins or naphthenes which are saturated cyclic hydrocarbons, cycloolefins, which are unsaturated with two or more double bonds, and cycloacetylenes which have a triple bond. They do not include aromatic groups. Examples of cycloparaffins include cyclopropane, cyclohexane and cyclopentane. Examples of cycloolefins include cyclopentadiene, cyclohexadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —CF$_3$, —CN, or the like.

The term "aliphatic group" includes organic compounds characterized by straight or branched chains, typically having between 1 and 24 carbon atoms. Aliphatic groups include alkyl groups, alkenyl groups and alkynyl groups. In complex structures, the chains can be branched or cross-linked. In some embodiments, the aliphatic group can include chains having between 2 and 24 carbon atoms, or 4 and 22 carbon atoms, or 6 and 20 carbon atoms, or 8 and 18 carbon atoms, or 10 and 16 carbon atoms, or 12 and 14 carbon atoms, or any combination of these numbers, such as between about 6 and 12 carbon atoms or 10 and 14 carbon atoms. Alkyl groups include saturated hydrocarbons having one or more carbon atoms, including straight-chain alkyl groups and branched-chain alkyl groups. Such hydrocarbon moieties can be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl and the like. As used herein, the term "nitro" means —NO$_2$; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, preferably from 1 to about 6 carbon atoms.

The term "alkyl" includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has 30 or fewer carbon atoms in its backbone, e.g., $C_1$-$C_{30}$ for straight chain or $C_3$-$C_{30}$ for branched chain. In certain embodiments, a straight chain or branched chain alkyl has 20 or fewer carbon atoms in its backbone, e.g., $C_1$-$C_{20}$ for straight chain or $C_3$-$C_{20}$ for branched chain, and more preferably 18 or fewer. Likewise, preferred cycloalkyls have from 4-10 carbon atoms in their ring structure and more preferably have 4-7 carbon atoms in the ring structure. The term "lower alkyl" refers to alkyl groups having from 1 to 6 carbons in the chain and to cycloalkyls having from 3 to 6 carbons in the ring structure.

Moreover, the term "alkyl" (including "lower alkyl") as used throughout the present disclosure includes both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl(benzyl).

The term "amino," as used herein, refers to an unsubstituted or substituted moiety of the formula —NR$_a$R$_b$, in which R$_a$ and R$_b$ are each independently hydrogen, alkyl, aryl, or heterocyclyl, or R$_a$ and R$_b$, taken together with the nitrogen atom to which they are attached, forms a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of R$_a$ and R$_b$, is further substituted with an amino group.

The term "aromatic group" includes unsaturated cyclic hydrocarbons containing one or more rings. The term "mono-aromatic" includes unsaturated cyclic hydrocarbons containing one ring. The term "polyaromatic" includes unsaturated cyclic hydrocarbons containing two or more rings. Aromatic groups include 5- and 6-membered single-ring groups which can include from zero to four heteroatoms, for example, furan, pyrrole, pyrroline, oxazole, thiazole, imidazole, imidazoline, pyrazole, pyrazoline, pyrazolidine, isoxazole, isothiazole, benzene, pyridine, pyridazine, pyrimidine, pyrazine, triazine, thiophene and the like. The aromatic ring can be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like. Aromatic groups include 5- and 6-membered multiple-ring groups which can include from zero to eight heteroatoms, for example, indene, indolinzine, indole, isoindole, indoline, indazole, benzimidazole, benzthiazole, naphthalene, quinolizine, quinoline, isoquinoline, cinnoline, phthalazine, quinazoline, quinoxaline, 1,8-naphthyridine, quinuclidine, fluorene, carbazole, anthracene, acridine, phanazine, phenothiazine, phenoxazine, pyrene, and the like. Polyaromatic groups include fused aromatic groups.

The term "aryl" includes 5- and 6-membered single-ring aromatic groups that can include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine and the like. Aryl groups also include polycyclic fused aromatic groups such as naphthyl, quinolyl, indolyl and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "ceramic precursor" is intended include any compound that results in the formation of a ceramic material.

The term "chiral moiety" is intended to include any functionality that allows for chiral or stereoselective syntheses. Chiral moieties include, but are not limited to, substituent groups having at least one chiral center, natural and unnatural amino-acids, peptides and proteins, derivatized cellulose, macrocyclic antibiotics, cyclodextrins, crown ethers, and metal complexes.

The term "embedded polar functionality" is a functionality that provides an integral polar moiety such that the interaction with basic samples due to shielding of the unreacted silanol groups on the silica surface is reduced. Embedded polar functionalities include, but are not limited to carbonate, amide, urea, ether (e.g., —O— between to carbon containing groups), thioether, sulfinyl, sulfoxide, sulfonyl, thiourea, thiocarbonate, thiocarbamate, ethylene glycol, heterocyclic, triazole functionalities or carbamate functionalities such as disclosed in U.S. Pat. No. 5,374,755, and chiral moieties.

The language "chromatographically-enhancing pore geometry" includes the geometry of the pore configuration of the presently-disclosed materials, which has been found to enhance the chromatographic separation ability of the material, e.g., as distinguished from other chromatographic media in the art. For example, a geometry can be formed, selected or constructed, and various properties and/or factors can be used to determine whether the chromatographic separations ability of the material has been "enhanced," e.g., as compared to a geometry known or conventionally used in the art. Examples of these factors include high separation efficiency, longer column life and high mass transfer properties (as evidenced by, e.g., reduced band spreading and good peak shape.) These properties can be measured or observed using art-recognized techniques. For example, the chromatographically-enhancing pore geometry of the present porous inorganic/organic hybrid materials is distinguished from the prior art materials by the absence of "ink bottle" or "shell shaped" pore geometry or morphology, both of which are undesirable because they, e.g., reduce mass transfer rates, leading to lower efficiencies.

Chromatographically-enhancing pore geometry is found in hybrid materials containing only a small population of micropores. A small population of micropores is achieved in hybrid materials when all pores of a diameter of about <34 Å contribute less than about 110 m$^2$/g to the specific surface area of the material. Hybrid materials with such a low micropore surface area (MSA) give chromatographic enhancements including high separation efficiency and good mass transfer properties (as evidenced by, e.g., reduced band spreading and good peak shape). Micropore surface area (MSA) is defined as the surface area in pores with diameters less than or equal to 34 Å, determined by multipoint nitrogen sorption analysis from the adsorption leg of the isotherm using the BJH method. As used herein, the acronyms "MSA" and "MPA" are used interchangeably to denote "micropore surface area."

The term "functionalizing group" includes organic functional groups which impart a certain chromatographic functionality to a chromatographic stationary phase.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character, i.e., "heterocyclic aromatic group". They include one or more ring structures. Heterocyclic groups having two or more ring structures are "polyheterocyclic aromatic groups". These groups can have fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like. Suitable heteroaromatic and heteroalicyclic groups generally will have 1 to 3 separate or fused rings with 3 to about 8 members per ring and one or more N, O or S atoms, e.g., coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "metal oxide precursor" is intended to include any compound that contains a metal and results in the formation of a metal oxide, e.g., alumina, silica, titanium oxide, zirconium oxide.

The term "monolith" is intended to include a collection of individual particles packed into a bed formation, in which the shape and morphology of the individual particles are maintained. The particles are advantageously packed using a material that binds the particles together. Any number of binding materials that are well known in the art can be used such as, for example, linear or cross-linked polymers of divinylbenzene, methacrylate, urethanes, alkenes, alkynes, amines, amides, isocyanates, or epoxy groups, as well as condensation reactions of organoalkoxysilanes, tetraalkoxysilanes, polyorganoalkoxysiloxanes, polyethoxysiloxanes, and ceramic precursors. In certain embodiments, the term "monolith" also includes hybrid monoliths made by other methods, such as hybrid monoliths detailed in U.S. Pat. No. 7,250,214; hybrid monoliths prepared from the condensation of one or more monomers that contain 0-99 mole percent silica (e.g., $SiO_2$); hybrid monoliths prepared from coalesced porous inorganic/organic particles; hybrid monoliths that have a chromatographically-enhancing pore geometry; hybrid monoliths that do not have a chromatographically-enhancing pore geometry; hybrid monoliths that have ordered pore structure; hybrid monoliths that have non-periodic pore structure; hybrid monoliths that have non-crystalline or amorphous molecular ordering; hybrid monoliths that have crystalline domains or regions; hybrid monoliths with a variety of different macropore and mesopore properties; and hybrid monoliths in a variety of different aspect ratios. In certain embodiments, the term "monolith" also includes inorganic monoliths, such as those described in G. Guiochon/*J. Chromatogr.* A 1168 (2007) 101-168.

The term "nanoparticle" is a microscopic particle/grain or microscopic member of a powder/nanopowder with at least one dimension less than about 100 nm, e.g., a diameter or particle thickness of less than about 100 nm (0.1 mm), which can be crystalline or noncrystalline. Nanoparticles have properties different from, and often superior to, those of conventional bulk materials including, for example, greater strength, hardness, ductility, sinterability, and greater reactivity among others. Considerable scientific study continues to be devoted to determining the properties of nanomaterials, small amounts of which have been synthesized (mainly as nano-size powders) by a number of processes including colloidal precipitation, mechanical grinding, and gas-phase nucleation and growth. Extensive reviews have documented recent developments in nano-phase materials, and are incorporated herein by reference thereto: Gleiter, H. (1989) "Nano-crystalline materials," *Prog. Mater. Sci.* 33:223-315 and Siegel, R. W. (1993) "Synthesis and properties of nano-phase materials," *Mater. Sci. Eng.* A168:189-197. In certain embodiments, the nanoparticles comprise oxides or nitrides of the following: silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, and mixtures thereof. In certain embodiments, the nanoparticles of the present disclosure are selected from diamonds, zirconium oxide (amorphous, monoclinic, tetragonal and cubic forms), titanium oxide (amorphous, anatase, brookite and rutile forms), aluminum (amorphous, alpha, and gamma forms), and boronitride (cubic form). In particular embodiments, the nanoparticles of the present disclosure are selected from nano-diamonds, silicon carbide, titanium dioxide (anatase form), cubic-boronitride, and any combination thereof. Moreover, in particular embodiments, the nanoparticles can be crystalline or amorphous. In particular embodiments, the nanoparticles are less than or equal to 100 mm in diameter, e.g., less than or equal to 50 mm in diameter, e.g., less than or equal to 20 mm in diameter.

Moreover, it should be understood that the nanoparticles that are characterized as dispersed within the composites of the present disclosure are intended to describe exogenously added nanoparticles. This is in contrast to nanoparticles, or formations containing significant similarity with putative nanoparticles, that are capable of formation in situ, wherein, for example, macromolecular structures, such as particles, can comprise an aggregation of these endogenously created.

The term "substantially disordered" refers to a lack of pore ordering based on x-ray powder diffraction analysis. Specifically, "substantially disordered" is defined by the lack of a peak at a diffraction angle that corresponds to a d value (or d-spacing) of at least 1 nm in an x-ray diffraction pattern.

"Surface modifiers" include, typically, organic functional groups which impart a certain chromatographic functionality to a chromatographic stationary phase. The porous inorganic/organic hybrid materials possess both organic groups and silanol groups which can additionally be substituted or derivatized with a surface modifier.

The language "surface modified" is used herein to describe the composite material of the present disclosure that possess both organic groups and silanol groups which can additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later cross-linking, imparting the chemical character of the surface modifier to the base material. In one embodiment, the organic groups of a hybrid material react to form an organic covalent bond with a surface modifier. The modifiers can form an organic covalent bond to the material's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds. A variety of synthetic transformations are well known in the literature, see, e.g., March, J. *Advanced Organic Chemistry,* 3rd Edition, Wiley, New York, 1985.

Chromatographic materials of the present disclosure can include those comprising a silica core material, metal oxide core material, an inorganic-organic hybrid material or a group of block copolymers thereof core material. The core material can be a high purity chromatographic core composition as discussed herein. Similarly, the chromatographic core material can be a regular, e.g., not high purity, version/analog/homolog of the high purity materials discussed herein.

Examples of suitable core materials include, but are not limited to, conventional chromatographic silica materials, metal oxide materials, inorganic-organic hybrid materials or a group of block copolymers thereof, ceramic, silicon oxide, silicon imidonitride, silicon nitride, silicon aluminum nitride, silicon diimide, and silicon oxynitride. Additional examples of suitable core materials (for use with or without modification) are described in US Pub. Nos. 2009/0127177, 2007/0135304, 2009/0209722, 2007/0215547, 2007/0141325, 2011/0049056, 2012/0055860, and 2012/0273404 as well as International Pub. No. WO2008/103423, which are incorporated herein by reference in their entirety.

The chromatographic core material can be in the form of discreet particles or can be a monolith. The chromatographic core material can be any porous material and can be commercially available or can be produced by known methods, such as those methods described in, for example, in U.S. Pat. Nos. 4,017,528, 6,528,167, 6,686,035 and 7,175,913, which are incorporated herein by reference in their entirety. In some embodiments, the chromatographic core material can be a non-porous core.

The composition of the chromatographic surface material and the chromatographic core material can be varied by one of ordinary skill in the art to provide enhanced chromatographic selectivity, enhanced column chemical stability, enhanced column efficiency, and/or enhanced mechanical strength. Similarly, the composition of the surrounding material provides a change in hydrophilic/lipophilic balance (HLB), surface charge (e.g., isoelectric point or silanol $pK_a$), and/or surface functionality for enhanced chromatographic separation. Furthermore, in some embodiments, the composition of the chromatographic material can also provide a surface functionality for available for further surface modification.

The ionizable groups and the hydrophobic surface groups of the chromatographic materials of the present disclosure can be prepared using known methods. Some of the ionizable modifier reagents are commercially available. For example, silanes having amino alkyl trialkoxysilanes, methyl amino alkyl trialkoxysilanes, and pyridyl alkyl trialkoxysilanes are commercially available. Other silanes such as chloropropyl alkyl trichlorosilane and chloropropyl alkyl trialkoxysilane are also commercially available. These can be bonded and reacted with imidazole to create imidazolyl alkyl silyl surface species, or bonded and reacted with pyridine to create pyridyl alkyl silyl surface species. Other acidic modifiers are also commercially available, including, but not limited to, sulfopropyltrisilanol, carboxyethylsilanetriol, 2-(carbomethoxy) ethylmethyldichlorosilane, 2-(carbomethoxy) ethyltrichlorosilane, 2-(carbomethoxy) ethyltrimethoxysilane, n-(trimethoxysilylpropyl) ethylenediamine, triacetic acid, (2-diethylphosphatoethyl) triethoxysilane, 2-(chlorosulfonylphenyl) ethyltrichlorosilane, and 2-(chlorosulfonylphenyl) ethyltrimethoxysilane.

It is known to one skilled in the art to synthesize these types of silanes using common synthetic protocols, including Grignard reactions and hydrosilylations. Products can be purified by chromatography, recrystallization or distillation.

Other additives such as isocyanates are also commercially available or can be synthesized by one skilled in the art. A common isocyanate forming protocol is the reaction of a primary amine with phosgene or a reagent known as triphosgene.

In one aspect, the present disclosure relates to a method of separating a compound of interest from a mixture, the method comprising (a) providing a mixture containing the compound of interest; (b) introducing a portion of the mixture to a chromatographic system having a chromatographic column; and (c) eluting the separated compound of interest from the column; wherein the column has a stationary phase having the following structure (i):

$$[X](W)_a(Q)_b(T)_c \qquad (i)$$

wherein:

X is a chromatographic substrate containing silica, metal oxide, an inorganic-organic hybrid material, a group of block copolymers, or combinations thereof;

W is selected from the group consisting of hydrogen and hydroxyl, wherein W is bound to the surface of X;

Q is a first substituent which minimizes analyte retention variation over time under chromatographic conditions having low water concentrations;

T is a second substituent which chromatographically retains the analyte, wherein T has one or more monoaromatic, polyaromatic, heterocyclic aromatic, or polyheterocyclic aromatic groups, each group being optionally substituted with an aliphatic group; and b and c are positive numbers, 0.05≤(b/c)≤100, and a≥0.

In various embodiments, the selectivity of a chromatographic material can be controlled or influenced through the selection of Q and/or T, the density of Q and/or T on the surface, or a combination thereof. In some embodiments, both Q and T play a role in retaining the compound of interest. In other embodiments, T selectively retains each different compound of interest.

In various embodiments, the present disclosure provides a bonded chromatographic material to which ligands can be attached. The high density coverage attained by the bonding method of the present invention can be 2× to 3× higher than silane bonding chemistries currently practiced in conventional SFC materials. A combination of high coverage and the other properties of Q and/or T can prevent the interaction of surface silanols with analytes.

In various embodiments, the present disclosure provides high density of bonded phases increases retention and prevents retention drift or change caused by analyte interactions with surface silanols or other secondary retention mechanisms. Elimination of these secondary and minor selectivity components greatly improves peak shape and column peak capacity, especially for basic analytes.

In various embodiments, the present disclosure provides for the use of a coupling chemistry based two component system produces an even coverage of mixed surface functionality. Unlike mixed particle beds where two separate particles with different surface chemistries are mixed this material has an even, and predictable, surface character throughout. A column packed with such material is not prone to chromatographic instability due to poor particle mixing or particle type segregation during column packing.

In various embodiments, the present disclosure provides for column packing that is simplified due to the use of a single particle slurry.

In various embodiments, the present disclosure provides for a chromatographic packing material with enhanced selectivity for acidic, neutral and basic analytes in a single column without the use of a mixed or multiple particle based bed.

In various embodiments, the present disclosure provides for a ratio of the components on the particle surface that can be easily manipulated to alter the selectivity of the support providing a wide range of options for chromatographic separation.

In various embodiments, the present disclosure provides for bonding chemistry whereby the formation of a cross-linked film of the silane surface modifying agent either through polymerization of the surface reactive groups or by the addition of a cross linking agent either before during or after the addition of the selectivity ligand.

In certain other embodiments, the chromatographic material of the present disclosure is non-porous. In another embodiment, the chromatographic material of the present disclosure is hydrolytically stable at a pH of about 1 to about 14; at a pH of about 10 to about 14; or at a pH of about 1 to about 5.

In another aspect, the present disclosure provides materials as described herein wherein the chromatographic material further comprises a nanoparticle or a mixture of more than one nanoparticles dispersed within the chromatographic surface.

In certain embodiments, the nanoparticle is present in <20% by weight of the nanocomposite, <10% by weight of the nanocomposite, or <5% by weight of the nanocomposite.

In other embodiments, the nanoparticle is crystalline or amorphous and can be silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, oxides thereof, or a nitride thereof. In particular embodiments, the nanoparticle is a substance which comprises one or more moieties selected from the group consisting of nano-diamonds, silicon carbide, titanium dioxide, and cubic-boronitride. In other embodiments, the nanoparticles can be less than or equal to 200 nm in diameter, less than or equal to 100 nm in diameter, less than or equal to 50 nm in diameter, or less than or equal to 20 nm in diameter.

In one or more embodiments, Q is represented by:

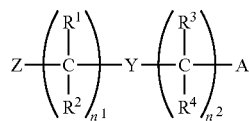

(ii)

wherein:
$n^1$ is an integer from 1-30;
$n^2$ is an integer from 1-30;
$R^1$, $R^2$, $R^3$ and $R^4$ are each independently selected from the group consisting of hydrogen, hydroxyl, fluoro, methyl, ethyl, n-propyl, iso-propyl, n-butyl, iso-butyl, tert-butyl, lower alkyl, a protected or deprotected alcohol, and a zwitterion;

Z is
(a) a surface attachment group having the formula $(B^1)_x(R^5)_y(R^6)_z Si-$, wherein x is an integer from 1-3, y is an integer from 0-2, z is an integer from 0-2, and x+y+z=3; $R^5$ and $R^6$ are each independently selected from the group consisting of methyl, ethyl, n-propyl, iso-propyl, n-butyl, iso-butyl, tert-butyl, substituted or unsubstituted aryl, cyclic alkyl, branched alkyl, lower alkyl, a protected or deprotected alcohol, a zwitterion group and a siloxane bond; and $B^1$ is a siloxane bond;

(b) an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage; or (c) an adsorbed, surface group that is not covalently attached to the surface of the material;

Y is an embedded polar functionality; and

A is selected from the group consisting of an hydrophilic terminal group, a functionizable group, hydrogen, hydroxyl, fluoro, methyl, ethyl, n-propyl, iso-propyl, n-butyl, iso-butyl, tert-butyl, a lower alkyl and a polarizable group.

In one or more embodiments, T is represented by:

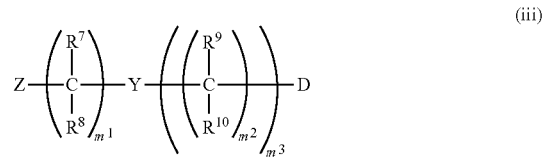

(iii)

wherein
$m^1$ is an integer from 1-30;
$m^2$ is an integer from 1-30;
$m^3$ is an integer from 1-3;
$R^7$, $R^8$, $R^9$ and $R^{10}$ are each independently selected from the group consisting of hydrogen, hydroxyl, fluoro, methyl, ethyl, n-propyl, iso-propyl, n-butyl, iso-butyl, tert-butyl, lower alkyl, a protected or deprotected alcohol, a zwitterion, an aromatic hydrocarbon group and a hetercyclic aromatic hydrocarbon group;

Z is
(a) a surface attachment group having the formula $(B^1)_x(R^5)_y(R^6)_z Si-$, wherein x is an integer from 1-3, y is an integer from 0-2, z is an integer from 0-2, and x+y+z=3; $R^5$ and $R^6$ are each independently selected from the group consisting of methyl, ethyl, n-propyl, iso-propyl, n-butyl, iso-butyl, tert-butyl, substituted or unsubstituted aryl, cyclic alkyl, branched alkyl, lower alkyl, a protected or deprotected alcohol, a zwitterion group and a siloxane bond; and $B^1$ is a siloxane bond;

(b) an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage; or (c) an adsorbed, surface group that is not covalently attached to the surface of the material;

Y is an embedded polar functionality;

D is selected from the group consisting of a bond, N, O, S,
—$(CH_2)_{0-12}$—N—$R^{11}R^{12}$,
—$(CH_2)_{0-12}$—O—$R^{11}$,
—$(CH_2)_{0-12}$—S—$R^{11}$,
—$(CH_2)_{0-12}$—N—$(CH_2)_{0-12}$—$R^{11}R^{12}$,
—$(CH_2)_{0-12}$—O—$(CH_2)_{0-12}$—$R^{11}$,
—$(CH_2)_{0-12}$—S—$(CH_2)_{0-12}$—$R^{11}$,
—$(CH_2)_{0-12}$—$S(O)_{1-2}$—$(CH_2)_{0-12}$—N—$R^{11}R^{12}$,
—$(CH_2)_{0-12}$—$S(O)_{1-2}$—$(CH_2)_{0-12}$—O—$R^{11}$,
—$(CH_2)_{0-12}$—$S(O)_{1-2}$—$(CH_2)_{0-12}$—S—$R^{11}$;
—$(CH_2)_{0-12}$—$S(O)_{1-2}$—$(CH_2)_{0-12}$—N—$(CH_2)_{0-12}$—$R^{11}R^{12}$,
—$(CH_2)_{0-12}$—$S(O)_{1-2}$—$(CH_2)_{0-12}$—O—$(CH_2)_{0-12}$—$R^{11}$, and
—$(CH_2)_{0-12}$—$S(O)_{1-2}$—$(CH_2)_{0-12}$—S—$(CH_2)_{0-12}$—$R^{11}$, $R^{11}$ is a first mono-aromatic, polyaromatic, heterocyclic aromatic, or polyheterocyclic aromatic group; and $R^{12}$ is a hydrogen, an aliphatic group or a second mono-aromatic, polyaromatic, heterocyclic aromatic, or polyheterocyclic aromatic group, wherein $R^{11}$ and $R^{12}$ are optionally substituted with one or more groups selected from the group consisting of an aliphatic group, a halogen, a hydroxyl, a thiol, an amino, an alkoxy, an alkylcarboxy, an alkylthio, and a nitro group.

In some embodiments, the first or second mono-aromatic, polyaromatic, heterocyclic aromatic, or polyheterocyclic aromatic group of $R^{11}$ or $R^{12}$ can be a polyaromatic or polyhetercyclic aromatic hydrocarbon with at least 2 aromatic rings. The first or second mono-aromatic, polyaromatic, heterocyclic aromatic, or polyheterocyclic aromatic group of $R^{11}$ or $R^{12}$ can also be a polyaromatic or polyhetercyclic aromatic hydrocarbon with at least 3 aromatic rings. The first or second mono-aromatic, polyaromatic, heterocyclic aromatic, or polyheterocyclic aromatic group of $R^{11}$ or $R^{12}$ can also be a polyaromatic or polyhetercyclic aromatic hydrocarbon with at least 4 aromatic rings.

In one embodiment, the first or second mono-aromatic, polyaromatic, heterocyclic aromatic, or polyheterocyclic aromatic group of $R^{11}$ or $R^{12}$ is selected from the group consisting of furan, pyrrole, pyrroline, oxazole, thiazole, imidazole, imidazoline, pyrazole, pyrazoline, pyrazolidine, isoxazole, isothiazole, benzene, pyridine, pyridazine, pyrimidine, pyrazine, triazine, thiophene, indene, indolinzine, indole, isoindole, indoline, indazole, benzimidazole, benzthiazole, naphthalene, quinolizine, quinoline, isoquinoline, cinnoline, phthalazine, quinazoline, quinoxaline, 1,8-naphthyridine, quinuclidine, fluorene, carbazole, anthracene, acridine, phanazine, phenothiazine, phenoxazine, pyrene, and derivatives thereof, wherein the group is unsubstituted or optionally substituted with a aliphatic group.

In other embodiments, the first or second mono-aromatic, polyaromatic, heterocyclic aromatic, or polyheterocyclic aromatic group of $R^{11}$ or $R^{12}$ can be substituted with at least one $C_1$-$C_{24}$ aliphatic group. In particular, the groups can be substituted with at least one $C_2$-$C_{22}$ aliphatic group, one $C_3$-$C_{20}$ aliphatic group, one $C_4$-$C_{18}$ aliphatic group, one $C_5$-$C_{16}$ aliphatic group, one $C_6$-$C_{14}$ aliphatic group, one $C_7$-$C_{12}$ aliphatic group, one $C_8$-$C_{10}$ aliphatic group, or one aliphatic group of any combination of preceding carbon lengths, e.g. a $C_8$-$C_{18}$ aliphatic group, or other various sized groups as described in the present disclosure.

R11 or R12 can be an aminoanthracene (e.g., 1-aminoanthracene, 2-aminoanthracene or 9-amino anthracene) or a methylaminoanthracene (e.g. 1-methylaminoanthracene, 2-methylaminoanthracene or 9-methylaminoanthracene). The aminoanthracene or methylaminoanthracene can be substituted on the ring structure with one more aliphatic groups, for example, a lower alkyl. In some embodiments, the aminoanthracene or methylaminoanthracene can have the formula (X)-amino-(Y)-alkyl-anthracene or (X)-methyl-amino-(Y)-alkyl-anthracene wherein X is 1, 2 or 9 and Y is 1-10 representing the carbon positions on anthracene (e.g., 1-amino-1-methyl-anthracene; 1-amino-2-methyl-anthracene; 1-amino-3-methyl-anthracene; 1-amino-4-methyl-anthracene; 1-amino-5-methyl-anthracene; 1-amino-6-methyl-anthracene; 1-amino-7-methyl-anthracene; 1-amino-8-methyl-anthracene; 1-amino-9-methyl-anthracene; 1-amino-10-methyl-anthracene; 1-methylamino-1-methyl-anthracene; 1-methylamino-2-methyl-anthracene; 1-methylamino-3-methyl-anthracene; 1-methylamino-4-methyl-anthracene; 1-methylamino-5-methyl-anthracene; 1-methylamino-6-methyl-anthracene; 1-methylamino-7-methyl-anthracene; 1-methylamino-8-methyl-anthracene; 1-methylamino-9-methyl-anthracene; and 1-methylamino-10-methyl-anthracene, etc.).

In other embodiments, the aminoanthracene or methylaminoanthracene can have the formula (X)-amino-(Y)-alkyl-(Z)-alkyl-anthracene or (X)-methylamino-(Y)-alkyl-(Z)-alkyl-anthracene wherein X is 1, 2 or 9 and, Y and Z are 1-10 representing the carbon positions on anthracene, provided Y and Z are not the same (e.g., 1-amino-1-methyl-2-methyl-anthracene; 1-amino-1-methyl-3-methyl-anthracene; 1-amino-1-methyl-4-methyl-anthracene; 1-amino-1-methyl-5-methyl-anthracene; 1-amino-1-methyl-6-methyl-anthracene; 1-amino-1-methyl-7-methyl-anthracene; 1-amino-1-methyl-8-methyl-anthracene; 1-amino-1-methyl-9-methyl-anthracene; 1-amino-1-methyl-10-methyl-anthracene; etc.). The aminoanthracene or methylaminoanthracene can be disubstituted on the ring structure with a second polar group, for example, an amine (e.g., 1-amino, 4-N,N-dimethylamino anthracene).

R11 or R12 can be a naphthylamine (e.g., 1-naphthylamine, or 2-naphthylamine) or a methylnaphthylamine (e.g., 1-methylnaphthylamine, or 2-methylnaphthylamine). The naphthylamine or methylnaphthylamine can be substituted with one more aliphatic groups, for example, a lower alkyl. In some embodiments, the naphthylamine or methylnaphthylamine can have the formula (X')-amino-(Y')-alkyl-naphthalene or (X')-methylamino-(Y')-alkyl-naphthalene wherein X' is 1 or 2 and Y' is 1-8 representing the carbon positions on naphthalene (e.g., 1-amino-1-methyl-naphthalene; 1-amino-2-methyl-naphthalene; 1-amino-3-methyl-naphthalene; 1-amino-4-methyl-naphthalene; 1-amino-5-methyl-naphthalene; 1-amino-6-methyl-naphthalene; 1-amino-7-methyl-naphthalene; 1-amino-8-methyl-naphthalene; 9 and 10 positions are non-substitutable; 1-methylamino-1-methyl-naphthalene; 1-methylamino-2-methyl-naphthalene; 1-methylamino-3-methyl-naphthalene; 1-methylamino-4-methyl-naphthalene; 1-methylamino-5-methyl-naphthalene; 1-methylamino-6-methyl-naphthalene; 1-methylamino-7-methyl-naphthalene; 1-methylamino-8-methyl-naphthalene; etc.).

In other embodiments, the naphthylamine or methylnaphthylamine can have the formula (X')-amino-(Y')-alkyl-(Z')-alkyl-naphthalene or (X')-methylamino-(Y')-alkyl-(Z')-alkyl-naphthalene wherein X' is 1 or 2 and, Y' and Z' are 1-10 representing the carbon positions on naphthalene, provided Y' and Z' are not the same (e.g., 1-amino-1-methyl-2-methyl-naphthalene; 1-amino-1-methyl-3-methyl-naphthalene; 1-amino-1-methyl-4-methyl-naphthalene; 1-amino-1-methyl-5-methyl-naphthalene; 1-amino-1-methyl-6-methyl-naphthalene; 1-amino-1-methyl-7-methyl-naphthalene; 1-amino-1-methyl-8-methyl-naphthalene; etc.).

R11 or R12 can be an aminophenanthrene (e.g., 1-aminophenanthrene, 2-aminophenanthrene, 3-aminophenanthrene, 4-aminophenanthrene or 9-aminophenanthrene) or a methylaminophenanthrene (e.g., 1-methylaminophenanthrene, 2-methylaminophenanthrene, 3-methylaminophenanthrene, 4-methylaminophenanthrene or 9-methylaminophenanthrene). The aminophenanthrene or methylaminophenanthrene can be substituted on the ring structure with one more aliphatic groups, for example, a lower alkyl. In some embodiments, the aminophenanthrene or methylaminophenanthrene can have the formula (X")-amino-(Y")-alkyl-phenanthrene or (X")-methylamino-(Y")-alkyl-phenanthrene wherein X is 1, 2, 3, 4 or 9 and Y is 1-10 representing the carbon positions on phenanthrene (e.g., 1-amino-1-methyl-phenanthrene; 1-amino-2-methyl-phenanthrene; 1-methylamino-1-methyl-phenanthrene; 1-methylamino-2-methyl-phenanthrene; etc.).

In other embodiments, the aminophenanthrene or methylaminophenanthrene can have the formula (X")-amino-(Y")-alkyl-(Z")-alkyl-phenanthrene or (X")-methylamino-(Y")-alkyl-(Z")-alkyl-phenanthrene wherein X is 1, 2, 3, 4 or 9 and, Y and Z are 1-10 (not counting the junction carbons)

representing the carbon positions on phenanthrene, provided Y and Z are not the same (e.g., 1-amino-1-methyl-2-methyl-phenanthrene; etc.).

Similarly, R11 or R12 can be an aminopyrene (e.g., 1-aminopyrene, 2-aminopyrene, 3-aminopyrene, 4-aminopyrene or 5-aminopyrene) or a methylaminopyrene (e.g., 1-methylaminopyrene, 2-methylaminopyrene, 3-methylaminopyrene, 4-methylaminopyrene or 5-methylaminopyrene). The aminopyrene and methylaminopyrene can be similarly substituted as the aminoanthracene and methylaminoanthracene.

Similarly, R11 or R12 can be an aminochrysene (e.g., 1-aminochrysene, 2-aminochrysene, 3-aminochrysene, 4-aminochrysene, 5-aminochrysene, or 6-aminochrysene) or a methylaminochrysene (e.g., 1-methylaminochrysene, 2-methylaminochrysene, 3-methylaminochrysene, 4-methylaminochrysene, 5-methylaminochrysene, or 6-methylaminochrysene). The aminochrysene and methylaminochrysene can be similarly substituted as the aminoanthracene and methylaminoanthracene.

In some embodiments, T is represented by one of the following structures:

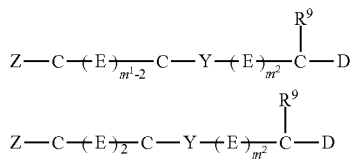

wherein each E is independently a bond or a lower alkyl that can be optionally substituted with an hydroxyl, fluoro, methyl, ethyl, n-propyl, iso-propyl, n-butyl, iso-butyl, tert-butyl, lower alkyl, a protected or deprotected alcohol, a zwitterion, an aromatic hydrocarbon group or a heterocyclic aromatic hydrocarbon group, and wherein Z, Y, $R^9$, $m^1$, $m^2$ and D are defined above.

In other embodiments, T is represented by one of the following structures:

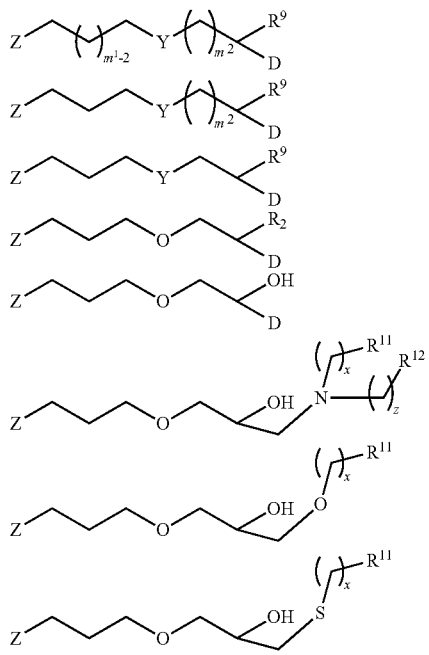

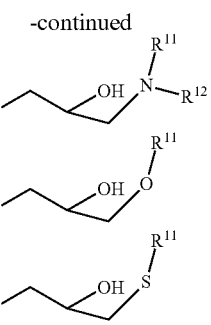

wherein Z, Y, $R^9$, $m^1$, $m^2$ and D are defined above.

In some embodiments, b and c are positive numbers, with a ratio $0.05 \leq (b/c) \leq 100$, and $a \geq 0$. In some embodiments, Q and T are different, whereas in other embodiments Q and T are the same. Q can include two or more different moieties, and T can include two or more different moieties. In some embodiments, the first, second, third, fourth, and fifth fraction are each independently about 0-100, 1-99, 5-95, 10-90, 20-80, 30-70, 40-60, 0, 5, 10, 15, 20, 25, 30, 35, 40, 45, 50, 55, 60, 65, 70, 75, 80, 85, 90, or 95%.

In one or more embodiments, Q is non-polar. In some embodiments, Q comprises a borate or nitro functional group. In some embodiments, Q is represented by one of:

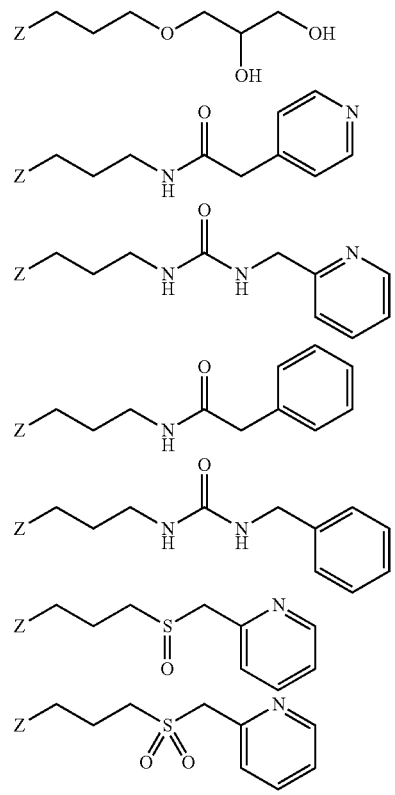

wherein Z can include a surface attachment group having the formula $(B^1)_x(R^5)_y(R^6)_z Si-$, wherein x is an integer from 1-3, y is an integer from 0-2, z is an integer from 0-2, and $x+y+z=3$. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group, and $B^1$ can represent a siloxane bond.

In another embodiment, Z is an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In yet another embodiment, Z is an adsorbed, surface group that is not covalently attached to the surface of the material.

In some embodiments, T is represented by one of:

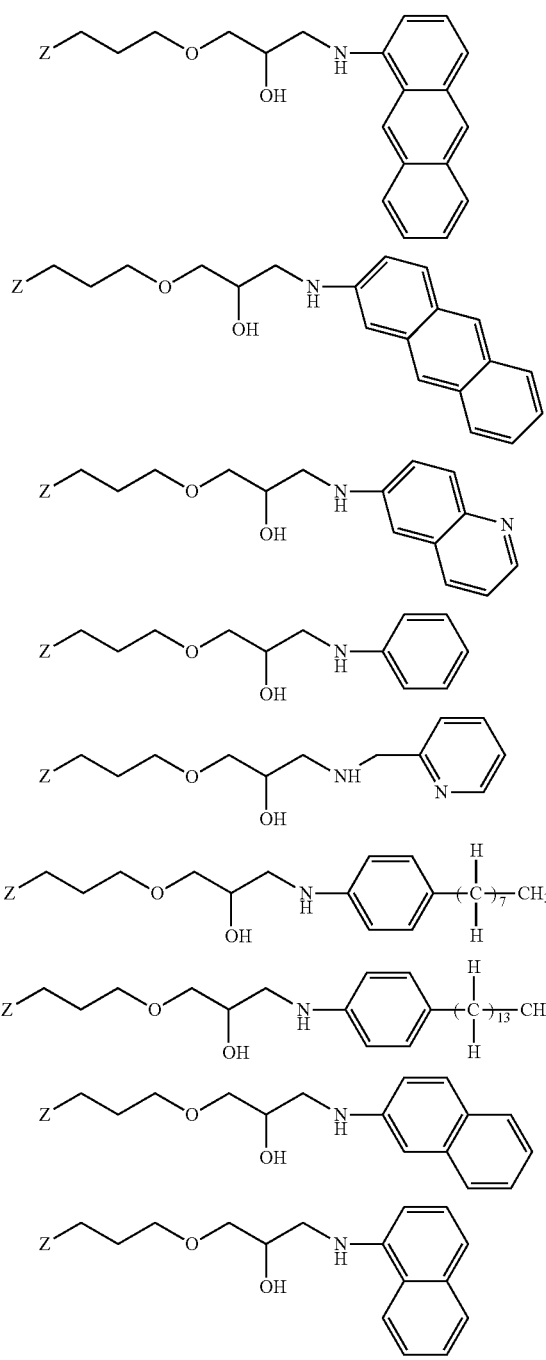

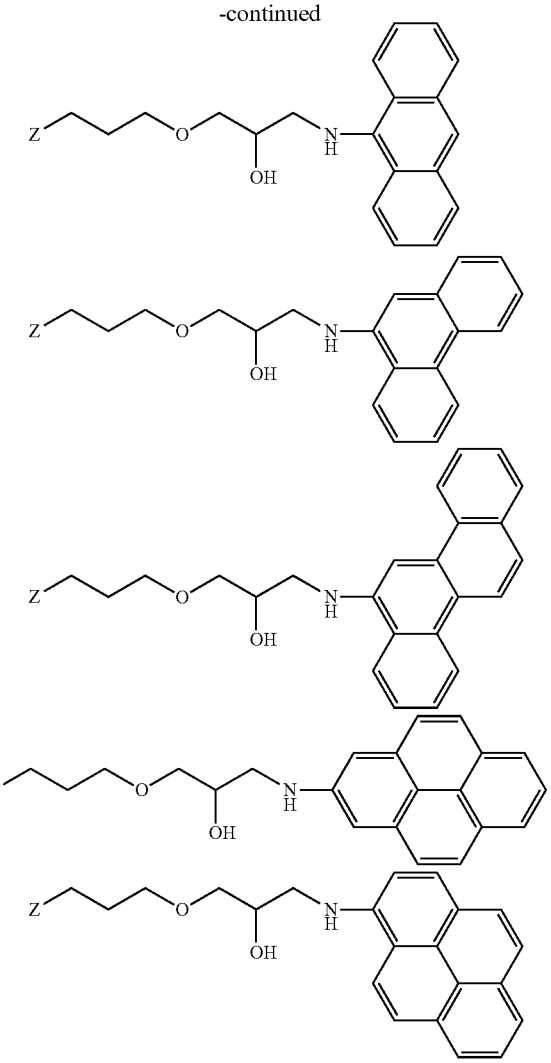

wherein Z can include a surface attachment group having the formula $(B^1)_x(R^5)_y(R^6)_z Si-$, wherein x is an integer from 1-3, y is an integer from 0-2, z is an integer from 0-2, and $x+y+z=3$. Each occurrence of $R^5$ and $R^6$ can independently represent methyl, ethyl, n-propyl, iso-propyl, n-butyl, iso-butyl, tert-butyl, substituted or unsubstituted aryl, cyclic alkyl, branched alkyl, lower alkyl, a protected or deprotected alcohol, a zwitterion group and a siloxane bond, and $B^1$ can represent a siloxane bond. In some embodiments, Z is an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In some embodiments, Z is an adsorbed, surface group that is not covalently attached to the surface of the material.

In some embodiments, the first or second mono-aromatic, polyaromatic, heterocyclic aromatic, or polyheterocyclic aromatic group of $R^{11}$ or $R^{12}$ can be converted to a cycloolefin. For example, a pyridine group may be converted to a cycloolefin in solution under certain conditions. In some circumstances, the cycloolefin retains sufficient unsaturation to retain and separate structurally related compound(s) of interest from a mixture. In particular situations, a stationary phase of the present disclosure containing the cycloolefin can retain, separate and resolution of critical pairs related to vitamins (e.g., D2 and D3, K1 and K2).

Figure 4:
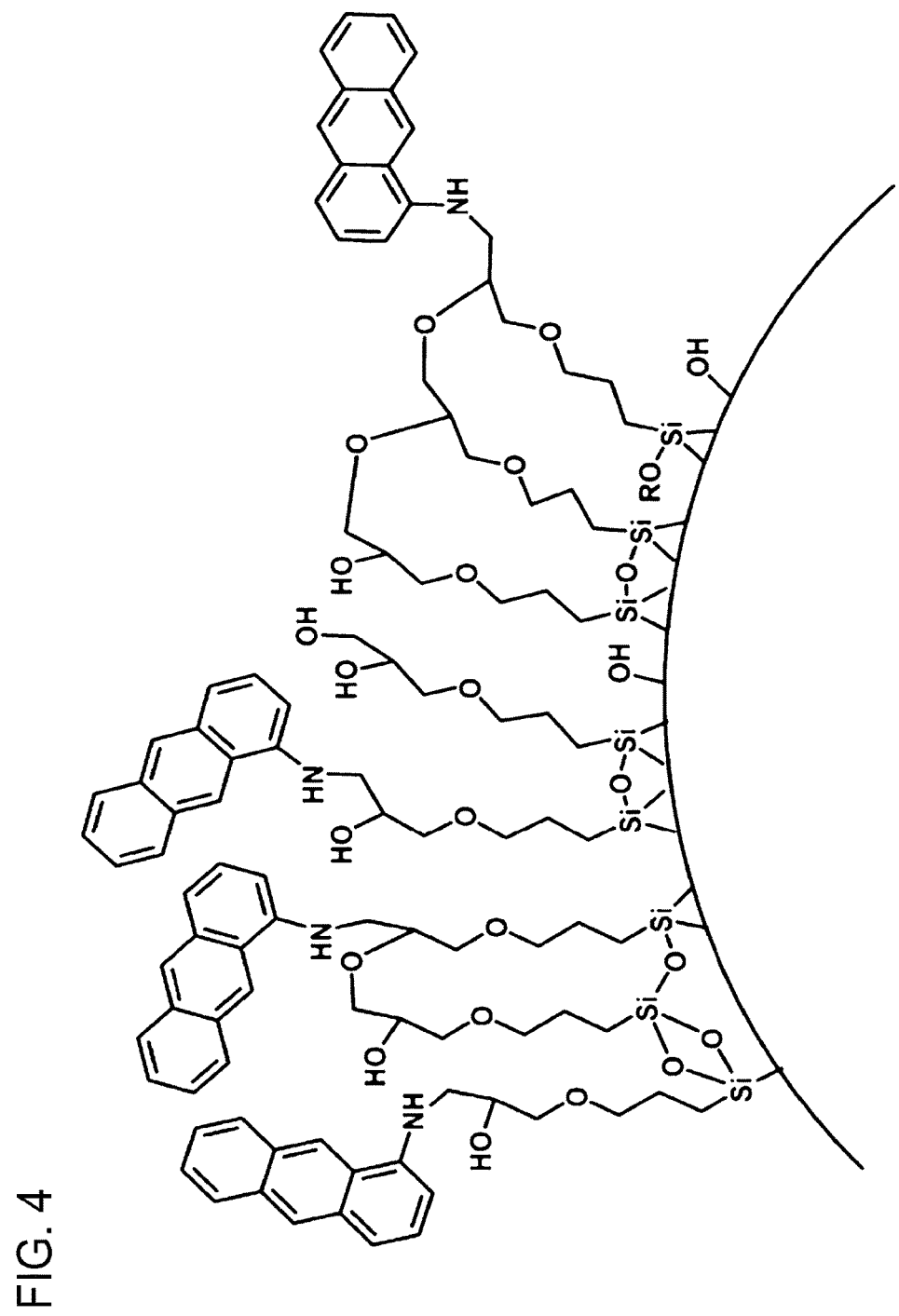
FIG. 4 shows a schematic of a chromatographic surface crosslinked with the modifying agents GPTMS and 1-aminoanthracene.

The Q and T substituents can also be polymerized. The Q and T substituents can be polymerized to each itself, e.g., Q-Q, T-T, or polymerized to each other, e.g. Q-T. As illustrated in FIG. 4, polymerization can occur at the surface level between the siloxane groups, between the hydrocarbon substituents, or both. Polymerization between the substituents can create a crosslinked surface coating, or a second coating above the surface coating, e.g. a second layer of substituents which may or may not also be polymerized, or a mixture of both. The degree of polymerization of the Q and T substituents can vary. For example, a first fraction of Q can be bound to X and a second fraction of Q can be polymerized. Likewise, a first fraction of T can be bound to X, and a second fraction of T can be polymerized. In another embodiment, a first fraction of Q can be bound to X, a second fraction of Q can be polymerized, a third fraction of T can be bound to X, and a fourth fraction of T can be polymerized. The polymerized portions of Q and T can be polymerized to itself or to each other.

In one or more embodiments of any of the above aspects, X is a high purity chromatographic material having a core surface that is subject to alkoxylation by a chromatographic mobile phase under chromatographic conditions. X can be a chromatographic material having a core surface that is subject to alkoxylation by a chromatographic mobile phase under chromatographic conditions. In some embodiments, the functional group including Q is a diol. The functional group including T can be an amine, an ether, a thioether, or a combination thereof. T can include a chiral functional group adapted for a chiral separation, Q can include a chiral functional group adapted for a chiral separation, or T and Q can both include a chiral functional group adapted for a chiral separation.

In one or more embodiments of the above aspects, the ratio b/c is about 0.05-75, 0.05-50, 0.1, 0.2, 0.3, 0.4, 0.5, 0.6, 0.7, 0.8, 0.9, 1, 5, 10, 15, 20, 25, 30, 35, 40, 45, 50, 60, 70, 80, or 90. In some embodiments, the surface of X does not include silica, and b=0 or c=0. In some embodiments, the combined surface coverage is greater than about 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.4, 3.5, 3.6, 3.7, 3.8, 3.9, 4, 5, 6, 7, or 8 $\mu mol/m^2$.

In some embodiments of the above aspects, the chromatographic stationary phase exhibits a retention drift or change of ≤5% over 30 days, ≤4% over 30 days, ≤3% over 30 days, ≤2% over 30 days, ≤1% over 30 days, ≤5% over 10 days, ≤4% over 10 days, ≤3% over 10 days, ≤2% over 10 days, ≤1% over 10 days, ≤5% over 3 days, ≤4% over 3 days, ≤3% over 3 days, ≤2% over 3 days, ≤1% over 3 days, ≤5% over 30 runs, ≤4% over 30 runs, ≤3% over 30 runs, ≤2% over 30 runs, ≤1% over 30 runs, ≤5% over 10 runs, ≤4% over 10 runs, ≤3% over 10 runs, ≤2% over 10 runs, ≤1% over 10 runs, ≤5% over 3 runs, ≤4% over 3 runs, ≤3% over 3 runs, ≤2% over 3 runs, or ≤1% over 3 runs.

In some embodiments, the core material consists essentially of a silica material. Optionally, the core material consists essentially of an organic-inorganic hybrid material or a superficially porous material. In one or more embodiments, the core material consists essentially of an inorganic material with a hybrid surface layer, a hybrid material with an inorganic surface layer, a surrounded hybrid layer, or a hybrid material with a different hybrid surface layer. The stationary phase material can optionally be in the form of a plurality of particles, a monolith, or a superficially porous material. In some embodiments the stationary phase material does not have chromatographically enhancing pore geometry whereas in other embodiments the stationary phase material has chromatographically enhancing pore geometry. The stationary phase material can be in the form of a spherical material, non-spherical material (e.g., including toroids, polyhedrons). In certain embodiments, the stationary phase material has a highly spherical core morphology, a rod shaped core morphology, a bent-rod shaped core morphology, a toroid shaped core morphology; or a dumbbell shaped core morphology. In certain embodiments, the stationary phase material has a mixture of highly spherical, rod shaped, bent rod shaped, toroid shaped, or dumbbell shaped morphologies.

In some embodiments, the stationary phase material has a surface area of about 25 to 1100 $m^2/g$, about 150 to 750 $m^2/g$, or about 300 to 500 $m^2/g$. In some embodiments, the stationary phase material has a pore volume of about 0.2 to 2.0 $cm^3/g$, or about 0.7 to 1.5 $cm^3/g$. In some embodiments, the stationary phase material has a micropore surface area of less than about 105 $m^2/g$, less than about 80 $m^2/g$, or less than about 50 $m^2/g$. The stationary phase material can have an average pore diameter of about 20 to 1500 Å, about 50 to 1000 Å, about 60 to 750 Å, or about 65 to 200 Å. In some embodiments, the plurality of particles have sizes between about 0.2 and 100 microns, between about 0.5 and 10 microns, or between about 1.5 and 5 microns.

In one or more embodiments, X includes a silica core, c=0, and Q has a combined surface coverage of ≥2.5, 2.6, 2.7, 2.8, 2.9, 3.0, 3.5, 4.0, 4.5, or 5 $\mu mol/m^2$; or X includes a non-silica core or a silica-organic hybrid core, c=0, and Q has a combined surface coverage of ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, or 5 $\mu mol/m^2$; or b>0, c>0, and Q has a combined surface coverage of ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, or 5 $\mu mol/m^2$.

In other embodiments, Q has a combined surface coverage of ≥0.5, 0.6, 0.7, 0.8, 0.9, 1.0, 1.1, 1.2, 1.3, 1.4, 1.5, 1.6, 1.7, 1.8, 1.9, or 2.0 $\mu mol/m^2$. In other embodiments, T has a combined surface coverage of ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0 or 3.5 $\mu mol/m^2$. T can also have a combined surface coverage between about 0.1 and about 4.0 $\mu mol/m^2$, or about 0.2 and about 3.9 $\mu mol/m^2$, or about 0.3 and about 3.8 $\mu mol/m^2$, or about 0.4 and about 3.7 $\mu mol/m^2$, or about 0.5 and about 3.6 $\mu mol/m^2$, or about 1.0 and about 3.5 $\mu mol/m^2$, or about 1.2 and about 3.0 $\mu mol/m^2$, or any combination of values, such as between about 3.0 and about 4.0 $\mu mol/m^2$.

In other embodiments, the overall combined coverage of Q and T is ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.5, 6.0 or 6.5 $\mu mol/m^2$.

The chromatographic stationary phase can be adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography.

The chromatographic stationary phase can include radially adjusted pores, non-radially adjusted pores, ordered pores, non-ordered pores, monodispersed pores, non-monodispersed pores, smooth surfaces, rough surfaces or combinations thereof. In one or more embodiments, T has one ionizable group, T has more than one ionizable group, T has two or more ionizable groups of the same pKa, or T has two or more ionizable group of different pKa.

In another embodiment, the present disclosure relates to a chromatographic stationary phase having the following structure (i):

  (i)

wherein X is a chromatographic substrate containing silica, metal oxide, an inorganic-organic hybrid material, a group of block copolymers, or combinations thereof; W is selected from the group consisting of hydrogen and hydroxyl, wherein W is bound to the surface of X; Q is a first substituent which minimizes analyte retention variation over time under chromatographic conditions having low water concentrations; T is a second substituent which chromatographically retains the analyte, wherein T has one or more aromatic, polyaromatic, heterocyclic aromatic, or polyheterocyclic aromatic hydrocarbon groups, each group being optionally substituted with an aliphatic group; and b and c are positive numbers, $0.05 \leq (b/c) \leq 100$, and $a \geq 0$.

In another embodiment, the present disclosure relates to a column, capillary column, microfluidic device or apparatus for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography comprising a housing having at least one wall defining a chamber having an entrance and an exit, and a stationary phase as described in the present disclosure disposed therein, wherein the housing and stationary phase are adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography.

In another embodiment, the present disclosure relates to a kit for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography comprising a housing having at least one wall defining a chamber having an entrance and an exit, and a stationary phase as described in the present disclosure disposed therein, wherein the housing and stationary phase are adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography; and instructions for performing normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography with the housing and stationary phase.

The kit can include a housing having at least one wall defining a chamber having an entrance and an exit, and a stationary phase according to any embodiments of the present disclosure disposed therein. The devices can have preformed frits, frits generated by interconnected materials, or devices without frits. The housing and stationary phase can be adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof. Additionally, instructions for performing normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof with the housing and stationary phase can be included.

Accordingly, the kit of the present disclosure can be used to implement the methods of the invention described herein. Additionally, the kits of the present invention can be used to analyze a variety of different samples and sample types, including those described herein below.

In one or more embodiments, the present invention can contemplate kits containing aspects of the present disclosure to reduce or mitigate the effects of retention drift or change. For instance, a kit can contain a chromatography column packed with a stationary phase media of the present disclosure. In some embodiments the packed column can be used directly in a standard chromatography system (e.g., a commercially available chromatography system such as a Waters Acquity® chromatography system). A kit can further contain instruction for use. Additionally, a kit can further contain stock samples of pure analyte for calibration of the instrument and/or confirmation of a substantial lack of retention drift or change. A kit can include any or all of the components described above (e.g., a stationary phase, a packed column, or a chromatography apparatus) to mitigate the effects of retention drift or change.

In another embodiment, the present disclosure relates to a method for mitigating or preventing retention drift in normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography comprising chromatographically separating a sample using a chromatographic device comprising a chromatographic stationary phase as described in the present disclosure, thereby mitigating or preventing retention drift.

In one or more embodiments, mitigating or preventing retention drift or change includes a retention drift or change of $\geq 5\%$ over 30 days, $\geq 4\%$ over 30 days, $\geq 3\%$ over 30 days, $\geq 2\%$ over 30 days, $\geq 1\%$ over 30 days, $\geq 5\%$ over 10 days, $\geq 4\%$ over 10 days, $\geq 3\%$ over 10 days, $\geq 2\%$ over 10 days, $\geq 1\%$ over 10 days, $\geq 5\%$ over 3 days, $\geq 4\%$ over 3 days, $\geq 3\%$ over 3 days, $\geq 2\%$ over 3 days, $\geq 1\%$ over 3 days, $\geq 5\%$ over 30 runs, $\geq 4\%$ over 30 runs, $\geq 3\%$ over 30 runs, $\geq 2\%$ over 30 runs, $\geq 1\%$ over 30 runs, $\geq 5\%$ over 10 runs, $\geq 4\%$ over 10 runs, $\geq 3\%$ over 10 runs, $\geq 2\%$ over 10 runs, $\geq 1\%$ over 10 runs, $\geq 5\%$ over 3 runs, $\geq 4\%$ over 3 runs, $\geq 3\%$ over 3 runs, $\geq 2\%$ over 3 runs, or $\geq 1\%$ over 3 runs. In some embodiments, mitigating or preventing retention drift or change includes substantially eliminating the effect of alkoxylation and/or dealkoxylation of the chromatographic material on retention.

The concept of chemically modifying chromatographic core materials, as used herein, is understood to include functionalizing a chromatographic core, for example with a polar silane, or other functional group, thereby mitigating or avoiding retention drift or change. For example, functionalization can essentially prevent chromatographic interaction between an analyte and the chromatographic core (e.g., effectively eliminating a chromatographic effect of core surface silanols and/or alkoxylated silanols). In some cases, functionalization (e.g., using non-polar groups) can reduce the retentivity of the column. Therefore, in various embodiments functionalization of chromatographic core materials can include the use of hydrophilic, polar, ionizable, and/or charged functional group that chromatographically interacts with the analyte, to preserve or achieve a chromatographically useful overall retention. Such endcapping groups can be introduced, for example, via standard bonding chemistry.

In some embodiments, functionalization provides a permanent attachment. Accordingly, it is important to select an appropriate functionalization for the chromatographic phase. In preferred embodiments, the chromatographic material will have chromatographically desirable properties (e.g., overall retention). Therefore in some embodiments it is important to select a functionalization that has properties that can mimic the desirable (e.g., overall retention) properties of a conventional chromatographic material.

In various embodiments, the chemical properties of a functional group can be selected to achieve a desired effect. For example, one or more hydrophilic, polar, ionizable, and/or charged functional group can be used to achieve desired interactions with an analyte (e.g., chromatographically acceptable retention) and/or the mobile phase (e.g., repelling alcohols that might alkoxylate a chromatographic core surface). Likewise, endcap size and/or sterics can be selected to mask a core surface and/or effect a chiral separation.

Similarly, the concentration of functionalization can be varied. In some embodiments, larger and/or more strongly interacting functional groups can mitigate or avoid retention drift or change at lower concentrations (e.g., as compared to smaller functional groups). In other embodiments, coverage can be tailored for a desired property. For example, nonpolar functional groups can be used at lower coverage than polar functional groups (e.g., to maintain a desired retention). In various embodiments, functionalization can use one or more polar or nonpolar endcaps, or a combination thereof. In some embodiments, surface area of the chromatographic media is increased or decreased to compensate for decreased or increased retention due to the altered polarity of the functional groups.

In another embodiment, the present disclosure relates to a method for preparing a stationary phase as described in the present disclosure comprising reacting a chromatographic substrate with a silane coupling agent having a pendant reactive group; reacting a second chemical agent comprising one or more aromatic, polyaromatic, heterocyclic aromatic, or polyheterocyclic aromatic hydrocarbon groups with the pendant reactive group; and neutralize any remaining unreacted pendant reactive groups, thereby producing the stationary phase.

In another embodiment, the present disclosure relates to a method for preparing a stationary phase as described in the present disclosure comprising oligomerizing a silane coupling agent having a pendant reactive group; reacting a core surface with the oligomerized silane coupling agent; reacting a second chemical agent comprising one or more aromatic, polyaromatic, heterocyclic aromatic, or polyheterocyclic aromatic hydrocarbon groups with the pendant reactive group; and neutralize any remaining unreacted pendant reactive groups, thereby producing the stationary phase.

In one or more embodiments, Q is derived from a reagent having one of the following structures:

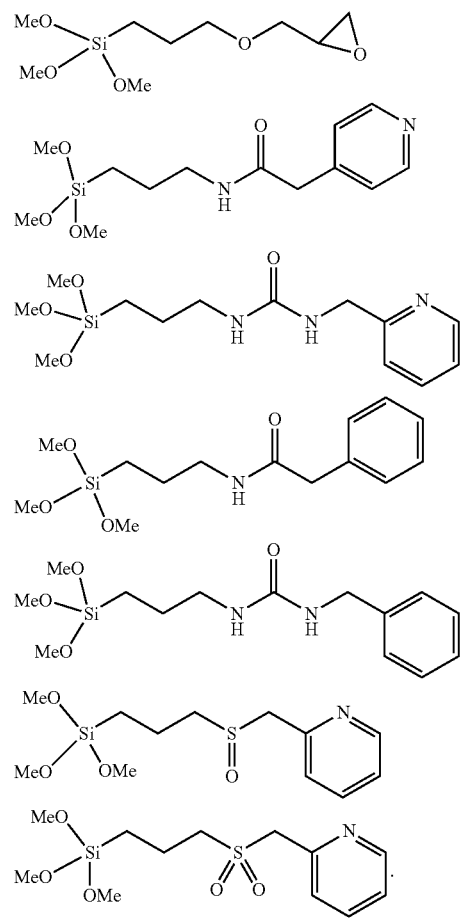

In some embodiments, Y includes one of the following structures:

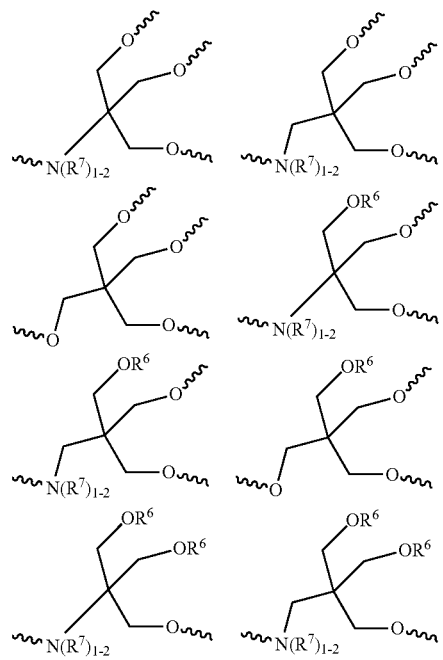

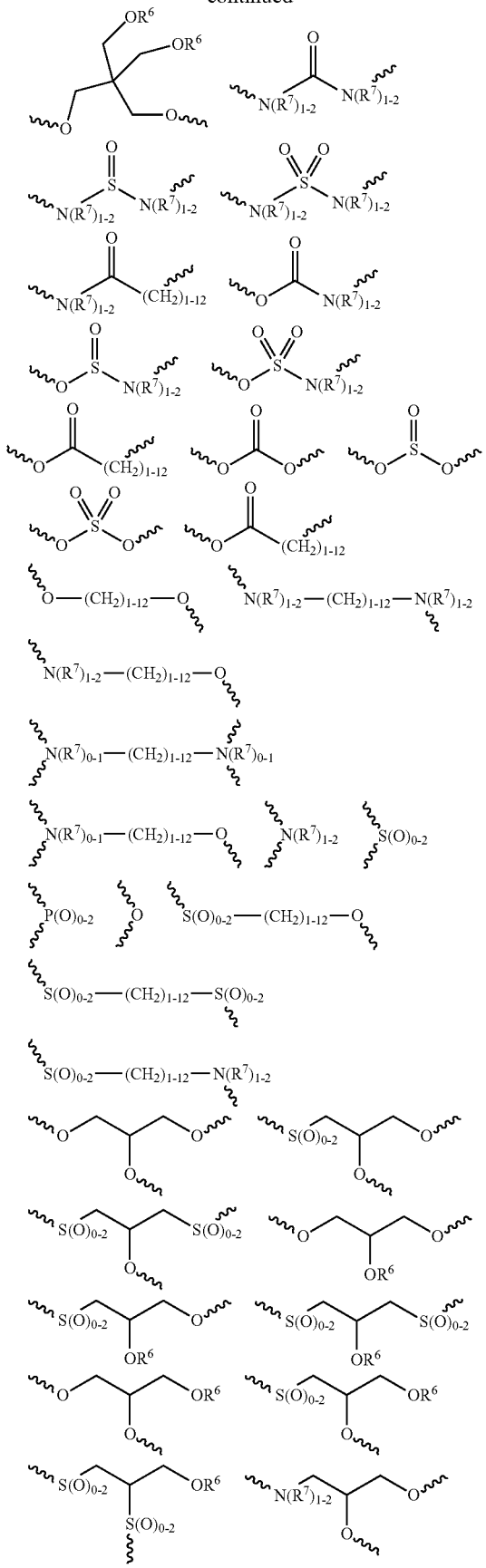

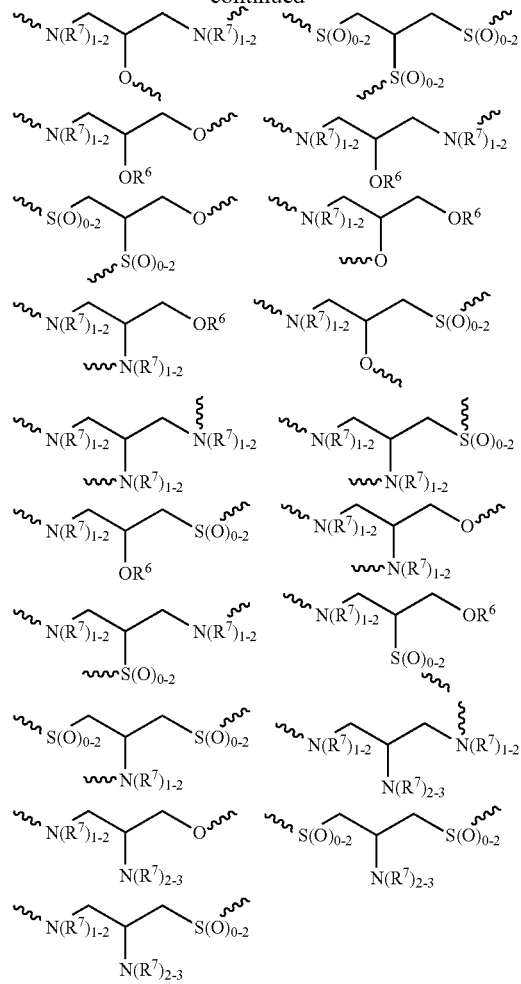

wherein the $R^6$ and $R^7$ groups associated with the Y group each individually is an aliphatic group. In some embodiment, the Y group may also be a bond or an aliphatic group.

The above method can be used to make any of the materials (e.g., chromatography stationary phase materials) as described herein. For instance, the methods of the present disclosure can include methods of reacting a chromatographic stationary phase (e.g., silica particles) with a chemical reagent (e.g., any of the above reagents as described herein) to chemically modify the surface of the stationary phase to mitigate the effects of retention drift or change.

The present disclosure includes various apparatuses (e.g., chromatographic columns, capillary and microfluidic devices, and systems for use thereof) including the chromatographic materials described herein. While several illustrative examples are discussed below, a practitioner of ordinary skill will understand that the present disclosure can contemplate a number of different embodiments, including but not limited to chromatographic columns, apparatuses, methods of use, or kits.

In some embodiments, the present disclosure provides a column or apparatus for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof. The column or apparatus includes a housing having at least one wall defining a chamber having an entrance and an exit, as well as a stationary phase according to any embodiments of the present disclosure disposed therein. The devices can have preformed frits, frits generated by interconnected materials, or devices without frits. The housing and stationary phase can be adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof.

Accordingly, the apparatus of the present disclosure can contain (e.g., be packed with) materials of the present disclosure (e.g., a chromatographic stationary phase such as a chemically modified stationary phase adapted to reduce or mitigate retention drift or change). Moreover, the apparatus of the present disclosure can be used to carry out the methods of the present disclosure as described herein.

In one embodiment, the present disclosure is in the form a packed column. The column can be packed with a stationary phase (e.g., chromatographic material) described herein. Such a column can be used to perform different types of chromatography (e.g., normal phase chromatography, supercritical fluid chromatography, carbon dioxide based chromatography, hydrophobic interaction liquid chromatography, hydrophilic interaction liquid chromatography, sub-critical fluid chromatography, high pressure liquid chromatography, and solvated gas chromatography) while mitigating or avoiding retention drift or change.

The columns can be used in combination with existing chromatography platforms such as commercially available chromatography systems, including the Waters Alliance® HPLC system, Waters Acquity® system, or Waters UPC$^2$® system. A column of the present disclosure can be used for a number of different mass throughputs (e.g., analytical scale chromatography, preparative scale chromatography) while mitigating the effects of retention drift or change. Likewise, the present disclosure can be embodies in capillary and microfluidic devices, and systems (e.g., commercially available and know to persons of ordinary skill in the art) for use thereof. The selection of columns, capillary, and microfluidic devices, and related systems will be readily understandable to person of ordinary skill in the art.

In various embodiments, material in accordance with the present disclosure can have application in microbore columns for use on a SFC, HPLC, and/or UHPLC system. In various embodiments, material in accordance with the present disclosure can have application fast equilibration columns, long lifetime columns, and SFC with water stable columns.

The present disclosure can be used to retain, separate and/or analyze a plurality of different compounds of interest from many different samples from many different fields, for example, from clinical chemistry, medicine, veterinary medicine, forensic chemistry, pharmacology, food industry, safety at work, and environmental pollution. The plurality of samples including, but are not limited to, small organic molecules, proteins, nucleic acids, lipids, fatty acids, carbohydrates, polymers, and the like. Similarly, the present disclosure can be used for the separation of small molecules, polar small molecules, analytes used in pharmaceuticals, biomolecules, antibodies, polymers and oligomers, sugars, glycan analysis, petrochemical analysis, lipid analysis, peptides, phosphopeptides, oligonucleotides, DNA, RNA, polar acids, polyaromatic hydrocarbons, food analysis, chemical analysis, bioanalysis, drugs of abuse, forensics, pesticides, agrochemicals, biosimilars, formulations.

Analytes amenable to chromatographic separation with the present disclosure can include essentially any molecule of interest, including, for example, small organic molecules, lipids, peptides, nucleic acids, synthetic polymers.

Clinical chemistry target analytes can include any molecule present in an organism (e.g., human body, animal body, fungi, bacterium, virus, and the like). For example, clinical chemistry target analytes include, but are not limited to, proteins, metabolites, biomarkers, and drugs.

Human medicine and veterinary medicine target analytes can include any molecule that can be used for the diagnosis, prophylaxis or treatment of a disease or condition in a subject. For example, human medicine and veterinary medicine target analytes include, but are not limited to, disease markers, prophylactic agents, or therapeutic agents.

Forensic chemistry target analytes can include any molecule present in a sample taken from the site of crime, such as a sample from a victim's body (e.g., tissue or fluid sample, hair, blood, semen, urine, and the like). For example, clinical chemistry target analytes include, but are not limited to, toxic agents, drugs and their metabolites, biomarkers, and identifying compounds.

Pharmacology target analytes can include any molecule that is a pharmaceutical or metabolite thereof or which can be used for the design, synthesis, and monitoring of drugs. For example, pharmacology target analytes include, but are not limited to, prophylactic and/or therapeutic agents, their prodrugs, intermediates and metabolites. Pharmacological analysis can include bioequivalence testing, for example, in connection with the approval, manufacturing, and monitoring of a generic drug.

Food industry and agricultural target analytes can include any molecule that is relevant for monitoring of the safety of foods, beverages, and/or other food industry/agricultural products. Examples of target analytes from the field of food industry include, but are not limited to, pathogen markers, allergens (e.g., gluten and nut proteins), and mycotoxins.

Target analytes can include polypeptides (e.g., polymers of naturally and/or non-naturally occurring amino acids such as Gly, Ala, Val, Leu, Ile, Pro, Phe, Trp, Cys, Met, Ser, Thr, Tyr, His, Lys, Arg, Asp, Glu, Asn, Gln, selenocysteine, ornithine, citrulline, hydroxyproline, methyllysine, carboxyglutamate), peptides, proteins, glycoproteins, lipoproteins; peptide-nucleic acids; hormones (such as peptide hormones (e.g., TRH and vasopressin), as well as synthetic and industrial polypeptides.

In some embodiments, the compound of interest is a saturated or an unsaturated lipid, vitamin or polycyclic aromatic hydrocarbon. The term "saturated" as used herein refers to constituents that contain no double bond in the acyl site of the molecule. The term "saturated lipid" as used herein refers to constituents of fats and oils that contain no double bond in the acyl chain sites of the molecule. The term "unsaturated" as used herein refers to constituents that contain one or more sites of unsaturation in the molecule. The term "unsaturated lipid" as used herein refers to constituents of fats and oils that contain one or more sites of unsaturation in the molecule. These may occur in the fatty acid portions of the molecule such as in triglycerides, phospholipids and glycolipids, or in alkyl chains in the molecule, such as in carotenoids, hydrocarbons and fat soluble vitamins. The lipid can be selected from the group consisting of saturated and unsaturated fatty acids, phospholipids, glycerolipids, glycerophospholipids, lysophosphoglycerolipids, sphingolipids, sterol lipids, prenol lipids, saccharolipids, carotenoids, waxes, and polyketides.

In another embodiment, the present disclosure can be used to retain, separate and resolve polycyclic aromatic hydrocarbon and related compounds. Polycyclic aromatic hydrocarbons (PAHs) form a family of non-functionalised aromatic compounds composed of fused aromatic rings. There are about 2000 compounds classed as PAHs. PAHs and their derivatives are widespread in the environment as a result of combustion processes, such as burning fossil fuels. They bind strongly to soil organic matter (humic acids) and their rate of degradation in soil and other environmental compartments is usually slow. In addition, PAHs reaching watercourses are rapidly transferred to sediment.

PAHs are also formed during domestic and industrial combustion processes such as extracting vegetable oils, herbs, spices and other food materials, smoking and grilling food materials and the like. PAHs are toxic and carcinogenic compounds. The control of their presence and levels is of growing importance in the context of food safety and health and safety regulations. Several of the effects of PAHs are enzyme induction, immunosuppression, teratogenecity, and tumour promotion.

In particular embodiments, the lipid can be saturated or an unsaturated fatty acid, monoacylglyceride, diacylglyceride, triacylglyceride, phospholipid or steroid. A triglyceride (TG, triacylglycerol, TAG, or triacylglyceride) is an ester derived from glycerol and three fatty acids. As a blood lipid, they help enable the bidirectional transference of adipose fat and blood glucose from the liver. There are many triglycerides: depending on the oil source, some are highly unsaturated, some less so. Triglycerides are the main constituents of vegetable oil (typically more unsaturated) and animal fats (typically more saturated). Triglycerides are a major component of human skin oils.

A steroid is a type of organic compound that contains a characteristic arrangement of four cycloalkane rings that are joined to each other. Examples of steroids include the dietary lipid cholesterol, the sex hormones estradiol and testosterone and the anti-inflammatory drug dexamethasone. The core of steroids is composed of seventeen carbon atoms bonded together that take the form of four fused rings: three cyclohexane rings and one cyclopentane ring. The steroids vary by the functional groups attached to this four-ring core and by the oxidation state of the rings. Sterols are special forms of steroids, with a hydroxyl group at position-3 and a skeleton derived from cholestane.

Hundreds of distinct steroids are found in plants, animals and fungi. All steroids are made in cells either from the sterols lanosterol (animals and fungi) or from cycloartenol (plants). Both lanosterol and cycloartenol are derived from the cyclization of the triterpene squalene.

In other embodiments, the compound of interest can be a fat soluble vitamin selected from the group consisting of a vitamin C, vitamin B, or derivatives or combinations thereof. Fat-soluble vitamins are of interest because they are difficult to dissolve, often strong organic solvents are necessary and separation via RPLC. Typically, fat-soluble vitamins are separated using SFC conditions by the use of C18 silanes (ODS) or other alkyl bonded phases. These methods often utilize very weak co-solvents and very high percentages of $CO_2$ in the mobile phase. One of the advantages of the present disclosure is the stationary phase is modified with a pi-electron rich selector, e.g. 1-aminoanthracene. Coupling a pi-electron rich selector to the stationary phase maximizes the chromatographic selectively between two critical pairs, such as vitamins D2 and D3, or K1 and K2.

Another advantage of the present disclosure is the stationary phases have selector with a relatively high pKa such that no acid or basic additives are necessary to accomplish the separation. In one embodiment, the present disclosure relates to methodology utilizing a mobile phase with no acid additive, basic additive, or both. In other embodiments, the present disclosure relates to methodology utilizing a mobile phase with less than 5.0%, or 4.0%, or 3.0%, or 2.0%, 1.0%, or 0.5%, or 0.2%, or 0.1%, or 0.05% of an acid additive, basic additive, or both. Using only carbon dioxide modified with methanol as the co-solvent, a fast, generic, method can be created. For example, the separation of the afore-mentioned vitamin critical pairs is achieved using the stationary phase of the present disclosure having, for example, 1-aminoanthracene as the selector. In one embodiment, the level of resolution between critical pairs of Vitamins is higher than current methodology (resolution per same column length; use of sub-2 µm particles and 50 mm column length).

The present disclosure can be used to retain, separate and resolve Vitamin C and related compounds. Vitamin C [2-oxo-L-threo-hexono-1,4-lactone2,3-enediol] or L-ascorbic acid is a water-soluble vitamin and essential nutrient for humans. It is essential in the formation of collagen, which is required for normal growth and development as well as tissue repair in all parts of the body. Vitamin C also functions as an antioxidant that blocks the damage caused by free radicals and directly reduces toxic chemicals and pollutants.

As humans do not produce vitamin C in the body, it is primarily obtained from dietary sources such as fruits and vegetables. Lack of dietary vitamin C may result in vitamin C deficiency. Severe vitamin C deficiency, also know as "scurvy," leads to the formation of liver spots on skin, spongy gums, and bleeding from mucous membranes, or even death.

Currently, vitamin C is not only used as a dietary supplement, but also as an adjunct therapy for some viral infections and terminal cancers. The recommended daily intake of vitamin C for adults to prevent deficiency is 75 mg for females and 90 mg for males, both with a tolerable upper level of 2,000 mg. For therapeutic usage in detoxification and cancer therapy, vitamin C is given intravenously at much higher doses. Although vitamin C toxicity is rare clinically, relatively high doses of oral intake may lead to stomach upset and diarrhea. Assays for vitamin C blood levels have been developed and are used by patients and physicians to evaluate nutritional status or to optimize therapeutic dosages. Measurement of these compounds are useful indices of vitamin C nutritional status and the efficacy of certain vitamin C analogs.

In another embodiment, the present disclosure can be used to retain, separate and resolve Vitamin B and related compounds. B vitamins are a group of water-soluble vitamins that play important roles in cell metabolism. The B vitamins were once thought to be a single vitamin, referred to simply as vitamin B. Later research showed that they are chemically distinct vitamins that often coexist in the same foods. In general, supplements containing all eight are referred to as a vitamin B complex. Individual B vitamin supplements are referred to by the specific name of each vitamin (e.g., B1, B2, B3 etc.). A list of B vitamins includes: Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), Vitamin B12 (various cobalamins; commonly cyanocobalamin in vitamin supplements).

The roles of the Vitamin B compound differ. For example, thiamine plays a central role in the generation of energy from carbohydrates. It is involved in RNA and DNA production, as well as nerve function. Its active form is a coenzyme called Thiamine pyrophosphate (TPP), which takes part in the conversion of pyruvate to acetyl Coenzyme A (CoA) in metabolism. Riboflavin is involved in the energy production for the electron transport chain, the citric acid cycle, as well as the catabolism of fatty acids (beta oxidation). Niacin is composed of two structures: nicotinic acid and nicotinamide. There are two co-enzyme forms of niacin: nicotinamide adenine dinucleotide (NAD) and nicotinamide adenine dinucleotide phosphate (NADP). Both play an important role in energy transfer reactions in the metabolism of glucose, fat and alcohol. NAD carries hydrogens and their electrons during metabolic reactions, including the pathway from the citric acid cycle to the electron transport chain. NADP is a coenzyme in lipid and nucleic acid synthesis.

Pantothenic acid is involved in the oxidation of fatty acids and carbohydrates. Coenzyme A, which can be synthesised from pantothenic acid, is involved in the synthesis of amino acids, fatty acids, ketones, cholesterol, phospholipids, steroid hormones, neurotransmitters (such as acetylcholine), and antibodies. Pyridoxine is usually stored in the body as pyridoxal 5'-phosphate (PLP), which is the co-enzyme form of vitamin B6. Pyridoxine is involved in the metabolism of amino acids and lipids; in the synthesis of neurotransmitters and hemoglobin, as well as in the production of nicotinic acid (vitamin B3). Pyridoxine also plays an important role in gluconeogenesis. Biotin plays a key role in the metabolism of lipids, proteins and carbohydrates. It is a critical co-enzyme of four carboxylases: acetyl CoA carboxylase, which is involved in the synthesis of fatty acids from acetate; propionyl CoA carboxylase, involved in gluconeogenesis; β-methylcrotonyl Coa carboxylase, involved in the metabolism of leucin; and pyruvate CoA carboxylase, which is involved in the metabolism of energy, amino acids and cholesterol.

Folic acid acts as a co-enzyme in the form of tetrahydrofolate (THF), which is involved in the transfer of single-carbon units in the metabolism of nucleic acids and amino acids. THF is involved in pyrimidine nucleotide synthesis, so is needed for normal cell division, especially during pregnancy and infancy, which are times of rapid growth. Folate also aids in erythropoiesis, the production of red blood cells. Vitamin B12 is involved in the cellular metabolism of carbohydrates, proteins and lipids. It is essential in the production of blood cells in bone marrow, nerve sheaths and proteins. Vitamin B12 functions as a co-enzyme in intermediary metabolism for the methionine synthase reaction with methylcobalamin, and the methylmalonyl CoA mutase reaction with adenosylcobalamin.

The impact of any deficiency in these vitamins also differs. Vitamin B1 thiamine Deficiency causes beriberi. Symptoms of this disease of the nervous system include weight loss, emotional disturbances, Wernicke's encephalopathy (impaired sensory perception), weakness and pain in the limbs, periods of irregular heartbeat, and edema (swelling of bodily tissues). Heart failure and death may occur in advanced cases. Chronic thiamine deficiency can also cause Korsakoff's syndrome, an irreversible dementia characterized by amnesia and compensatory confabulation.

Vitamin B2 riboflavin Deficiency causes ariboflavinosis. Symptoms may include cheilosis (cracks in the lips), high sensitivity to sunlight, angular cheilitis, glossitis (inflammation of the tongue), seborrheic dermatitis or pseudo-syphilis (particularly affecting the scrotum or labia majora and the mouth), pharyngitis (sore throat), hyperemia, and edema of the pharyngeal and oral mucosa.

Vitamin B3 niacin Deficiency, along with a deficiency of tryptophan causes pellagra. Symptoms include aggression, dermatitis, insomnia, weakness, mental confusion, and diarrhea. In advanced cases, pellagra may lead to dementia and death (the 3(+1) Ds: dermatitis, diarrhea, dementia, and death).

Vitamin B5 pantothenic acid Deficiency can result in acne and paresthesia, although it is uncommon. Vitamin B6 pyridoxine Deficiency may lead to microcytic anemia (because pyridoxyl phosphate is the cofactor for heme synthesis), depression, dermatitis, high blood pressure (hypertension), water retention, and elevated levels of homocysteine. Vitamin B7 biotin Deficiency does not typically cause symptoms in adults but may lead to impaired growth and neurological disorders in infants. Multiple carboxylase deficiency, an inborn error of metabolism, can lead to biotin deficiency even when dietary biotin intake is normal.

Vitamin B9 folic acid Deficiency results in a macrocytic anemia, and elevated levels of homocysteine. Deficiency in pregnant women can lead to birth defects. Supplementation is often recommended during pregnancy. Researchers have shown that folic acid might also slow the insidious effects of age on the brain. Vitamin B12 cobalamin Deficiency results in a macrocytic anemia, elevated homocysteine, peripheral neuropathy, memory loss and other cognitive deficits. It is most likely to occur among elderly people, as absorption through the gut declines with age; the autoimmune disease pernicious anemia is another common cause. It can also cause symptoms of mania and psychosis. In rare extreme cases, paralysis can result. Measurement of these compounds are useful indices of vitamin B nutritional status and the efficacy of certain vitamin B analogs.

In other embodiments, the compound of interest can be a fat soluble vitamin selected from the group consisting of a vitamin D, vitamin A, vitamin K, vitamin E, betacarotene, or derivatives or combinations thereof. The present disclosure can be used to retain, separate and resolve Vitamin D and related compounds. Vitamin D is an essential nutrient with important physiological roles in the positive regulation of calcium homeostasis. Vitamin D can be made de novo in the skin by exposure to sunlight or it can be absorbed from the diet. There are two forms of vitamin D; vitamin D2 (ergo calciferol) and vitamin D3 (cholecalciferol). Vitamin D3 is the form synthesized de novo by animals. It is also a common supplement added to milk products and certain food products produced in the United States. Both dietary and intrinsically synthesized vitamin D3 must undergo metabolic activation to generate the bioactive metabolites. In humans, the initial step of vitamin D3 activation occurs primarily in the liver and involves hydroxylation to form the intermediate metabolite 25-hydroxycholecalciferol (calcifediol), which is enzymatically hydroxylated at the 25 position. Calcifediol is the major form of Vitamin D3 in the circulation. Circulating calcifediol is then converted by the kidney to form 1,25-dihydroxyvitamin D3 (calcitriol), which is generally believed to be the metabolite of Vitamin D3 with the highest biological activity. Vitamin D2 is derived from fungal and plant sources. Many over-the-counter dietary supplements contain ergocalciferol (vitamin D2) rather than cholecalciferol (vitamin D3). Drisdol, the only high-potency prescription form of vitamin D available in the United States, is formulated with ergocalciferol. Vitamin D2 undergoes a similar pathway of metabolic activation in humans as vitamin D3, forming the metabolites calcifediol and calcitriol. Vitamin D2 and vitamin D3 have long been assumed to be biologically equivalent in humans, however recent reports suggest that there may be differences in the bioactivity and bioavailability of these two forms of vitamin D. Measurement of these compounds are useful indices of vitamin D nutritional status and the efficacy of certain vitamin D analogs.

In another embodiment, the present disclosure can be used to retain, separate and resolve Vitamin A and related compounds. Vitamin A is a group of unsaturated nutritional organic compounds, that includes retinol, retinal, retinoic acid, and several provitamin A carotenoids, among which beta-carotene is the most important. Vitamin A has multiple functions: it is important for growth and development, for the maintenance of the immune system and good vision. Vitamin A is needed by the retina of the eye in the form of retinal, which combines with protein opsin to form rhodopsin the light-absorbing molecule, that is necessary for both low-light (scotopic vision) and color vision. Vitamin A also functions in a very different role as an irreversibly oxidized form of retinol known as retinoic acid, which is an important hormone-like growth factor for epithelial and other cells.

In foods of animal origin, the major form of vitamin A is an ester, primarily retinyl palmitate, which is converted to retinol (chemically an alcohol) in the small intestine. The retinol form functions as a storage form of the vitamin, and can be converted to and from its visually active aldehyde form, retinal. The associated acid (retinoic acid), a metabolite that can be irreversibly synthesized from vitamin A, has only partial vitamin A activity, and does not function in the retina for the visual cycle. Retinoic acid is used for growth and cellular differentiation.

All forms of vitamin A have a beta-ionone ring to which an isoprenoid chain is attached, called a retinyl group. Both structural features are essential for vitamin activity. The orange pigment of carrots—beta-carotene—can be represented as two connected retinyl groups, which are used in the body to contribute to vitamin A levels. Alpha-carotene and gamma-carotene also have a single retinyl group, which give them some vitamin activity.

Vitamin A can be found in two principal forms in foods: (i) Retinol, the form of vitamin A absorbed when eating animal food sources, is a yellow, fat-soluble substance. Since the pure alcohol form is unstable, the vitamin is found in tissues in a form of retinyl ester. It is also commercially produced and administered as esters such as retinyl acetate or palmitate. (ii) The carotenes alpha-carotene, beta-carotene, gamma-carotene; and the xanthophyll beta-cryptoxanthin (all of which contain beta-ionone rings), but no other carotenoids, function as provitamin A in herbivores and omnivore animals, which possess the enzyme (15-15'-dioxygenase) which cleaves beta-carotene in the intestinal mucosa and converts it to retinol. In general, carnivores are poor converters of ionone-containing carotenoids, and pure carnivores such as cats and ferrets lack 15-15'-dioxygenase and cannot convert any carotenoids to retinal (resulting in none of the carotenoids being forms of vitamin A for these species). Measurement of these compounds are useful indices of vitamin A nutritional status and the efficacy of certain vitamin A analogs.

In another embodiment, the present disclosure can be used to retain, separate and resolve Vitamin K and related compounds. Vitamin K is a group of structurally similar, fat-soluble vitamins that the human body needs for post-translational modification of certain proteins required for blood coagulation, and in metabolic pathways in bone and other tissue. They are 2-methyl-1,4-naphthoquinone (3-) derivatives. This group of vitamins includes two natural vitamers: vitamin K1 and vitamin K2.

Vitamin K1, also known as phylloquinone, phytomenadione, or phytonadione, is synthesized by plants, and is found in highest amounts in green leafy vegetables because it is directly involved in photosynthesis. It may be thought of as the "plant form" of vitamin K. It is active in animals and may perform the classic functions of vitamin K in animals, including its activity in the production of blood-clotting proteins. Animals may also convert it to vitamin K2.

Vitamin K2, the main storage form in animals, has several subtypes, which differ in isoprenoid chain length. These vitamin K2 homologues are called menaquinones, and are characterized by the number of isoprenoid residues in their side chains. Menaquinones are abbreviated MK-n, where M stands for menaquinone, the K stands for vitamin K, and the n represents the number of isoprenoid side chain residues. For example, menaquinone-4 (abbreviated MK-4) has four isoprene residues in its side chain. Menaquinone-4 (also known as menatetrenone from its four isoprene residues) is the most common type of vitamin K2 in animal products since MK-4 is normally synthesized from vitamin K1 in certain animal tissues (arterial walls, pancreas, and testes) by replacement of the phytyl tail with an unsaturated geranylgeranyl tail containing four isoprene units, thus yielding menaquinone-4. This homolog of vitamin K2 may have enzyme functions that are distinct from those of vitamin K1.

Bacteria in the colon (large intestine) can also convert K1 into vitamin K2. In addition, bacteria typically lengthen the isopreneoid side chain of vitamin K2 to produce a range of vitamin K2 forms, most notably the MK-7 to MK-11 homologues of vitamin K2. All forms of K2 other than MK-4 can only be produced by bacteria, which use these forms in anaerobic respiration. The MK-7 and other bacteria-derived form of vitamin K2 exhibit vitamin K activity in animals, but MK-7's extra utility over MK-4, if any, is unclear and is presently a matter of investigation.

Three synthetic types of vitamin K are known: vitamins K3, K4, and K5. Although the natural K1 and all K2 homologues have proven nontoxic, the synthetic form K3 (menadione) has shown toxicity. K4, and K5 are also non toxic. Measurement of these compounds are useful indices of vitamin K nutritional status and the efficacy of certain vitamin K analogs.

In another embodiment, the present disclosure can be used to retain, separate and resolve Vitamin E and related compounds. Vitamin E refers to a group of eight fat-soluble compounds that include both tocopherols and tocotrienols. Of the many different forms of vitamin E, γ-tocopherol is the most common in the North American diet. γ-Tocopherol can be found in corn oil, soybean oil, margarine, and dressings. α-tocopherol, the most biologically active form of vitamin E, is the second-most common form of vitamin E in the diet. This variant can be found most abundantly in wheat germ oil, sunflower, and safflower oils. As a fat-soluble antioxidant, it stops the production of reactive oxygen species formed when fat undergoes oxidation. Amounts over 1,000 mg (1,500 IU) per day are called Hypervitaminosis E, as they may increase the risk of bleeding problems and vitamin K deficiency. Measurement of these compounds are useful indices of vitamin e nutritional status and the efficacy of certain vitamin E analogs.

In general, a sample is a composition including at least one target analyte (e.g., an analyte of the class or kind disclosed above, together with a matrix). Samples can include a solid, liquid, gas, mixture, material (e.g., of intermediary consistency, such as an extract, cell, tissue, organisms) or a combination thereof. In various embodiments, the sample is a bodily sample, an environmental sample, a food sample, a synthetic sample, an extract (e.g., obtained by separation techniques), or a combination thereof.

Bodily samples can include any sample that is derived from the body of an individual. In this context, the individual can be an animal, for example a mammal, for example a human. Other example individuals include a mouse, rat, guinea-pig, rabbit, cat, dog, goat, sheep, pig, cow, or horse. The individual can be a patient, for example, an individual suffering from a disease or being suspected of suffering from a disease. A bodily sample can be a bodily fluid or tissue, for example taken for the purpose of a scientific or medical test, such as for studying or diagnosing a disease (e.g., by detecting and/or identifying a pathogen or the presence of a biomarker). Bodily samples can also include cells, for example, pathogens or cells of the individual bodily sample (e.g., tumour cells). Such bodily samples can be obtained by known methods including tissue biopsy (e.g., punch biopsy) and by taking blood, bronchial aspirate, sputum, urine, faeces, or other body fluids. Exemplary bodily samples include humour, whole blood, plasma, serum, umbilical cord blood (in particular, blood obtained by percutaneous umbilical cord blood sampling (PUBS), cerebrospinal fluid (CSF), saliva, amniotic fluid, breast milk, secretion, ichor, urine, faeces, meconium, skin, nail, hair, umbilicus, gastric contents, placenta, bone marrow, peripheral blood lymphocytes (PBL), and solid organ tissue extract.

Environmental samples can include any sample that is derived from the environment, such as the natural environment (e.g., seas, soils, air, and flora) or the manmade environment (e.g., canals, tunnels, buildings). Exemplary environmental samples include water (e.g., drinking water, river water, surface water, ground water, potable water, sewage, effluent, wastewater, or leachate), soil, air, sediment, biota (e.g., soil biota), flora, fauna (e.g., fish), and earth mass (e.g., excavated material).

Food samples can include any sample that is derived from food (including beverages). Such food samples can be used for various purposes including, for example, (1) to check whether a food is safe; (2) to check whether a food contained harmful contaminants at the time the food was eaten (retained samples) or whether a food does not contain harmful contaminants; (3) to check whether a food contains only permitted additives (e.g., regulatory compliance); (4) to check whether it contains the correct levels of mandatory ingredients (e.g., whether the declarations on the label of the food are correct); or (5) to analyze the amounts of nutrients contained in the food. Exemplary food samples include edible products of animal, vegetable or synthetic origin (e.g., milk, bread, eggs, or meat), meals, drinks, and parts thereof, such as retain samples. Food samples can also include fruits, vegetables, pulses, nuts, oil seeds, oil fruits, cereals, tea, coffee, herbal infusions, cocoa, hops, herbs, spices, sugar plants, meat, fat, kidney, liver, offal, milk, eggs, honey, fish, and beverages.

Synthetic samples can include any sample that is derived from an industrial process. The industrial process can be a biological industrial process (e.g., processes using biological material containing genetic information and capable of reproducing itself or being reproduced in a biological system, such as fermentation processes using transfected cells) or a non-biological industrial process (e.g., the chemical synthesis or degradation of a compound such as a pharmaceutical). Synthetic samples can be used to check and monitor the progress of the industrial process, to determine the yield of the desired product, and/or measure the amount of side products and/or starting materials.

EXAMPLES

Materials

All reagents were used as received unless otherwise noted. Those skilled in the art will recognize that equivalents of the following supplies and suppliers exist and, as such, the suppliers listed below are not to be construed as limiting.

Characterization Techniques

Those skilled in the art will recognize that equivalents of the following instruments and suppliers exist and, as such, the instruments listed below are not to be construed as limiting.

The % C values were measured by combustion analysis (CE-440 Elemental Analyzer; Exeter Analytical Inc., North Chelmsford, Mass.) or by Coulometric Carbon Analyzer (modules CM5300, CM5014, UIC Inc., Joliet, Ill.). Bromine and Chlorine content were determined by flask combustion followed by ion chromatography (Atlantic Microlab, Norcross, Ga.). The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, Ga.). The SSA was calculated using the BET method, the SPV was the single point value determined for $P/P_0 > 0.98$ and the APD was calculated from the desorption leg of the isotherm using the BJH method. The micropore surface area (MSA) was determined as the cumulative adsorption pore diameter data for pores<34 Å subtracted from the specific surface area (SSA). The median mesopore diameter (MMPD) and mesopore pore volume (MPV) were measured by Mercury Porosimetry (Micromeritics AutoPore II 9220 or AutoPore IV, Micromeritics, Norcross, Ga.). Skeletal densities were measured using a Micromeritics AccuPyc 1330 Helium Pycnometer (V2.04N, Norcross, Ga.). Particle sizes were measured using a Beckman Coulter Multisizer 3 analyzer (30 μm aperture, 70,000 counts; Miami, Fla.). The particle diameter ($dp_{50}$) was measured as the 50% cumulative diameter of the volume based particle size distribution. The width of the distribution was measured as the 90% cumulative volume diameter divided by the 10% cumulative volume diameter (denoted 90/10 ratio). Viscosity was determined for these materials using a Brookfield digital viscometer Model DV-II (Middleboro, Mass.). Measurements of pH were made with an Oakton pH100 Series meter (Cole-Palmer, Vernon Hills, Ill.) and were calibrated using ORION® (Thermo Electron, Beverly, Mass.) pH buffered standards at ambient temperature immediately before use. Titrations were performed using a METROHM® 716 DMS TITRINO® autotitrator (Metrohm, Hersau, Switzerland), and are reported as milliequivalents per gram (mequiv/g). Coverage levels for the epoxide were determined by titrating the OH⁻ liberated upon addition of sodium thio sulfate. Multinuclear ($^{13}C$, $^{29}Si$) CP-MAS NMR spectra were obtained using a Bruker Instruments Avance-300 spectrometer (7 mm double broadband probe). The spinning speed was typically 5.0-6.5 kHz, recycle delay was 5 sec. and the cross-polarization contact time was 6 msec. Reported $^{13}C$ and $^{29}Si$ CP-MAS NMR spectral shifts were recorded relative to tetramethylsilane using the external standards adamantane ($^{13}C$ CP-MAS NMR, δ 38.55) and hexamethylcyclotrisiloxane ($^{29}Si$ CP-MAS NMR, δ −9.62). Populations of different silicon environments were evaluated by spectral deconvolution using DMFit software. [Massiot, D.; Fayon, F.; Capron, M.; King, I.; Le Calvé, S.; Alonso, B.; Durand, J.-O.; Bujoli, B.; Gan, Z.; Hoatson, G. *Magn. Reson. Chem.* 2002, 40, 70-76]

Example 1 Preparation of Epoxide Layer for Stationary Phases

In a typical reaction, hybrid porous particles were dispersed in a solution of glycidoxypropyltrimethoxysilane/methanol (0.25 mL/g) (GLYMO, Aldrich, Milwaukee, Wis.,) in a 20 mM acetate buffer (pH 5.5, prepared using acetic acid and sodium acetate, J.T. BAKER® 5 mL/g dilution) that had be premixed at 70° C. for 60 minutes. The mixture was held at 70° C. for 20 hours. The reaction was then cooled and the product was filtered and washed successively with water and methanol (J.T. BAKER®). The product was then dried at 80° C. under reduced pressure for 16 hours. The specific particles used are shown in Table 1.

TABLE 1

Specific Base Particles Utilized

| Entry | Material |
|---|---|
| B1 | Hybrid Organic Silica (3.8 μm, 90 Å APD, 1.3 cm$^3$/g TPV)[1] |
| B2 | Hybrid Organic Silica (3.8 μm, 115 Å APD, 1.3 cm$^3$/g TPV)[1] |
| B3 | Hybrid Organic Silica (2.3 μm, 115 Å APD, 1.3 cm$^3$/g TPV)[1] |
| B4 | Hybrid Organic Silica (1.7 μm, 143 Å APD, 0.73 cm$^3$/g TPV |
| B5 | Hybrid Organic Silica (1.7 μm, 106 Å APD, 1.25 cm$^3$/g TPV |

[1]As described in U.S. Pat. No. 7,919,177, U.S. Pat. No. 7,223,473, U.S. Pat. No. 6,686,035 and WO2011084506

Reaction data is listed in Table 2. Specific changes to this general procedure include: 1) Material 1E was prepared utilizing a 6 hour reaction time, 2) Material 1F was prepared utilizing 100 mM acetate buffer, 3) Material 1G was prepared utilizing a 50° C. hold for 20 hours, 4) Material 1H was prepared utilizing a 50° C. premix and 50° C. hold. Total surface coverages of 3.90-6.0 μmol/m$^2$ were determined by the difference in particle % C before and after the surface modification as measured by elemental analysis. Analysis of these materials by $^{13}$C CP-MAS NMR spectroscopy indicates a mixture of epoxy and diol groups are present for these materials.

TABLE 2

Coverage of initial layer of Stationary Phases

| Example | Base Material Particle | Amount (g) | GPTMS Amount (g) | Total Coverage[1] (μmol/m$^2$) | Coverage of epoxide[2] (μmol/m$^2$) |
|---|---|---|---|---|---|
| 1A | B1 | 70 | 90.7 | 3.90 | 1.52 |
| 1B | B2 | 40 | 39.0 | 4.80 | 1.86 |
| 1C | B3 | 25 | 23.4 | 4.76 | 1.76 |
| 1D | B2 | 20 | 17.3 | 4.71 | 1.67 |
| 1E | B2 | 60 | 52.1 | 4.73 | 3.11 |
| 1F | B2 | 20 | 19.3 | 4.87 | 1.51 |
| 1G | B2 | 20 | 19.3 | 5.10 | 2.38 |
| 1H | B2 | 20 | 19.3 | 4.22 | 3.23 |
| 1I | B4 | 30 | 12.9 | 4.23 | 1.15 |
| 1J | B4 | 60 | 39.4 | 5.01 | 1.88 |
| 1K | B4 | 60 | 52.5 | 5.94 | 2.67 |
| 1L | B5 | 20 | 20.0 | 5.05 | 1.82 |

[1]This refers to the combined coverage from the bonded GPTMS silane – coverage from unhydrolyzed epoxides + coverage from hydrolyzed epoxides (as the diol).
[2]As determined by titration.

Example 2 Preparation of Stationary Phases with Diol Functionality

In a typical reaction, hybrid porous particles were dispersed in a solution of glycidoxypropyltrimethoxysilane/methanol (0.25 mL/g) (GLYMO, Aldrich, Milwaukee, Wis.) in a 20 mM acetate buffer (pH 5.5, prepared using acetic acid and sodium acetate, J.T. BAKER® 5 mL/g dilution) that had be premixed at 70° C. for 60 minutes. The mixture was held at 70° C. for 20 hours. The reaction was then cooled and the product was filtered and washed successively with water and methanol (J.T. BAKER®). The material was then refluxed in a 0.1 M acetic acid solution (5 mL/g dilution, J.T. BAKER®) at 70° C. for 20 hours. The reaction was then cooled and the product was filtered and washed successively with water and methanol (J.T. BAKER®). The product was then dried at 80° C. under reduced pressure for 16 hours. Reaction data is listed in Table 3. Surface coverages of 0.93-6.0 μmol/m$^2$ were determined by the difference in particle % C before and after the surface modification as measured by elemental analysis. Analysis of these materials by $^{13}$C CP-MAS NMR spectroscopy indicates no measurable amount of epoxide groups remain, having only diol groups present for these materials.

TABLE 3

Coverage of initial layer of Stationary Phases

| Example | Base Material Particle | Amount (g) | GPTMS Amount (g) | Total Coverage[1] (μmol/m$^2$) | Coverage of epoxide[2] (μmol/m$^2$) |
|---|---|---|---|---|---|
| 2A | B3 | 20 | 4.9 | 2.71 | N/A |
| 2B | B3 | 20 | 7.0 | 3.37 | N/A |
| 2C | B1 | 70 | 90.3 | 3.16 | N/A |
| 2D | B1 | 20 | 7.3 | 1.76 | N/A |
| 2E | B1 | 20 | 4.4 | 0.93 | N/A |
| 2F | B5 | 50 | 48.6 | 4.91 | N/A |

Example 3—Preparation of Stationary Phases with Mixed Functionality

In a standard experiment, 10 g of a material prepared above were dispersed in a solvent such as, but not limited to water, iso-propanol, or dioxane. An amount of nucleophile in excess of the epoxide coverage determined for the material prepared above was added and the mixture heated to 70° C. for 16 hours. Table 4 provides the list of specific nucleophiles used. After reaction, the particles were washed successively with water and 0.5M acetic acid, and the material was then stirred in a 0.1 M acetic acid solution (5 mL/g dilution, J.T. BAKER®) at 70° C. for 20 hours. The reaction was then cooled and the product was filtered and washed successively with water and methanol (J.T. BAKER®). The product was then dried at 80° C. under reduced pressure for 16 hours. Reaction data is listed in Table 5. Nucleophile surface concentrations of 0.2-2.3 μmol/m$^2$ were determined by the difference in particle % C, % N or % S before and after the surface modification as measured by elemental analysis. Analysis of these materials by $^{13}$C CP-MAS NMR spectroscopy indicates no measurable amount of epoxide groups remain.

TABLE 4

List of Specific Nucleophiles Utilized

| Entry | Nucleophile |
|---|---|
| N1 | 1-aminoanthracene |
| N2 | 4-n-octylaniline |
| N3 | 6-aminoquinoline |

TABLE 4-continued

List of Specific Nucleophiles Utilized

| Entry | Nucleophile |
|---|---|
| N4 | aniline |
| N5 | 1-naphthylamine |
| N6 | 8-aminoquinoline |
| N7 | 2-aminoanthracene |
| N8 | benzylamine |
| N9 | 2-picolylamine |
| N10 | pyridine |
| N11 | N-octadecylamine |
| N12 | diethylamine |

TABLE 5

Base Material

| Example | Representative Preparation from Example 1 | Total Coverage from Initial Bonding ($\mu mol/m^2$) | Nucleophile Used | Nucleophile Surface Concentration ($\mu mol/m^2$) |
|---|---|---|---|---|
| 3A | 1C | 4.57 | N1 | 1.61 |
| 3B | 1I | 4.23 | N1 | 0.98 |
| 3C | 1J | 5.01 | N1 | 1.16 |
| 3D | 1K | 5.94 | N1 | 1.95 |
| 3E | 1H | 3.82 | N2 | 2.01 |
| 3F | 1C | 4.58 | N3 | 1.10 |
| 3G | 1C | 4.58 | N4 | 1.53 |
| 3H | 1C | 4.58 | N5 | 1.65 |
| 3I | 1C | 4.66 | N6 | 1.48 |
| 3J | 1C | 4.35 | N7 | 0.66 |
| 3K | 1C | 4.39 | N8 | 1.21 |
| 3L | 1L | 5.05 | N9 | 1.32 |
| 3M | 1C | 4.66 | N10 | 1.07 |
| 3N | 1H | 4.62 | N11 | 2.28 |
| 3O | 1L | 5.05 | N12 | 1.60 |
| 3P | 1C | 4.35 | N1 | 1.41 |

Example 4 Further Characterization of Stationary Phases

The general procedure for bonding s/functionalization of particles that is detailed in Examples 1-3 is applied to modify the surface silanol groups of different porous materials. Included in this are monolithic, spherical, granular, superficially porous and irregular materials that are silica, hybrid inorganic/organic materials, hybrid inorganic/organic surface layers on hybrid inorganic/organic, silica, titania, alumina, zirconia, polymeric or carbon materials, and silica surface layers on hybrid inorganic/organic, silica, titania, alumina, zirconia or polymeric or carbon materials. Also includes are stationary phase materials in the form of a spherical material, non-spherical material (e.g., including toroids, polyhedron); stationary phase materials having a highly spherical core morphology, a rod shaped core morphology, a bent-rod shaped core morphology, a toroid shaped core morphology; or a dumbbell shaped core morphology; and stationary phase materials having a mixture of highly spherical, rod shaped, bent rod shaped, toroid shaped, or dumbbell shaped morphologies. Example hybrid materials are shown in U.S. Pat. Nos. 4,017,528, 6,528,167, 6,686,035, and 7,175,913 as well as International Publication No. WO2008/103423, the contents of which are hereby incorporated by reference in their entireties. Superficially porous particle include those describe in U.S. Pub. Nos. 2013/0112605, 2007/0189944, and 2010/061367, the contents of which are hereby incorporated by reference in their entireties. The particles size for spherical, granular or irregular materials can vary from 5-500 µm; more preferably 15-100 µm; more preferably 20-80 µm; more preferably 40-60 µm. The APD for these materials can vary from 30 to 2,000 Å; more preferably 40 to 200 Å; more preferably 50 to 150 Å. The SSA for these materials can vary from 20 to 1000 $m^2/g$; more preferably 90 to 800 $m^2/g$; more preferably 150 to 600 $m^2/g$; more preferably 300 to 550 $m^2/g$. The TPV for these materials can vary from 0.3 to 1.5 $cm^3/g$; more preferably 0.5 to 1.4 $cm^3/g$; more preferably 0.7 to 1.3 $cm^3/g$. The macropore diameter for monolithic materials can vary from 0.1 to 30 µm, more preferably 0.5 to 25 µm, more preferably 1 to 20 µm.

Example 5 Stationary Phases Show Minimal Analyte Retention Variation Over Time Under Chromatographic Conditions The average % retention change was calculated by taking the percent difference of the average absolute peak retentions measured from the day 3, 10 or 30 chromatographic tests from the average absolute peak retentions measured on the day one chromatographic test. For each day tested, the columns were equilibrated under Mix1 test conditions for 20 minutes followed by three injections of Mix1 and then equilibrated under Mix2 Test conditions for 10 minutes, followed by three injections of Mix2. Conditions are shown in Table 6. Results are shown in Tables 7 and 8.

The % Less Retention was calculated by taking the percent difference of the day one average absolute peak retentions measured for Mix 1 and Mix 2 from the day one average absolute peak retentions measured for Mix 1 and Mix 2 on example 1A.

TABLE 6

Chromatographic Test Conditions for Retention Change Measurements

| | |
|---|---|
| Co-Solvent Mix1 | 5% methanol |
| Sample Mix1 | 3-benzoylpyridine (0.1 mg/mL) |
| Co-Solvent Mix2 | 10% methanol |
| Sample Mix2 | caffeine, thymine, papaverine, prednisolone, sulfanilamide (0.2 mg/mL each) |
| Column Dimension | 2.1 × 150 mm |
| Flow Rate | 1.0 mL/min |
| Column Temperature | 50° C. |
| Back Pressure | 1800 psi |
| Detector | ACQUITY ® PDA with SFC Flow Cell |
| Detector Setting | 254 nm 40 spec/sec |
| Weak Needle Wash | iso-propanol |
| Injection | 1.0 µL (2.0 µL loop with PLUNO injection mode) |
| Instrument | UPC$^2$ ® |
| Software | Empower |

TABLE 7

Retention Change from Example 2 Materials Over Time

| | Average % Retention Change | | |
|---|---|---|---|
| Example | 3 Day Test | 10 Day Test | 30 Day Test |
| 2A | 0.0 | / | / |
| 2B | 0.2 | / | / |
| 2C | 0.2 | / | 1.8 |
| 2D | 3.1 | / | 1.2 |
| 2E | 0.4 | / | 0.2 |

/ indicates that this test was not performed for this material.

TABLE 8

Retention Change From Comparable Materials Over Time

| Example | Average % Retention Change | | |
|---|---|---|---|
| | 3 Day Test | 10 Day Test | 30 Day Test |
| 8-1 | 0.8 | / | / |
| 8-2 | 0.0 | 0.6 | 0.7 |
| 8-3 | 0.2 | 1.6 | / |
| 8-4 | 0.7 | 2.0 | / |
| 8-5 | 0.2 | 0.6 | / |
| 8-6 | 0.4 | 2.0 | / |
| 8-7 | 1.3 | 2.2 | / |
| 8-8 | 1.0 | 1.6 | 0.4 |
| 8-9 | 0.5 | 0.0 | 1.1 |
| 8-10 | 2.4 | 1.1 | 1.0 |
| 8-11 | 0.2 | 2.3 | 2.9 |

/ indicates that this test was not performed for this material.

Figure 1A:
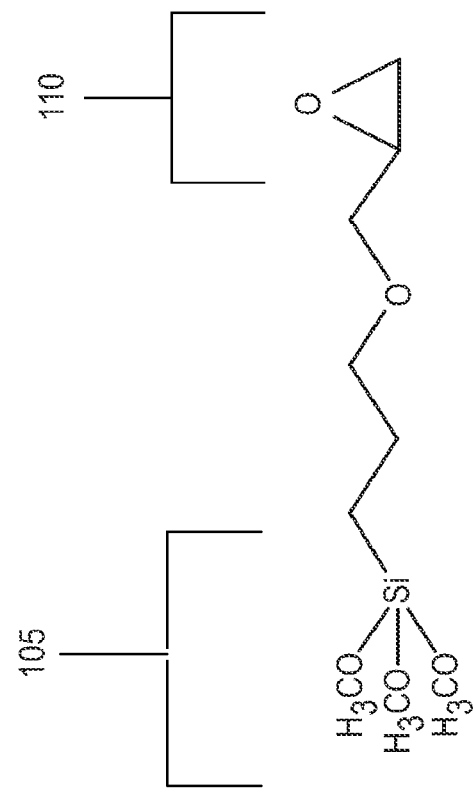

Example 6 Surface Functionalization of Organic-Inorganic Hybrid Particles with Glycidoxypropyltrimethoxysilane (GPTMS) and 1-aminoanthracene The structures of GPTMS and 1-aminoanthracene are shown in FIG. 1. FIG. 1A shows the structure of GPTMS, a silane surface modifier. Part 105 shows the surface reactive group of GPTMS (trialkoxysilane), while part 110 shows the reactive group (epoxide). FIG. 1B shows the selectivity ligand (1-aminoanthracene).

The GPTMS is first allowed to pre form oligomers by pre incubation at 70° C. in 20 mM sodium Acetate buffer pH 5.0. During incubation small oligomers of the hydrolyzed silanes are formed. After a suitable pre incubation period the particles to be modified are added as a dry powder. The oligomers and any remaining monomer react with the material surface to produce a high surface coverage of silane modifier covalently attached to the material surface as shown in FIG. 2.

Figure 2:
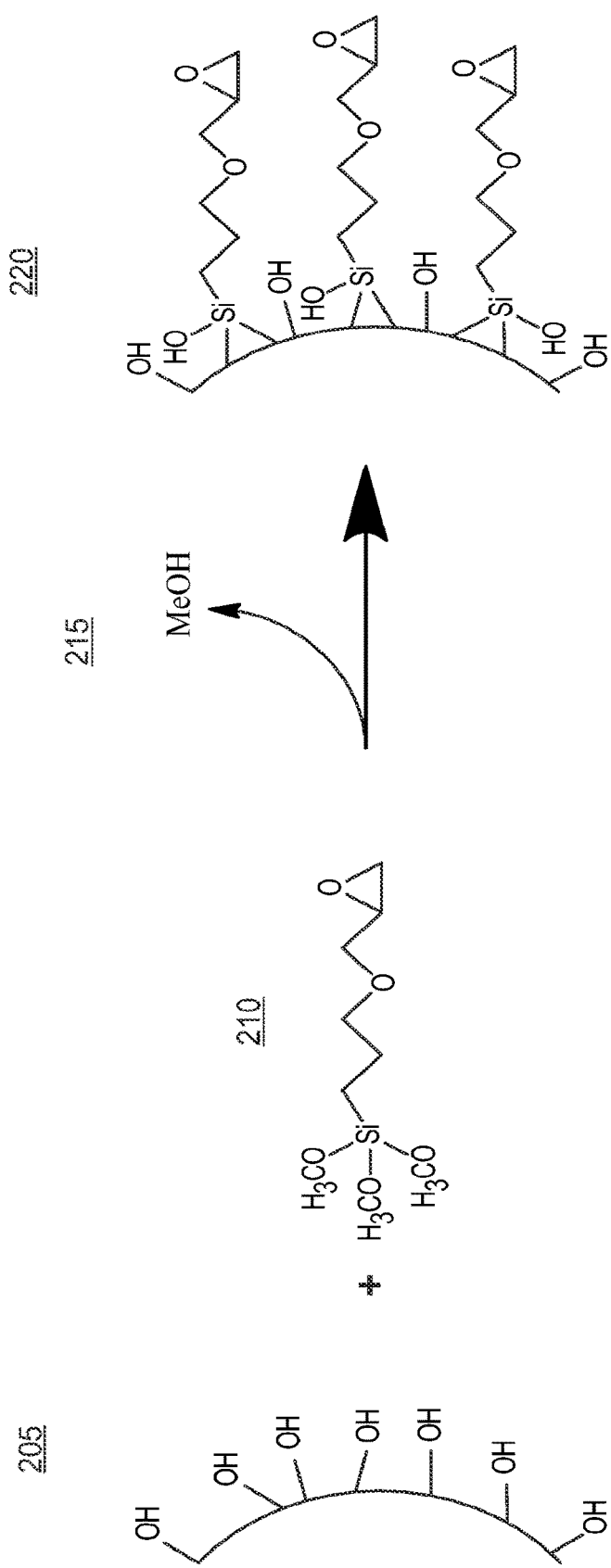
FIG. 2 shows a schematic of a reaction between an unmodified chromatographic surface and GPTMS.

FIG. 2 shows a reaction of the silane coupling agent with the organic-inorganic hybrid material surface. The silane (205) is depicted as a monomer for simplicity. Pre formed oligomeric silanes can couple in the same manner as the surface reactive group (210). In some embodiments, a portion of the silanes not attached to the surface can also couple to the coating (e.g., cross polymerization). Under reaction conditions, methanol is lost (215) to give surface modified particles (220).

After the silane has reacted with the chromatographic material, excess reagents and buffer salts are removed by washing with MILLI-Q® water and the materials are transferred into an organic solvent (e.g., 1,4-dioxane) and the 1-aminoanthracene added. The amino group of the 1-aminoanthracene couples to the surface through the pendant epoxide groups of the GPTMS. The proportion of epoxy groups converted can be controlled by limiting the quantity of 1-aminoanthracene added. The coupled materials are then washed into 0.5M acetic acid and the unreacted epoxide groups hydrolyzed to the corresponding diol as shown in FIG. 3.

The resulting 1-aminoanthracene/diol surface contains uniformly distributed 1-aminoanthracene groups and provides excellent selectivity while the diol shields the surface silanols from interaction with analyte. The multicomponent surface is superior to the singular diol surface or the singular 1-amino anthracene surface.

Figure 3:
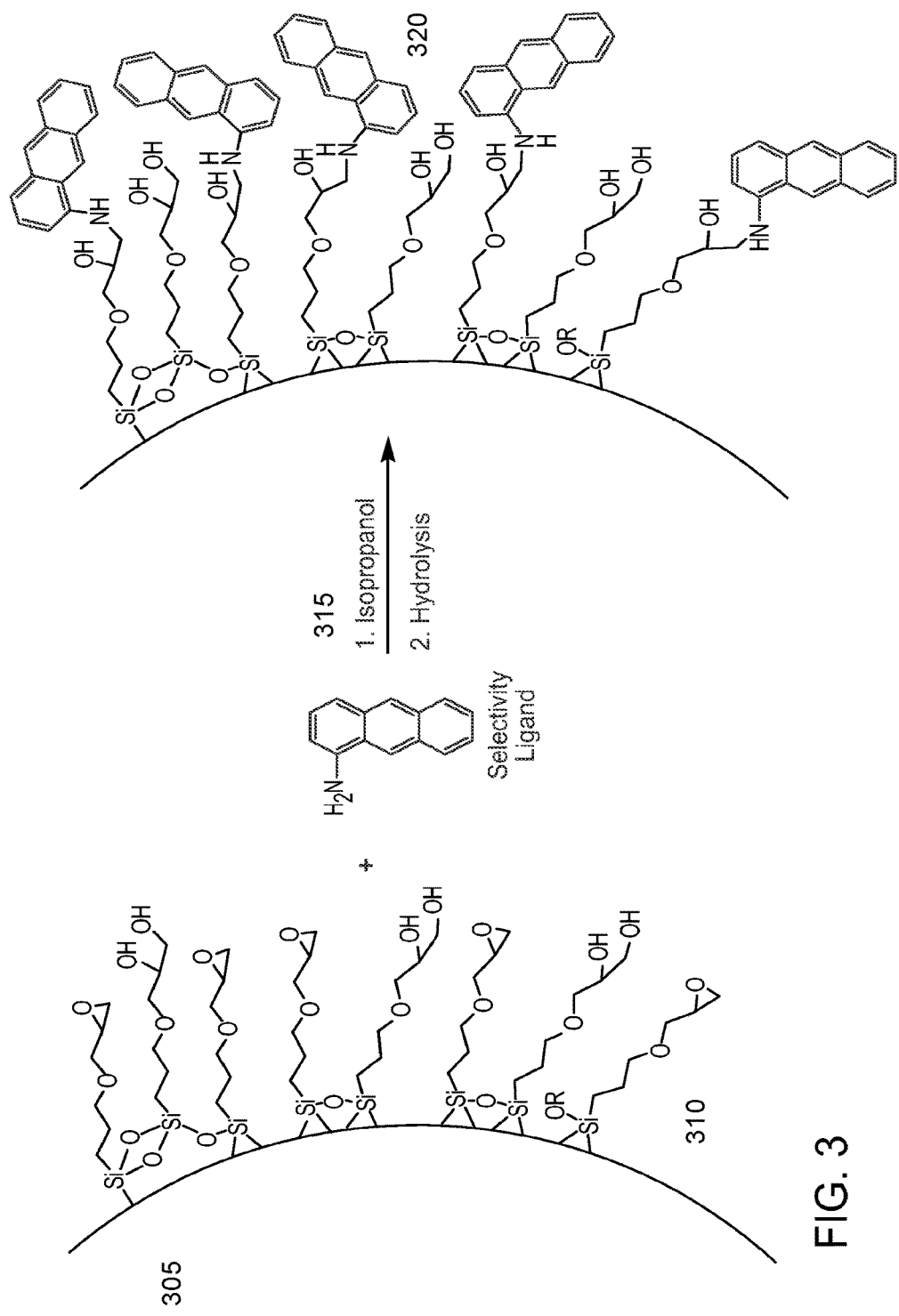
FIG. 3 shows a schematic of a reaction between a modified chromatographic surface and 1-aminoanthracene.

FIG. 3 shows reaction of the surface modified particle (305) with a selectivity ligand (310). The reaction conditions (315) are given and include treatment with isopropanol and 0.5 M acetic acid at 70° C. The result is a stationary phase particle with a multicomponent surface for chromatographic separation (320).

Alternatively, the multicomponent surface can be produced under conditions which create a polymerized surface by using a silane coupling agent with a pendant reactive group as the bonded phase under reaction conditions that simultaneously bond to the base material surface, partially react the pendant reactive group to form inert pendant groups and also produce limited polymerization between pendant reactive groups on adjacent silane coupling agent molecules.

Similarly, the multicomponent surface can be produced under conditions which create a polymerized surface by covalently bonding a second chemical agent capable of interacting with an analyte to affect retention through introduction of charged, uncharged, polar, nonpolar, lipophilic or hydrophilic character to the chromatographic phase. Alternatively, under certain conditions the epoxy groups of GPTMS can react with the hydroxyl groups of adjacent silanes to form ether bridges which crosslink the GPTMS on the surface. Such cross linking can provide stability to the bonded phase and can also enhance silanol shielding. The existence of such cross links is consistent with NMR analysis of these materials. An embodiment of the types of crosslinked surface is shown in FIG. 4. FIG. 4 also show a crosslinked silane group in the coating wherein the silane is not attached to the surface. Such a structure would demonstrate the formation of ether bridges through polymerization of the surface epoxides.

Example 7

Figure 5:
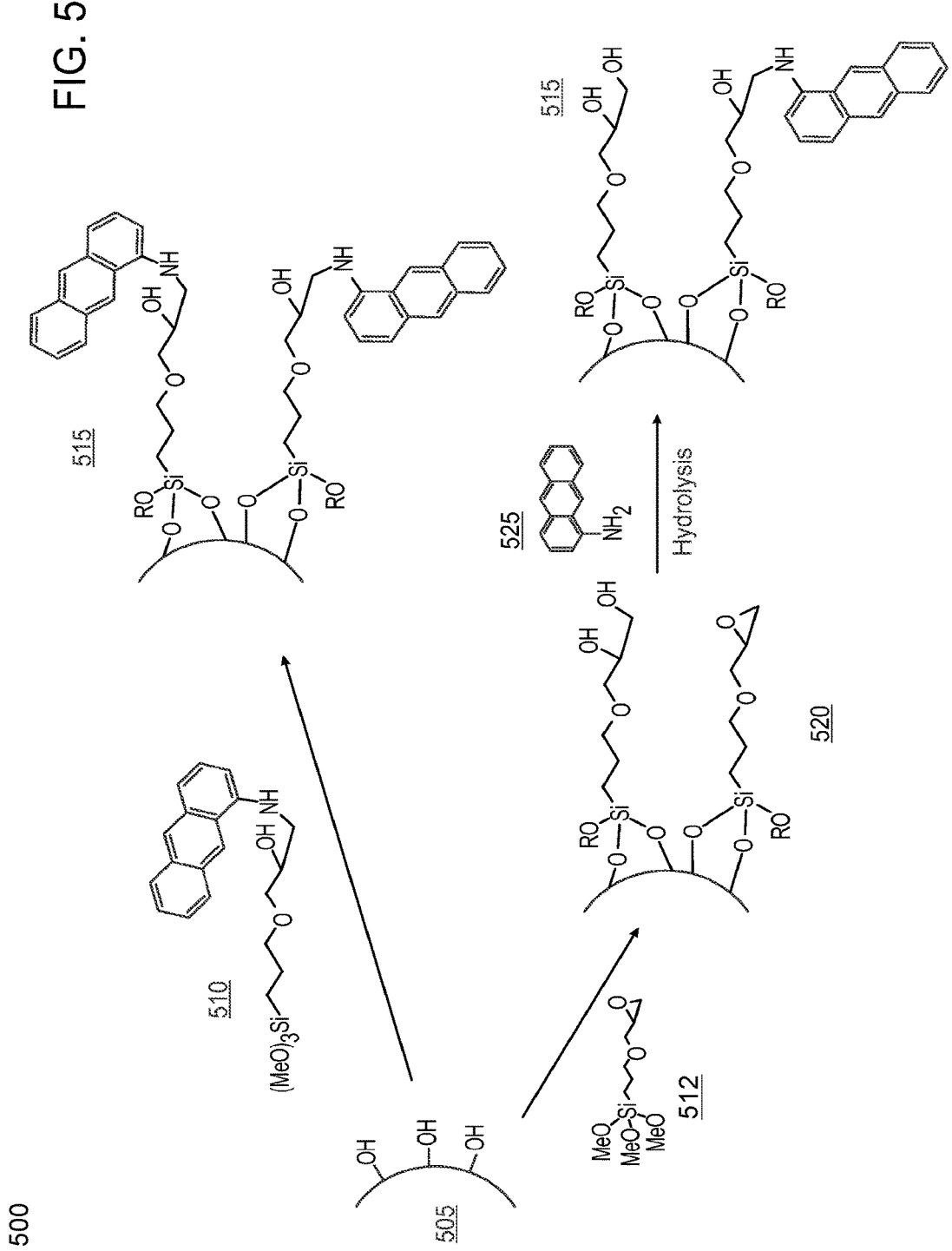
FIG. 5 shows a schematic of two potential synthetic routes to preparing a chromatographic stationary phase of the present disclosure.

FIG. 5 shows two potential synthetic routes to preparing a chromatographic stationary phase of the present disclosure. As shown in the scheme (500), an unmodified BEH particle (505) can be chemically modified in at least two different ways. Accordingly, one option, a chemical modifying agent (510) is first prepared by reacting GPTMS with 1-aminoanthracene. Agent 510 is then reacted with the BEH particle (505) to give a functionalized chromatographic surface (515).

Alternatively, FIG. 5 shows a different synthetic route. In this embodiment, particle 505 is reacted directly with GPTMS (512) to give a GPTMS-modified surface (520). Surface 520 can then be reacted with 1-aminoanthracene (525) to give a functionalized chromatographic surface (515).

In a preferred embodiment, the second reaction pathway comprising first reacting particle 505 with GPTMS (512) followed by functionalization with 1-aminoanthracene (525) is performed over the first reaction pathway comprising reacting particle 505 with a pre-formed chemical modifier 510.

Figure 6:
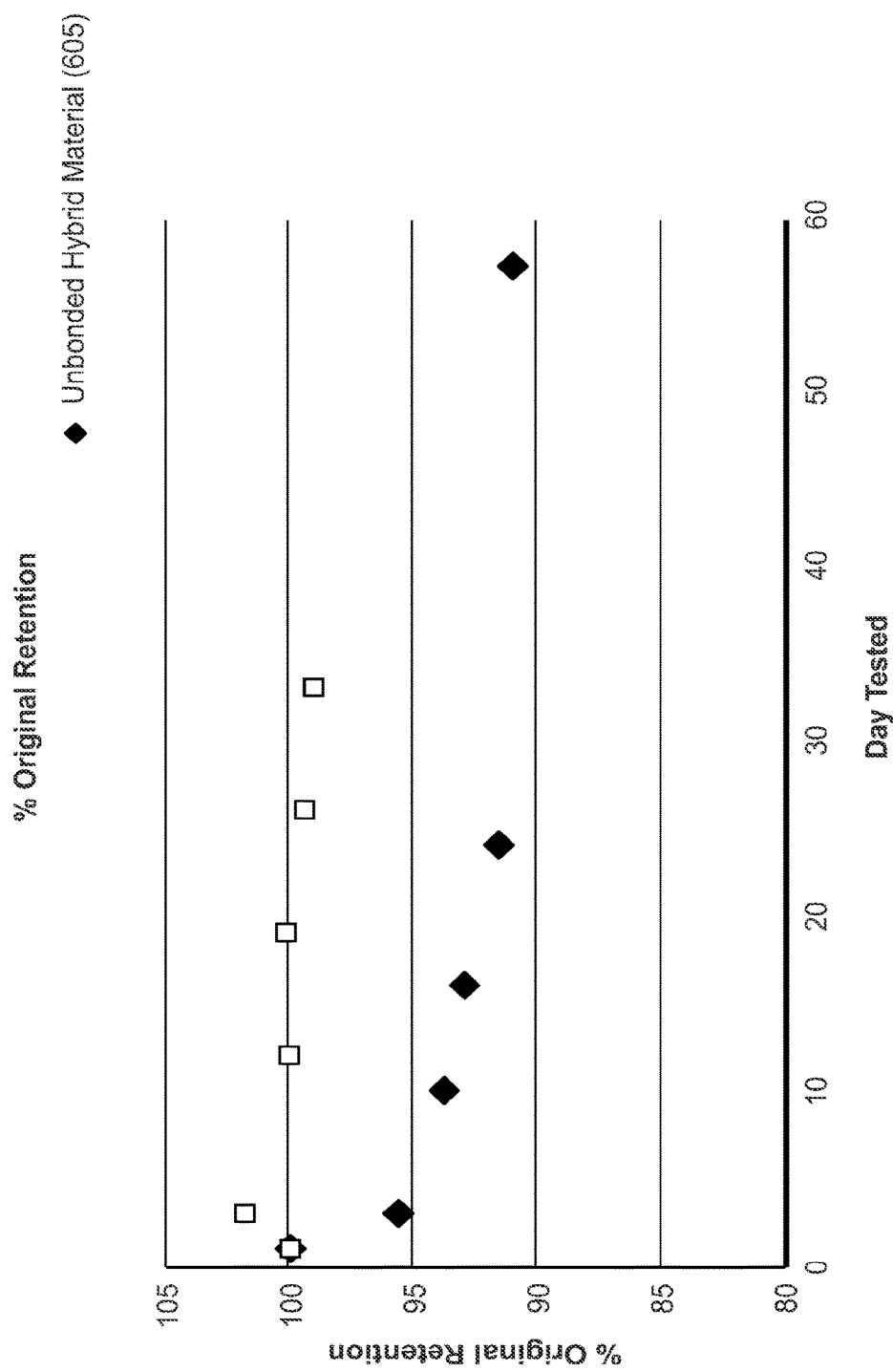
FIG. 6 shows a graph of the percent retention of an analyte eluted using unmodified BEH particles as a stationary phase, and BEH particles modified in accordance with the present disclosure.
Figure 7A:
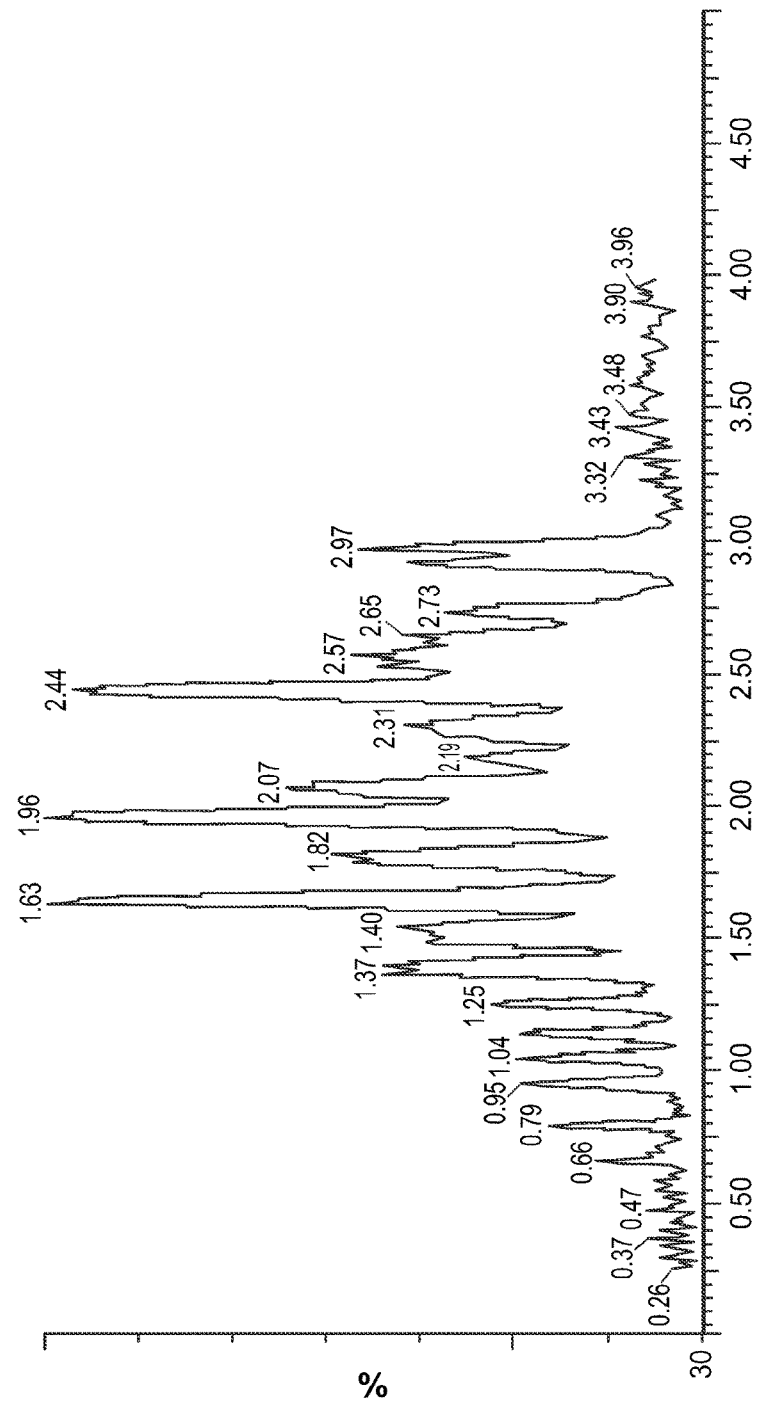
FIGS. 7A and 7B show exemplary lipid separations using a 1-aminoanthracene based stationary phase as described in Example 9.
Figure 7B:
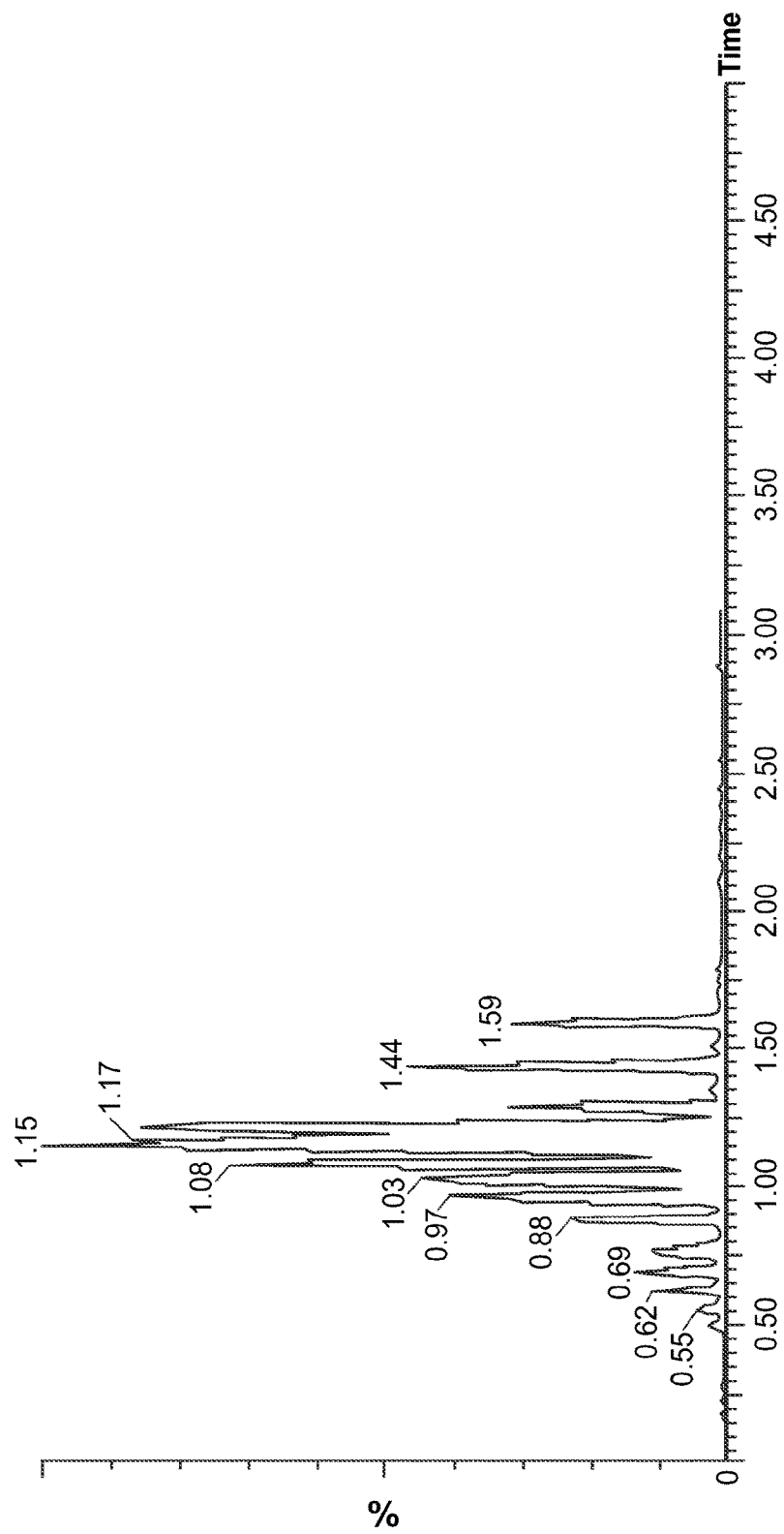
Figure 8A:
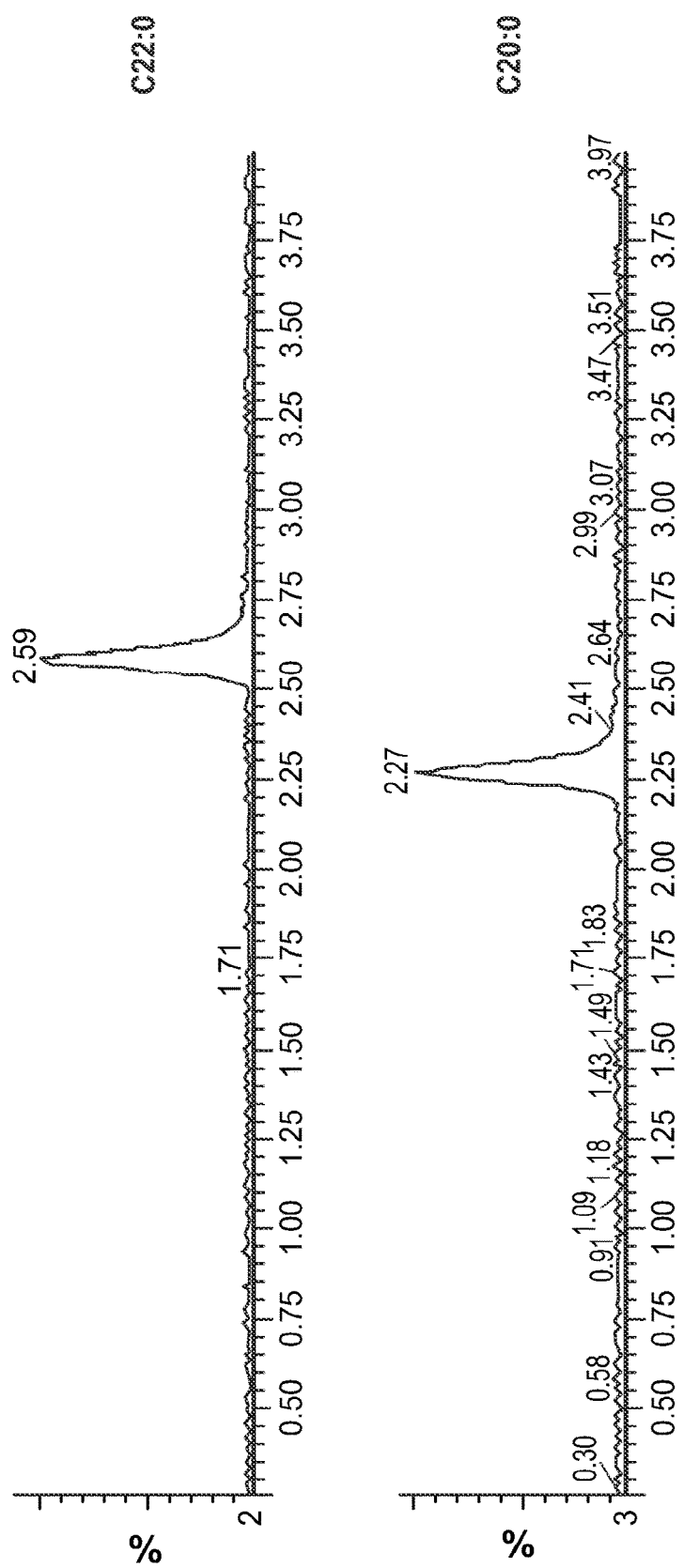
FIG. 8A shows chromatograms of C22:0 and C20:0 using a 1-aminoanthracene based stationary phase as described in Example 9.
Figure 8B:
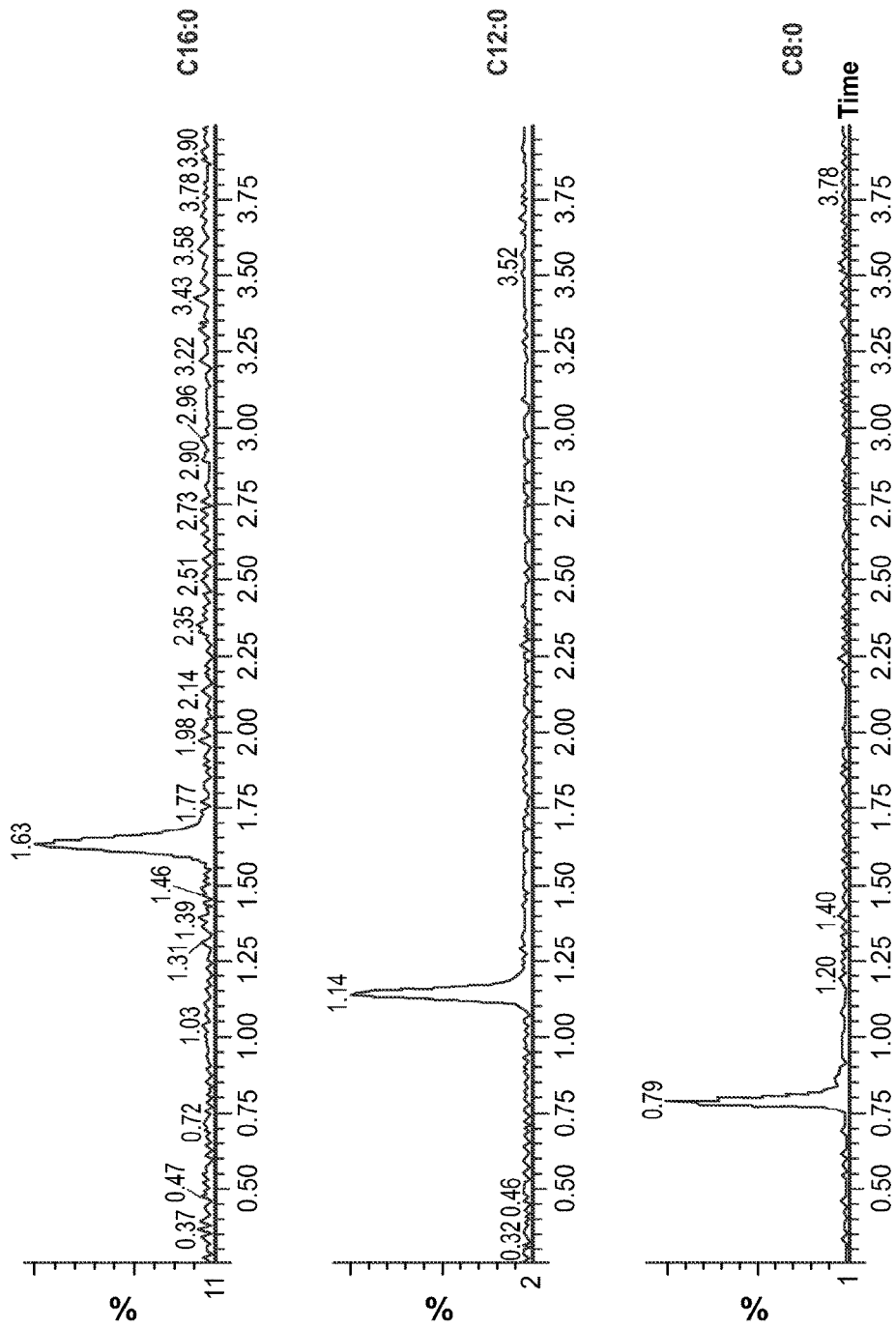
FIG. 8B shows chromatograms of C16:0, C12:0 and C8:0 using a 1-aminoanthracene based stationary phase as described in Example 9.
Figure 9A:
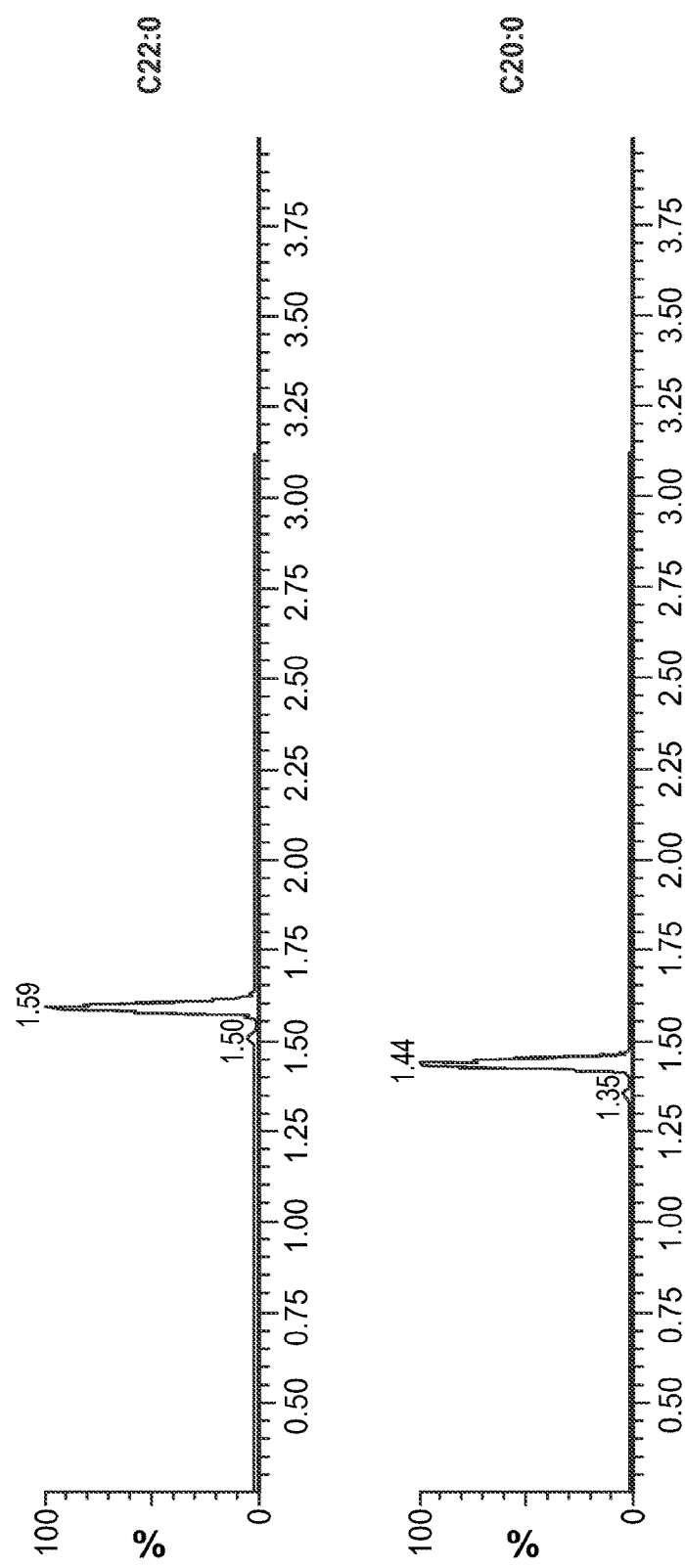
FIG. 9A shows chromatograms of C22:0 and C20:0 using a 1-aminoanthracene based stationary phase as described in Example 9.
Figure 9B:
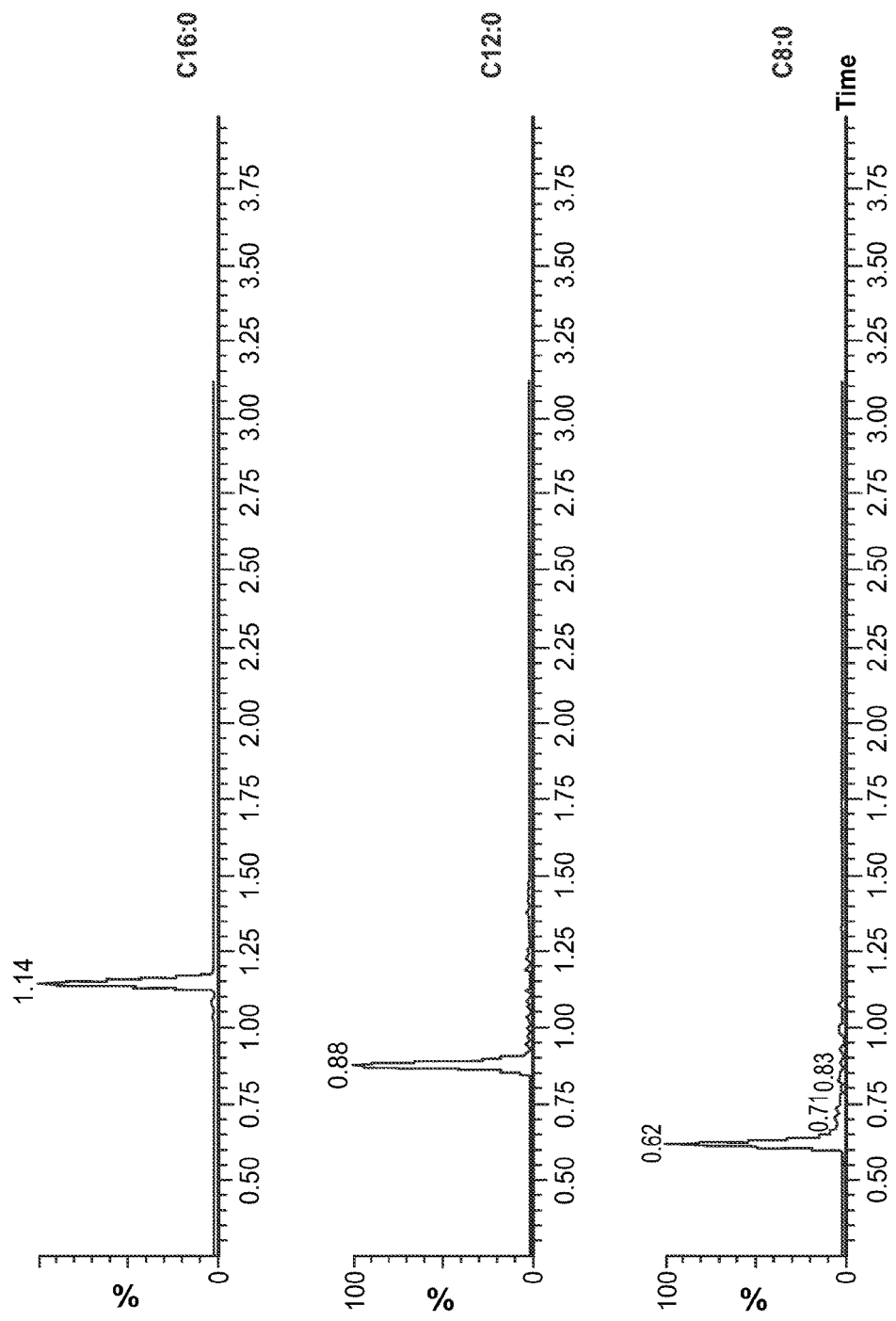
FIG. 9B shows chromatograms of C16:0, C12:0 and C8:0 using a 1-aminoanthracene based stationary phase as described in Example 9.
Figure 10A:
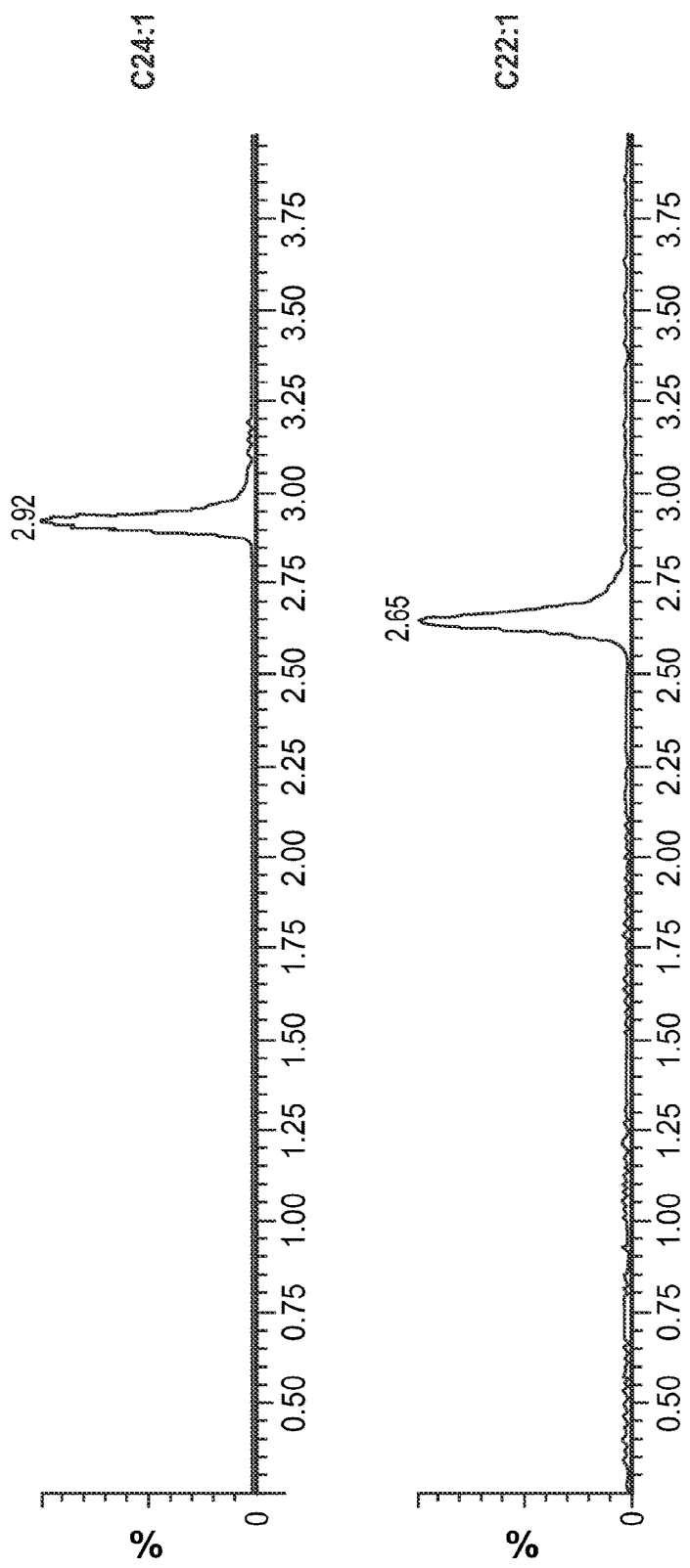
FIG. 10A shows chromatograms of C24:1 and C22:1 using a 1-aminoanthracene based stationary phase as described in Example 9.
Figure 10B:
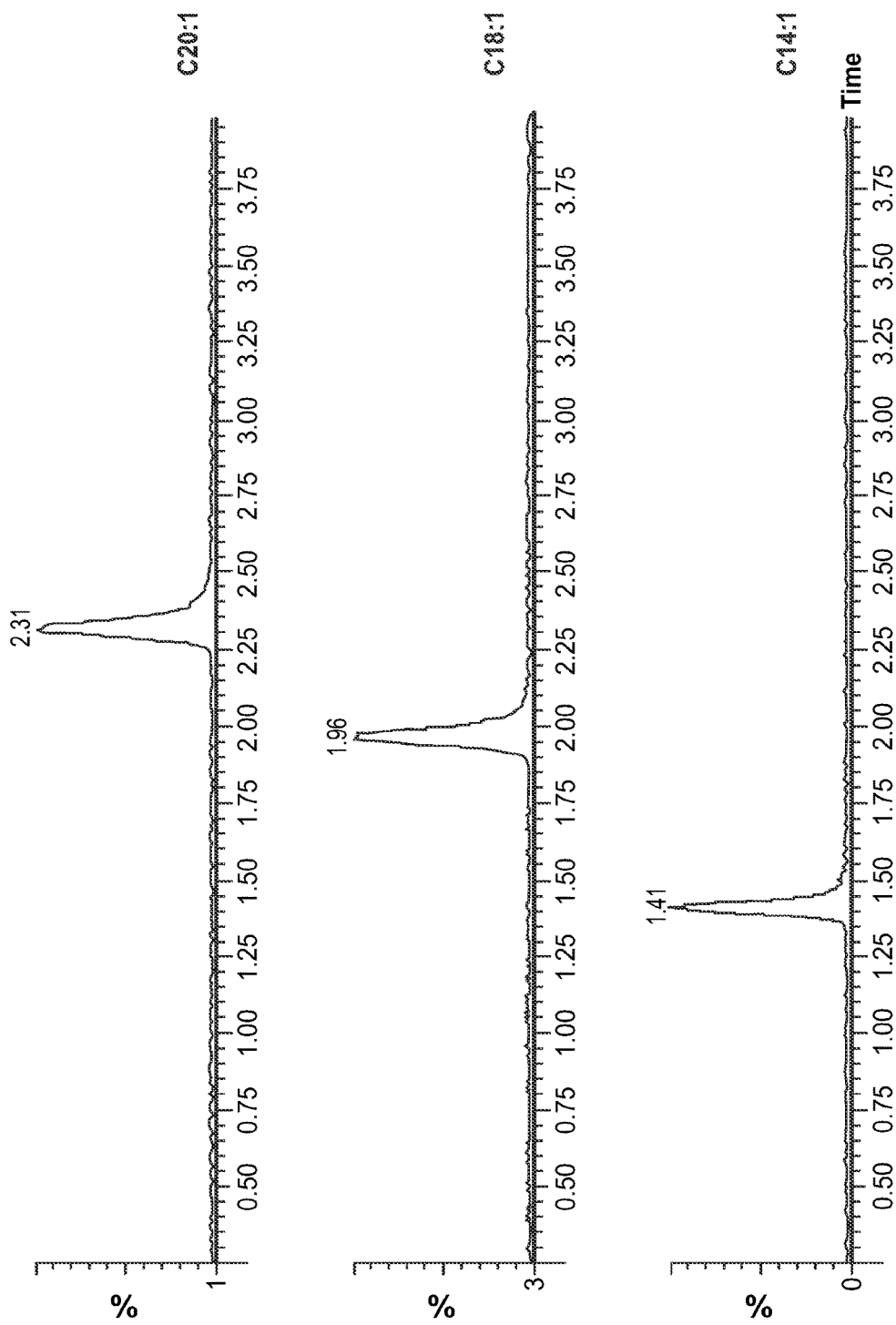
FIG. 10B shows chromatograms of C20:1, C18:1 and C14:1 using a 1-aminoanthracene based stationary phase as described in Example 9.
Figure 11A:
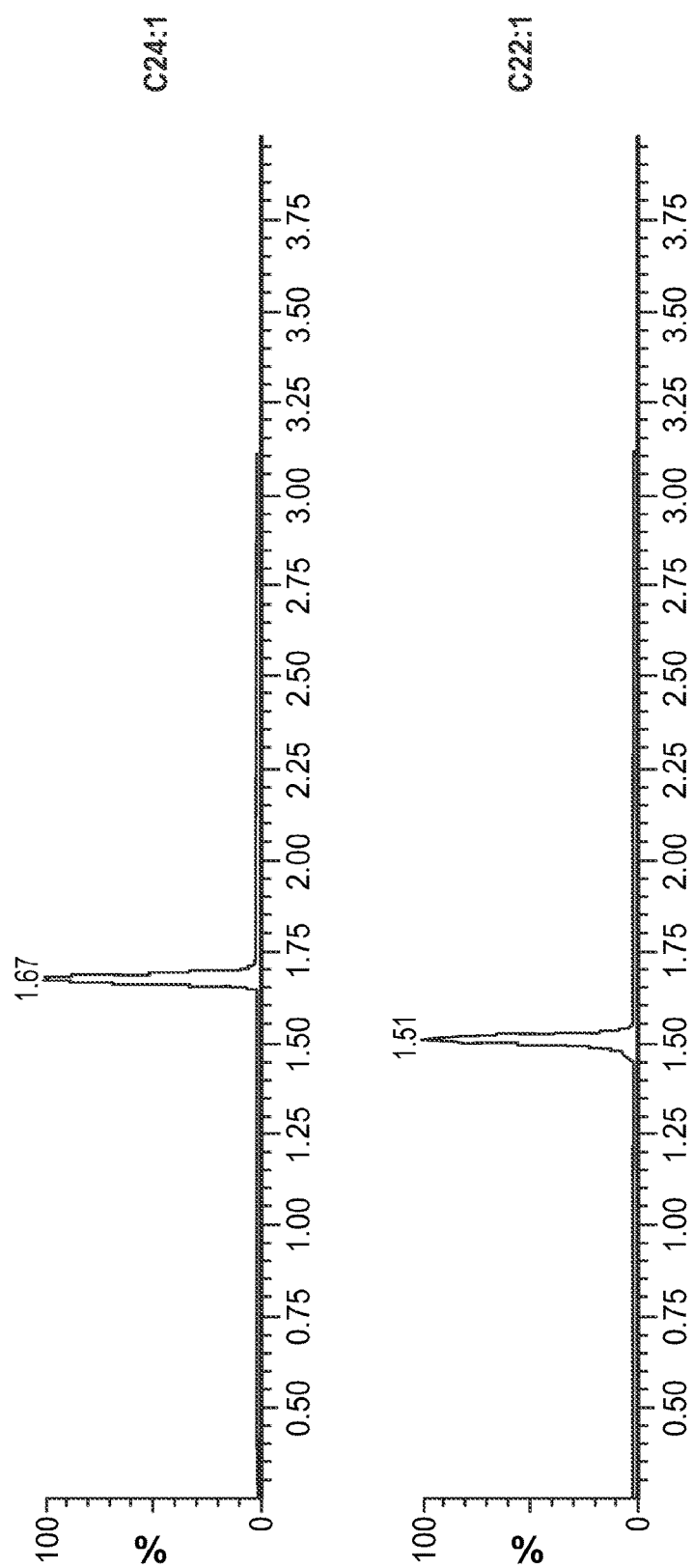
FIG. 11A shows chromatograms of C24:1 and C22:1 using a 1-aminoanthracene based stationary phase as described in Example 9.
Figure 11B:
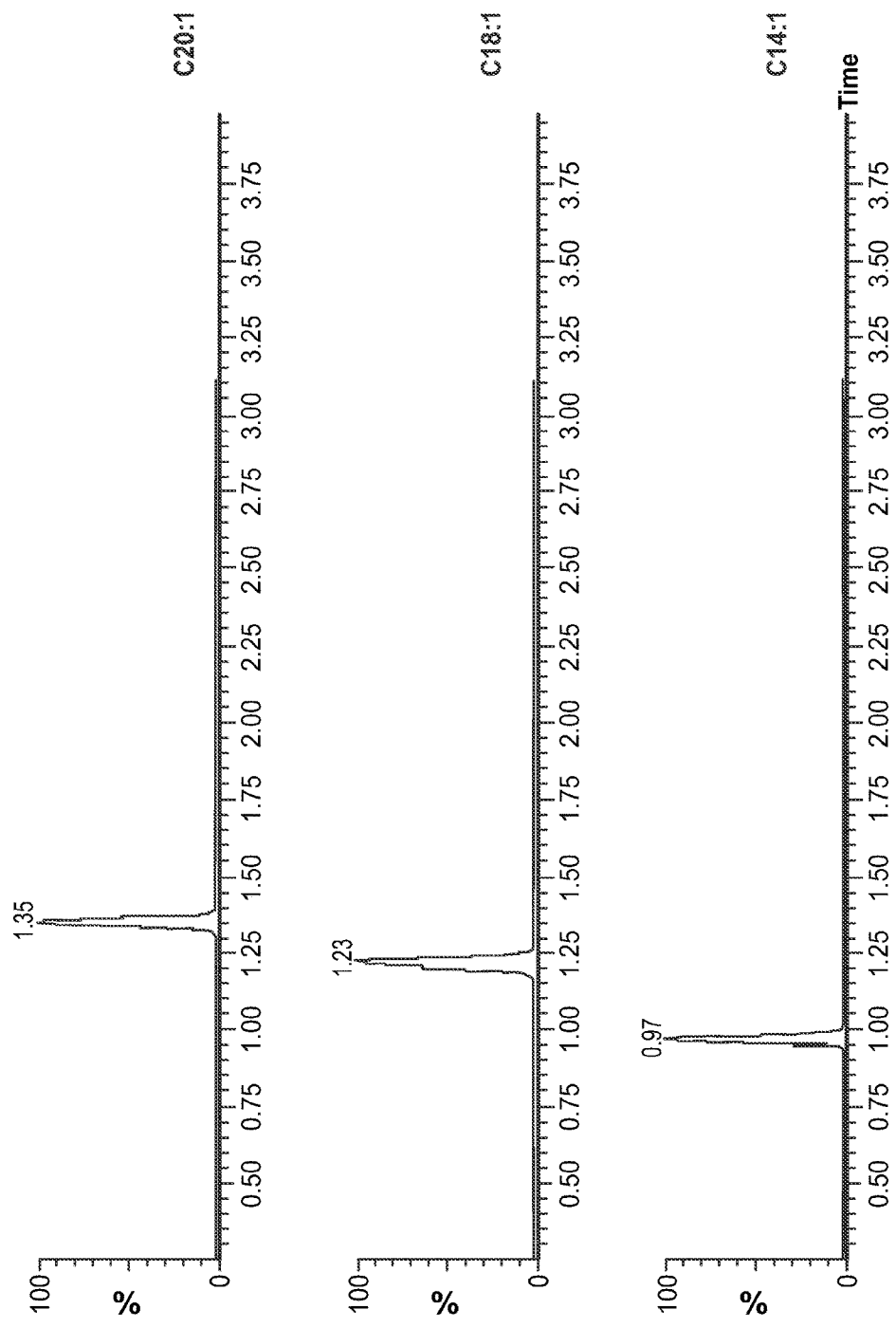
FIG. 11B shows chromatograms of C20:1, C18:1 and C14:1 using a 1-aminoanthracene based stationary phase as described in Example 9.
Figure 12A:
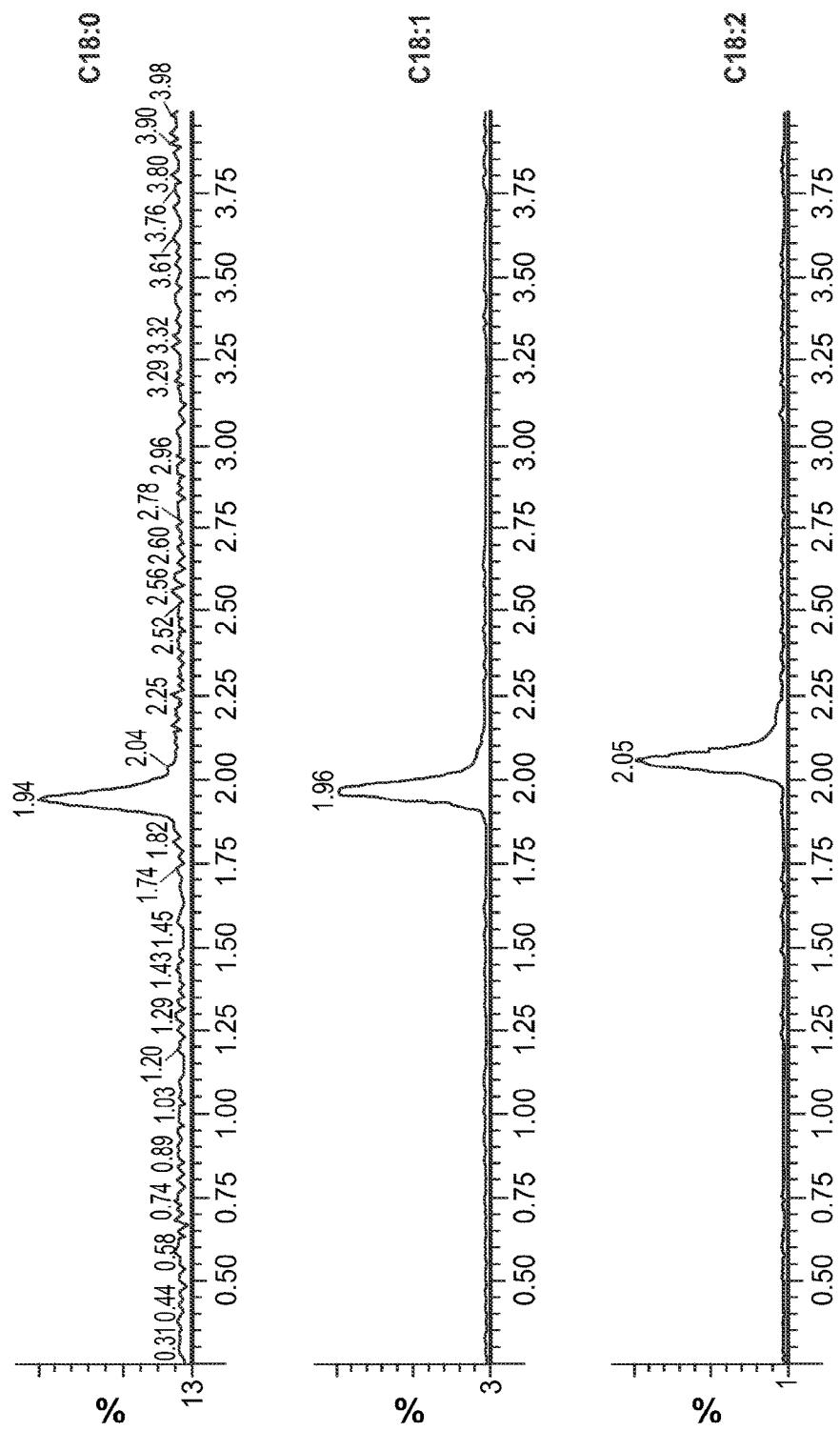
FIG. 12A shows chromatograms of C18:0. C18:1 and C18:2 using a 1-aminoanthracene based stationary phase as described in Example 9.
Figure 12B:
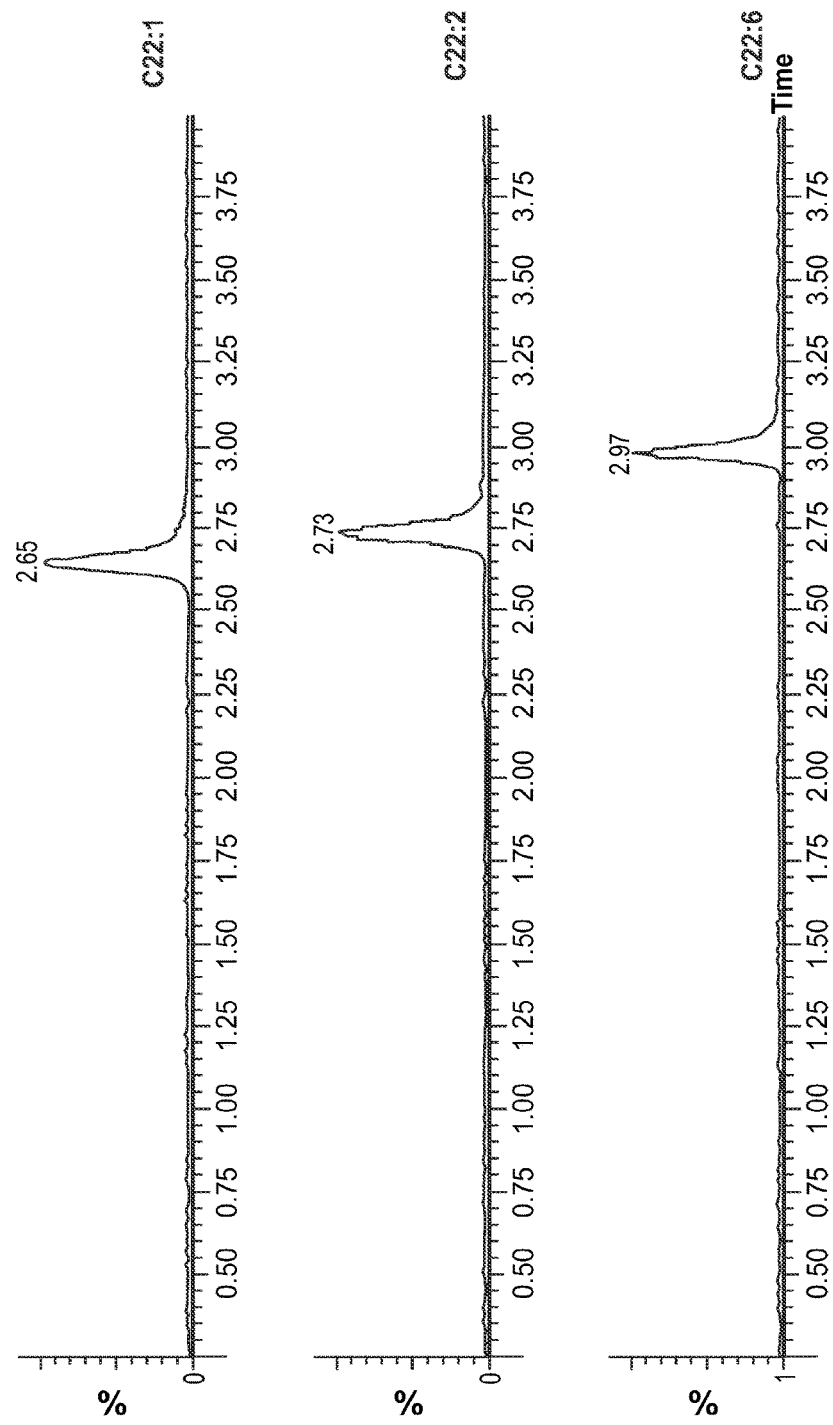
FIG. 12B shows chromatograms of C22:1. C22:2 and C22:6 using a 1-aminoanthracene based stationary phase as described in Example 9.
Figure 13A:
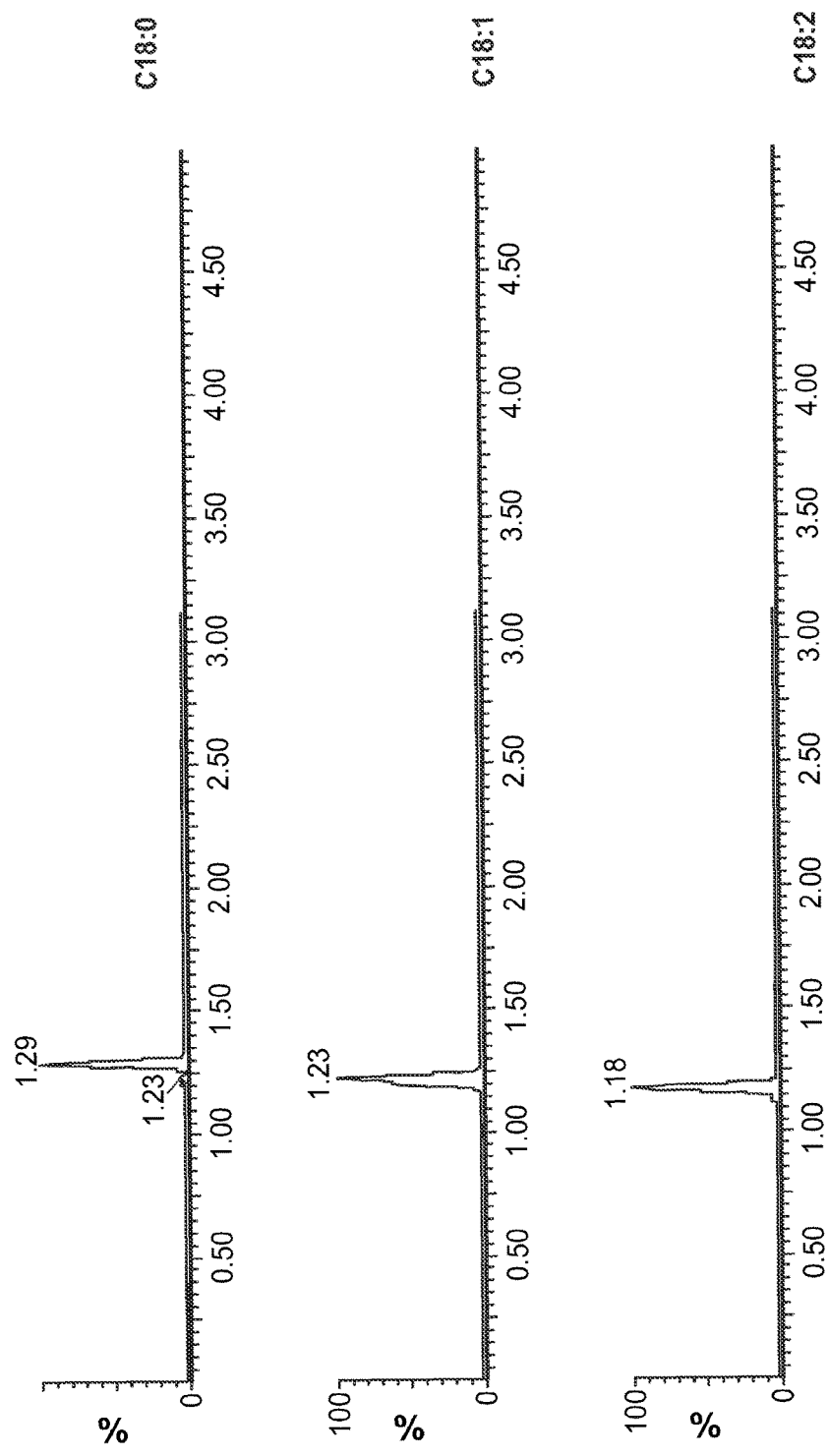
FIG. 13A shows chromatograms of C18:0, C18:1 and C18:2 using a 1-aminoanthracene based stationary phase as described in Example 9.
Figure 13B:
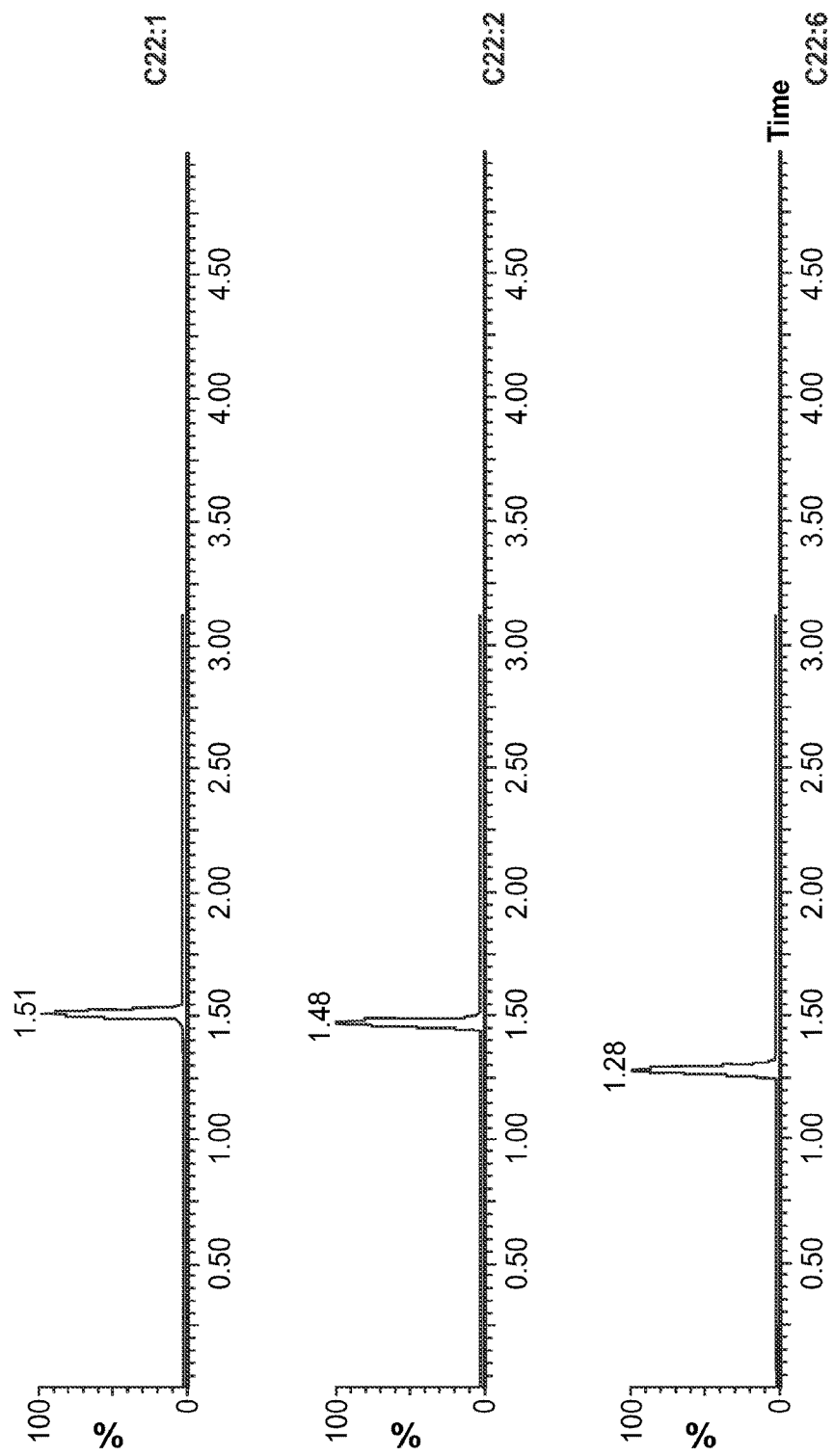
FIG. 13B shows chromatograms of C22:1, C22:2 and C22:6 using a 1-aminoanthracene based stationary phase as described in Example 9.
Figure 14:
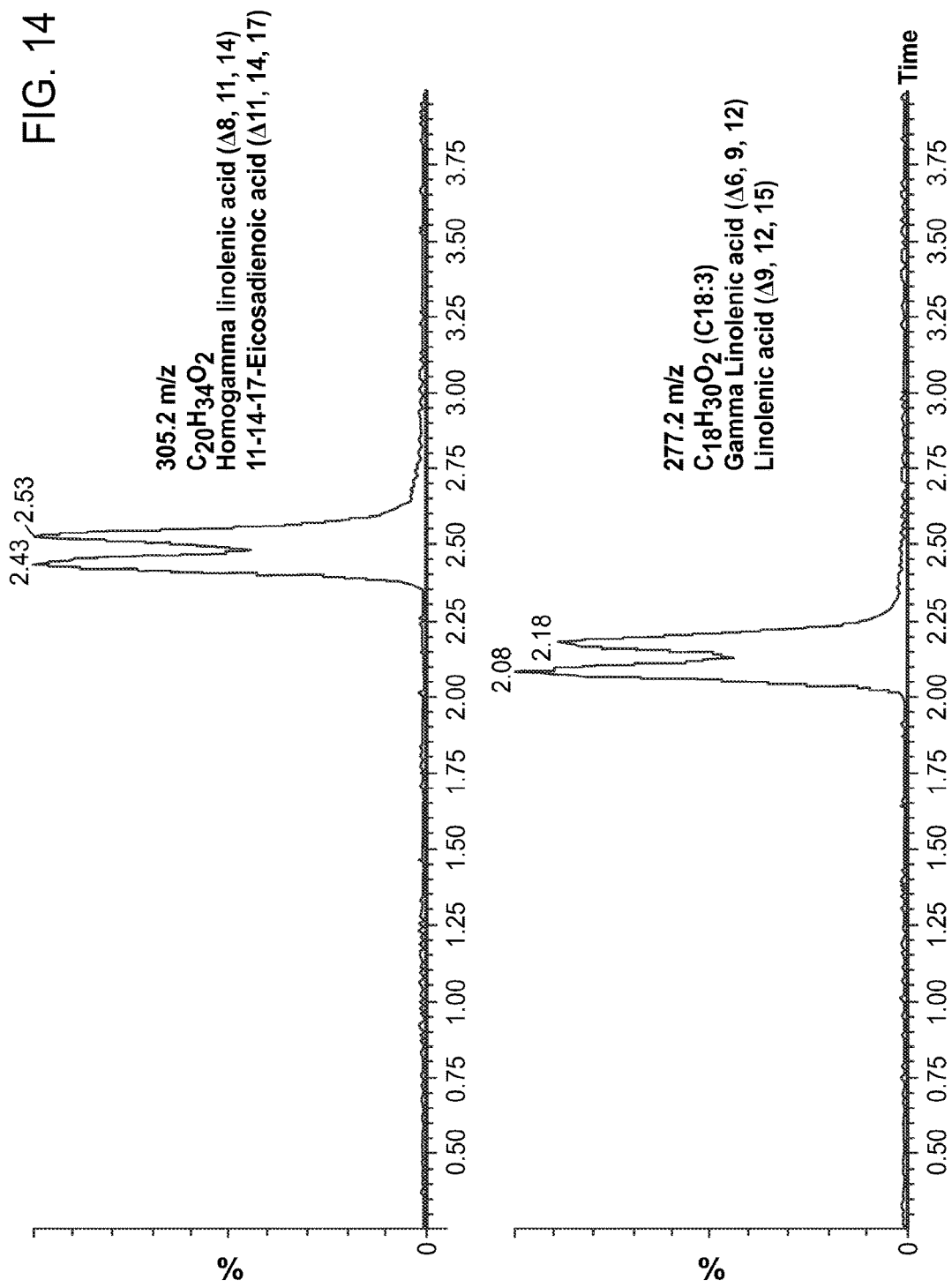
FIGS. 14 and 15 show chromatograms of various linolenic and eicosadienoic acids using a 1-aminoanthracene based stationary phase as described in Example 9.
Figure 15:
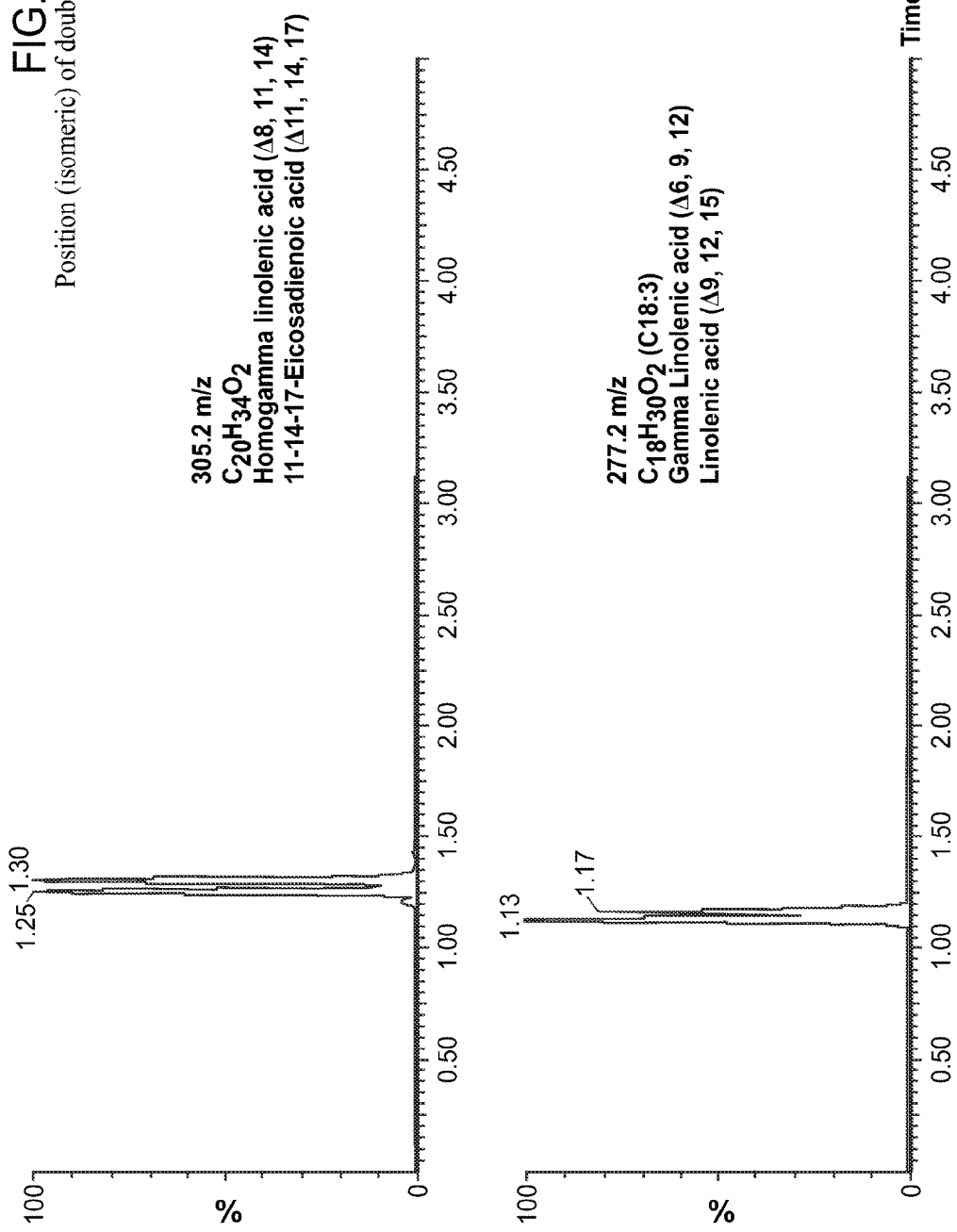
Figure 16:
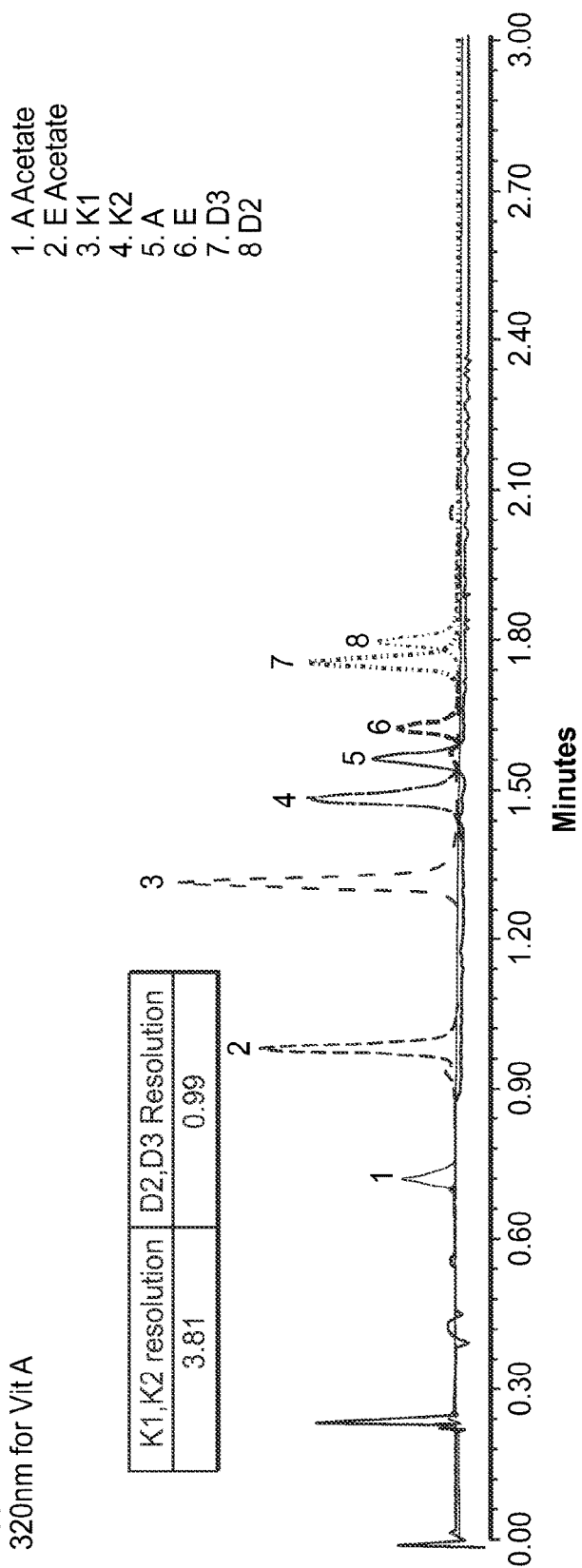
FIG. 16 shows an exemplary lipid separation achieved using a 1-aminoanthracene based stationary phase as described in Example 9.
Figure 18A:
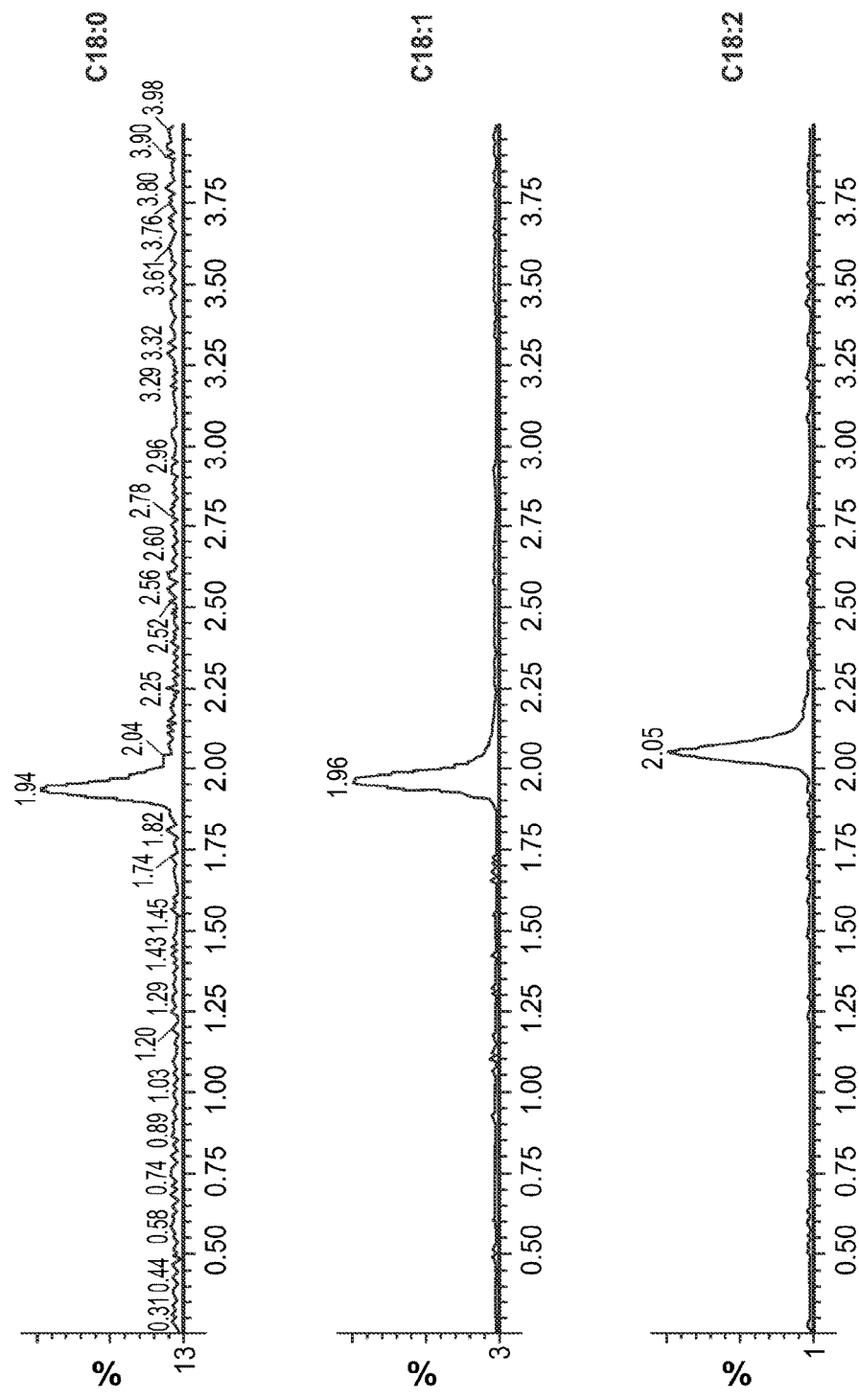
FIG. 18A shows chromatograms of C18:0, C18:1 and C18:2 using a 1-aminoanthracene based stationary phase as described in Examples 3 and 10.
Figure 18B:
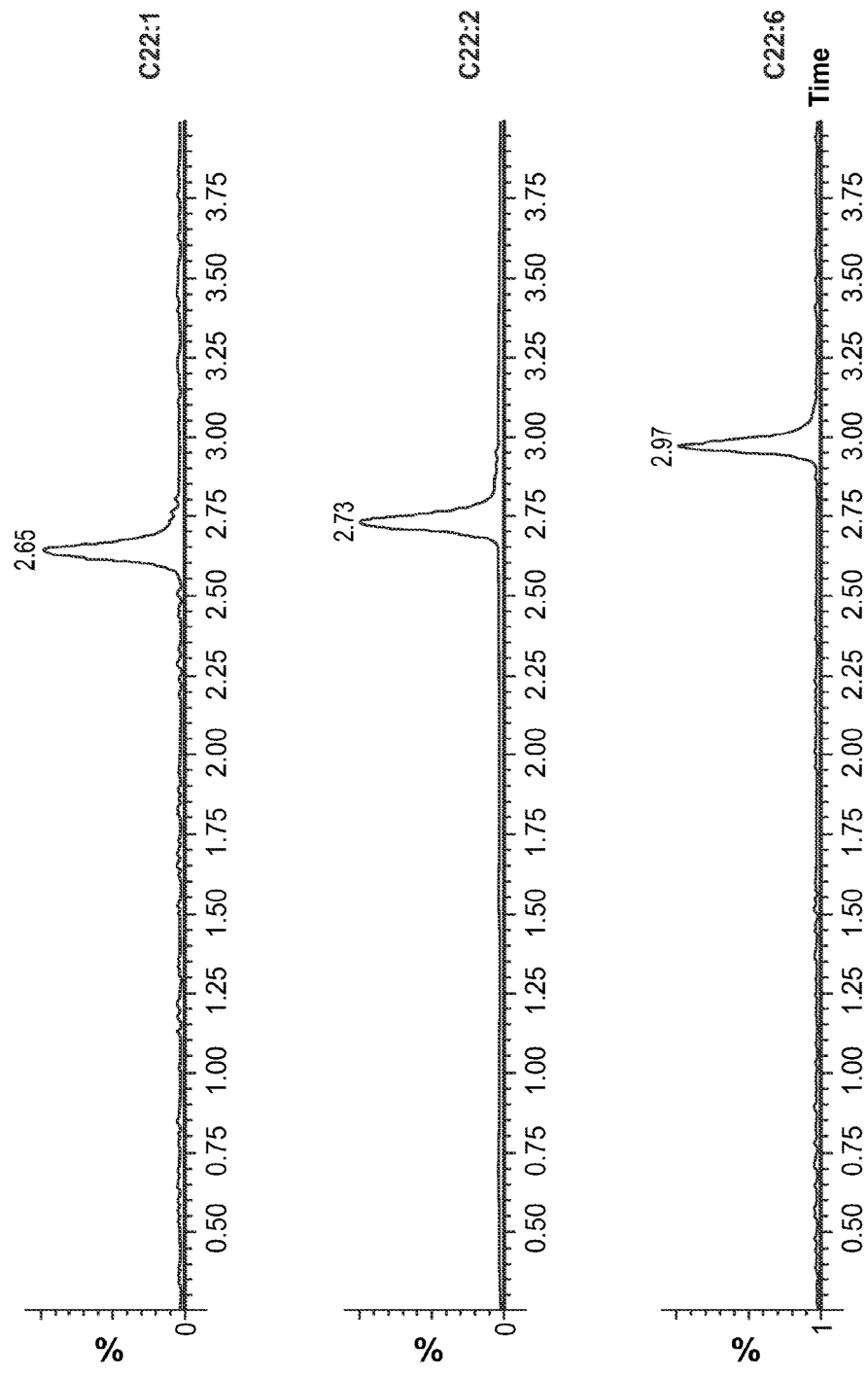
FIG. 18B shows chromatograms of C22:1, C22:2 and C22:6 using a 1-aminoanthracene based stationary phase as described in Examples 3 and 10.
Figure 19A:
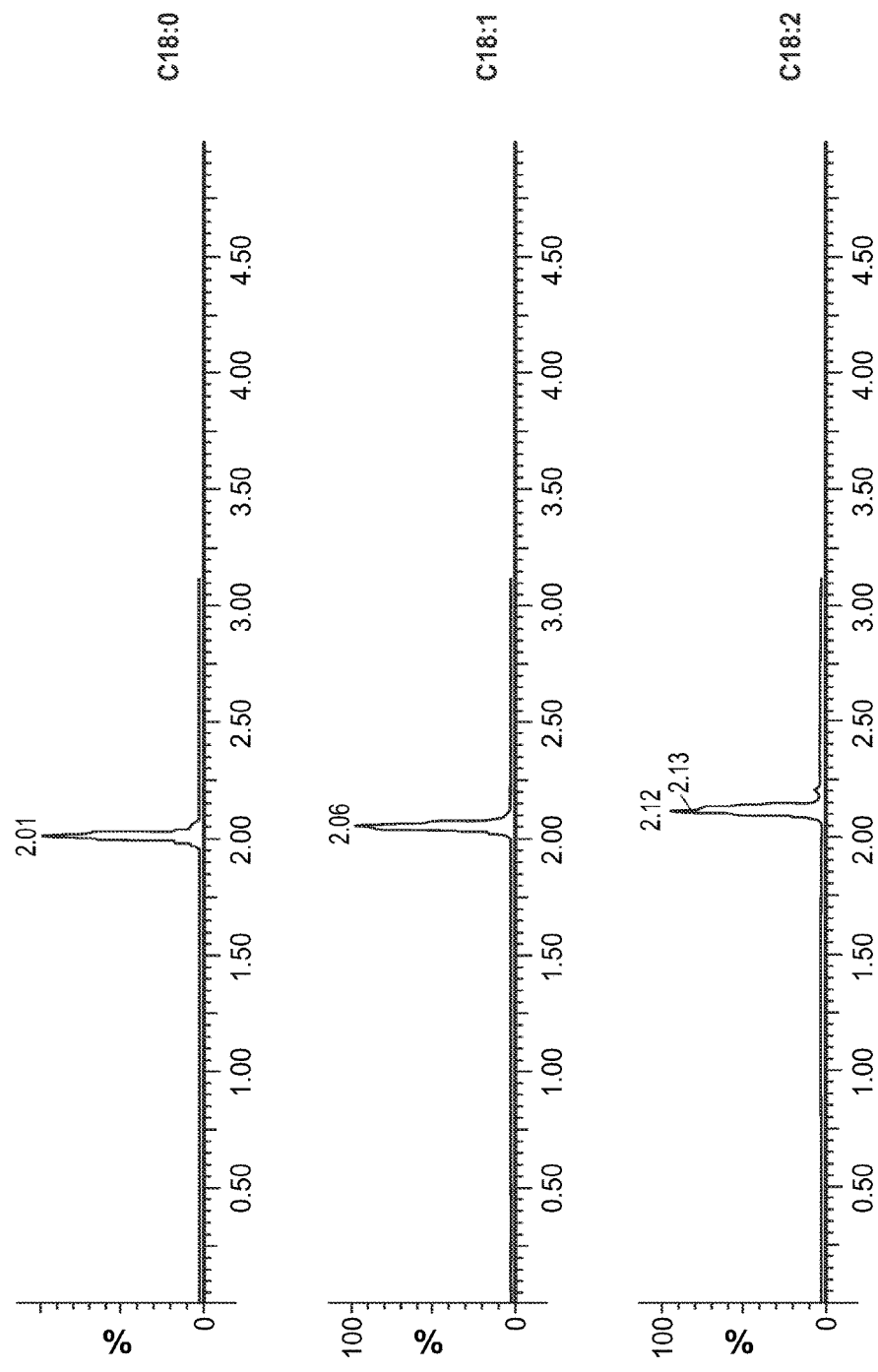
FIG. 19A shows chromatograms of C18:0, C18:1 and C18:2 using a 2-picolylamine based stationary phase as described in Examples 3 and 10.
Figure 19B:
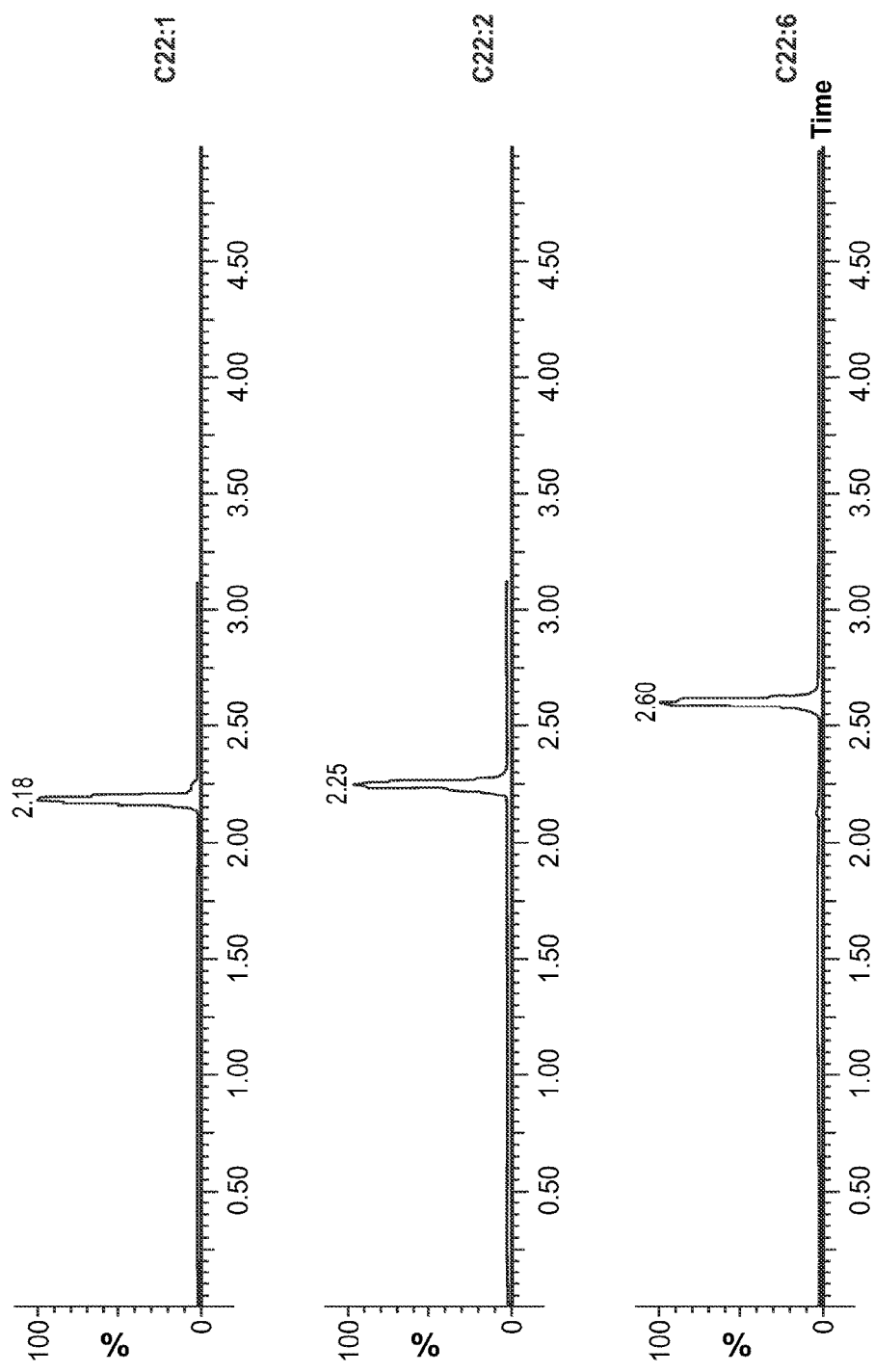
FIG. 19B shows chromatograms of C22:1, C22:2 and C22:6 using a 2-picolylamine based stationary phase as described in Examples 3 and 10.
Figure 20A:
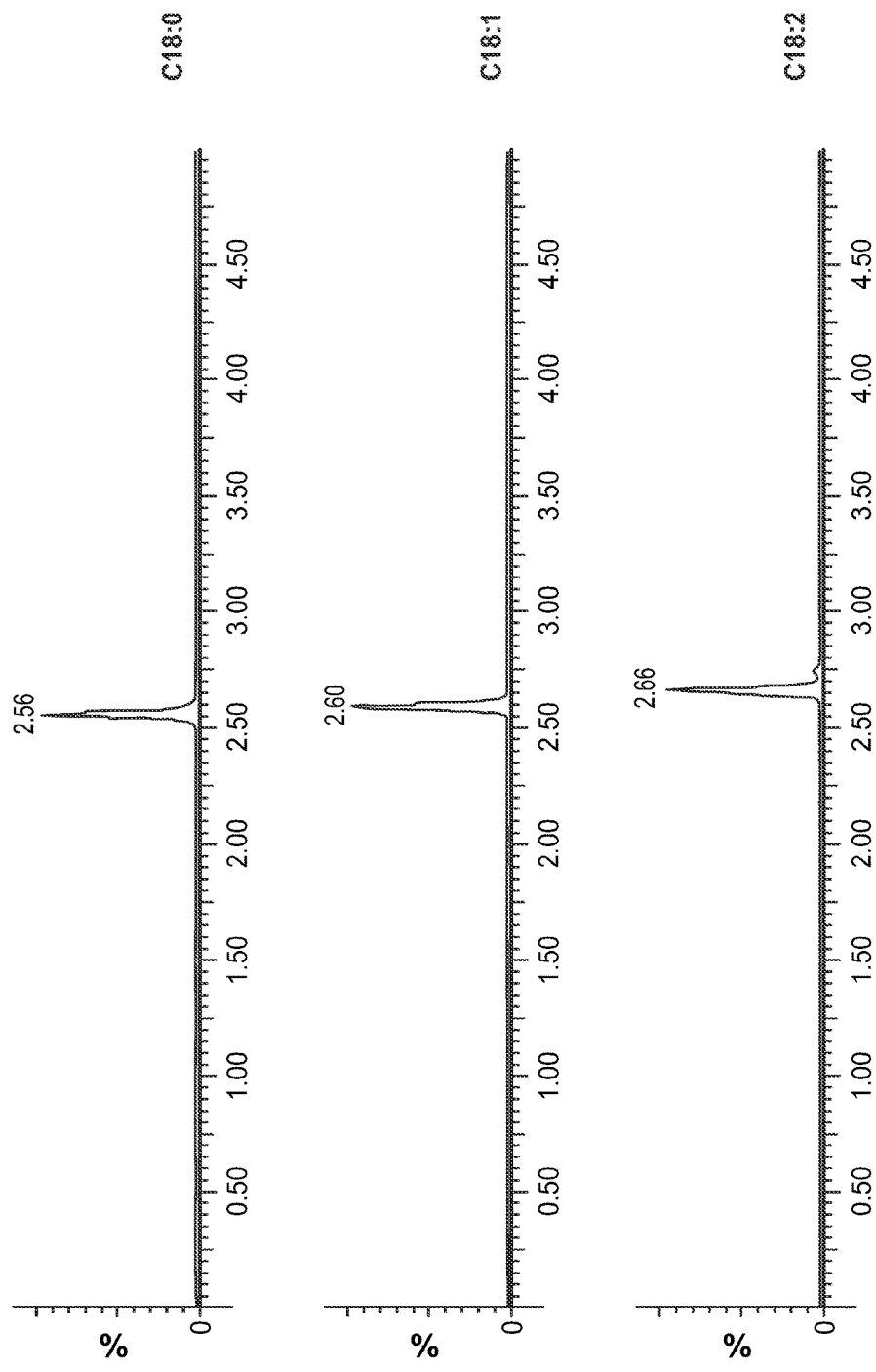
FIG. 20A shows chromatograms of C18:0, C18:1 and C18:2 using a pyridine based stationary phase as described in Examples 3 and 10.
Figure 20B:
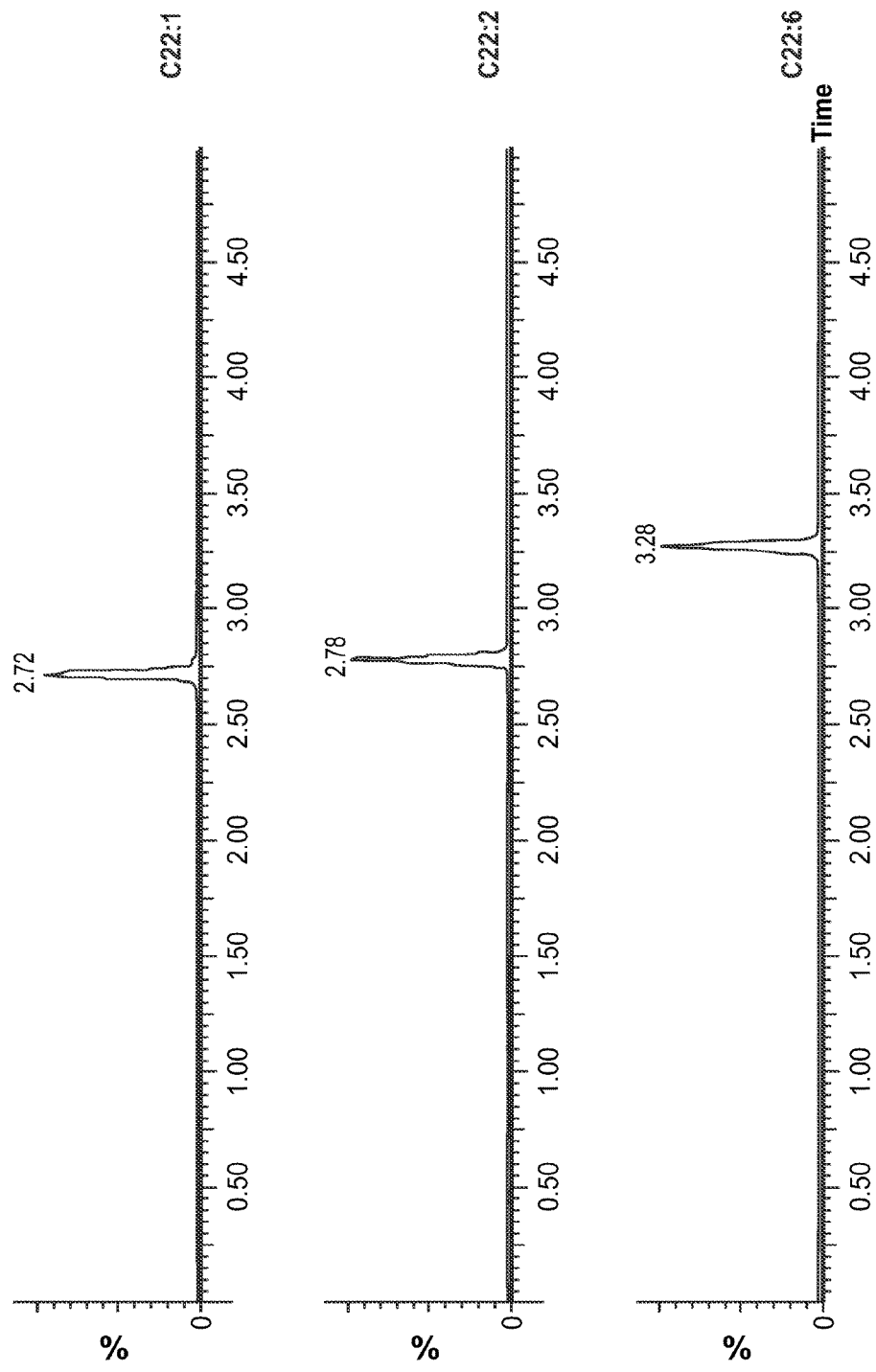
FIG. 20B shows chromatograms of C22:1, C22:2 and C22:6 using a pyridine based stationary phase as described in Examples 3 and 10.
Figure 21A:
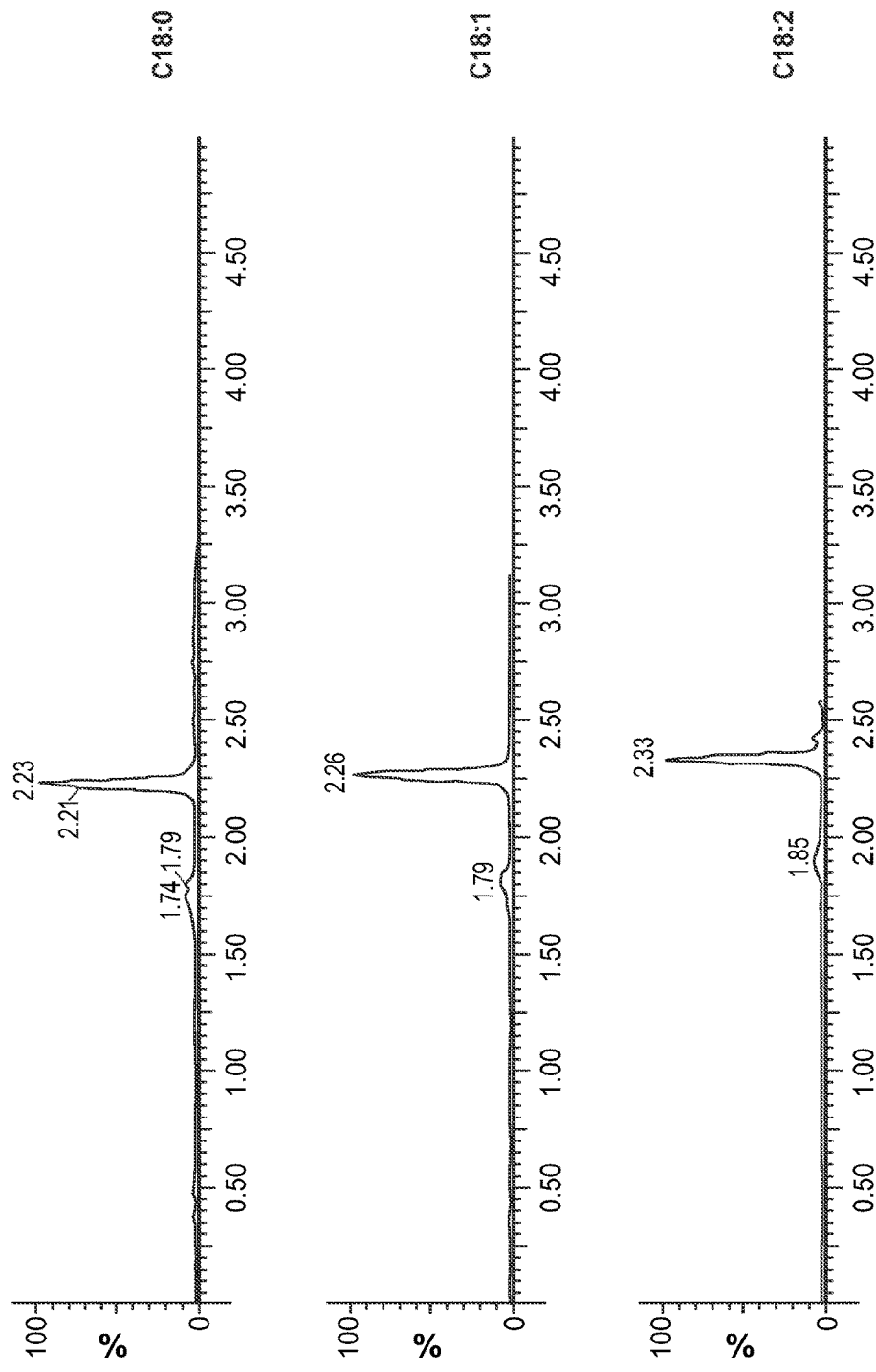
FIG. 21A shows chromatograms of C18:0, C18:1 and C18:2 using a 6-aminoquinoline based stationary phase as described in Examples 3 and 10.
Figure 21B:
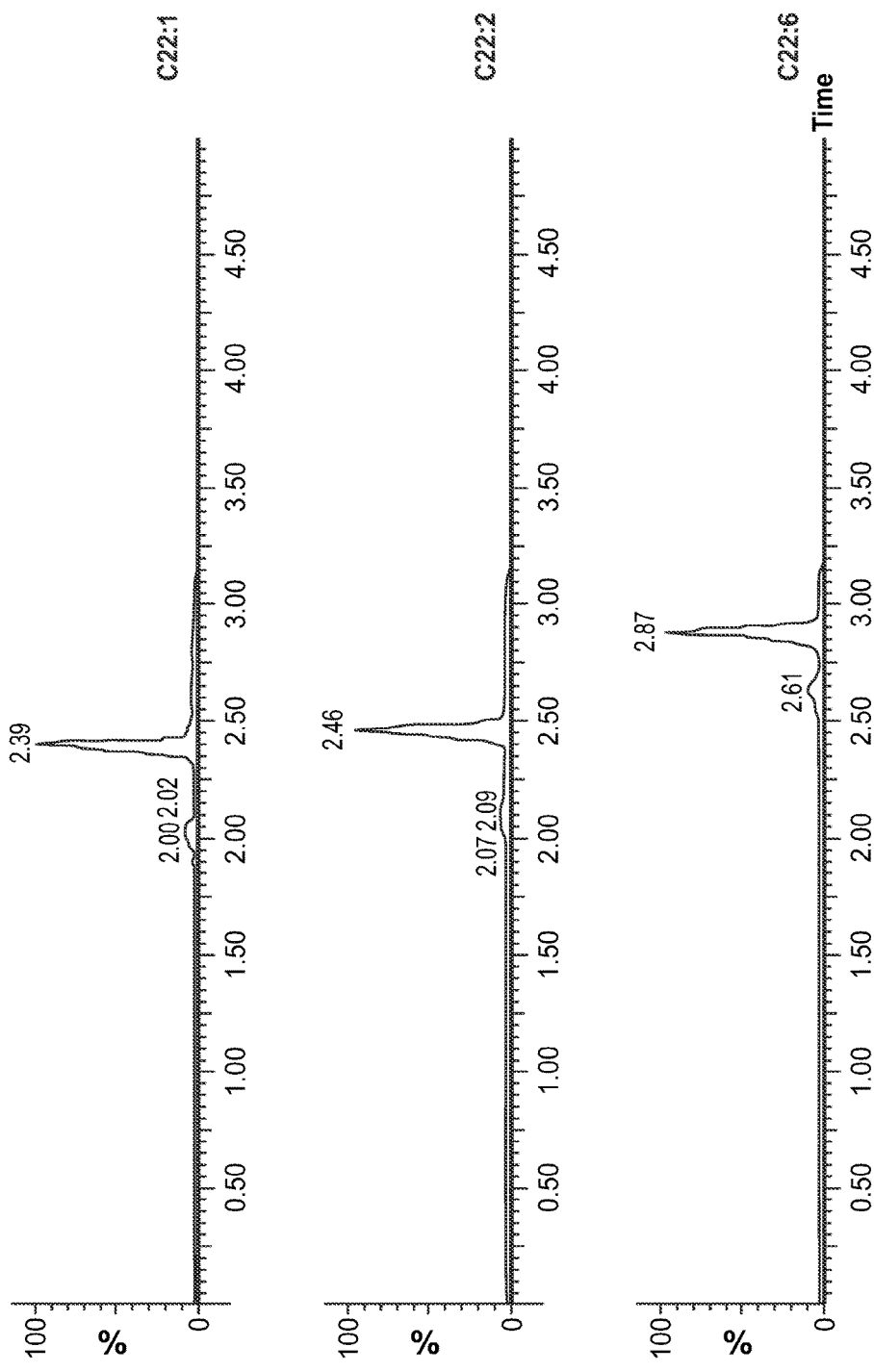
FIG. 21B shows chromatograms of C22:1, C22:2 and C22:6 using a 6-aminoquinoline based stationary phase as described in Examples 3 and 10.
Figure 22A:
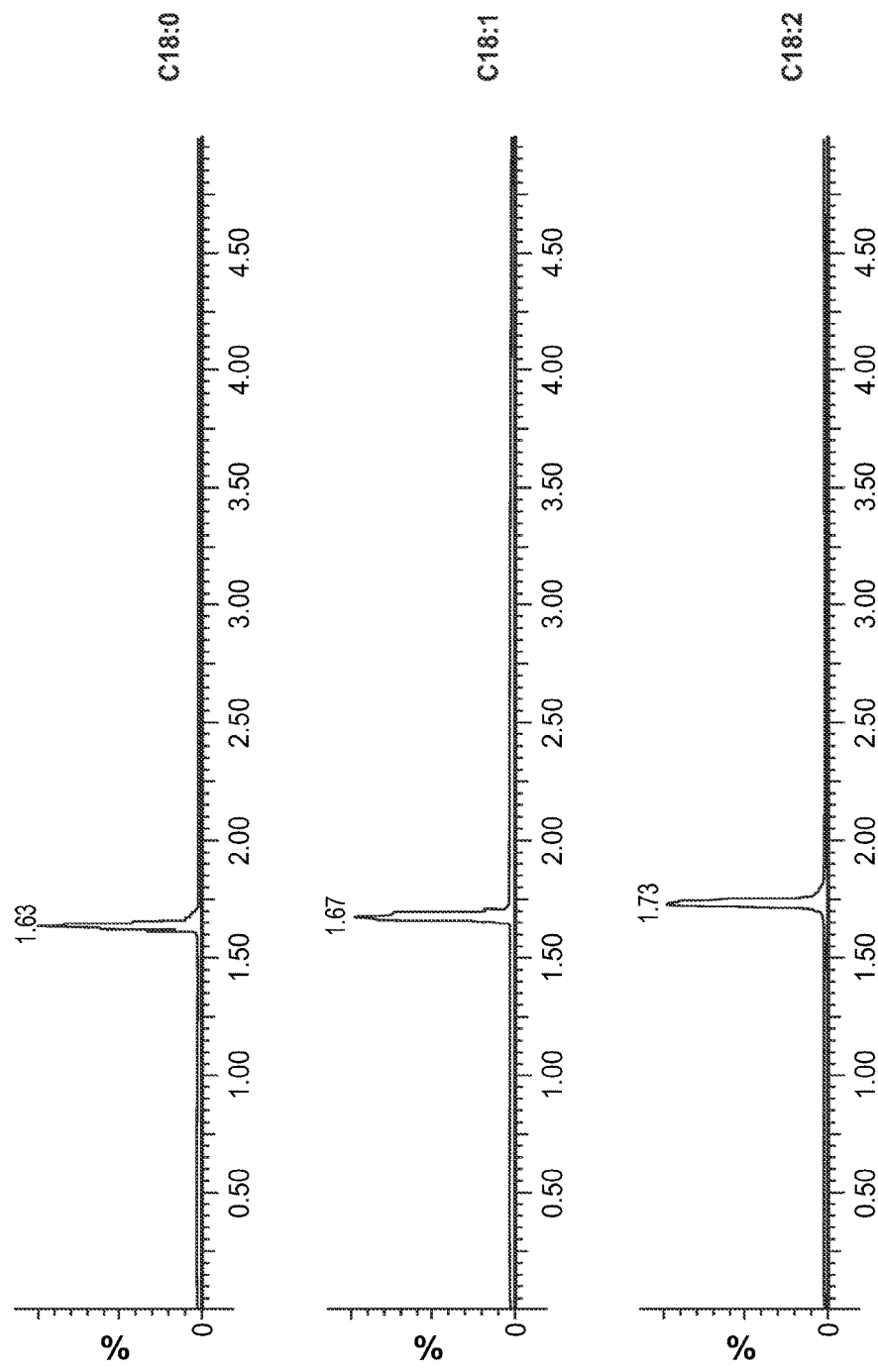
FIG. 22A shows chromatograms of C18:0, C18:1 and C18:2 using a aniline based stationary phase as described in Examples 3 and 10.
Figure 22B:
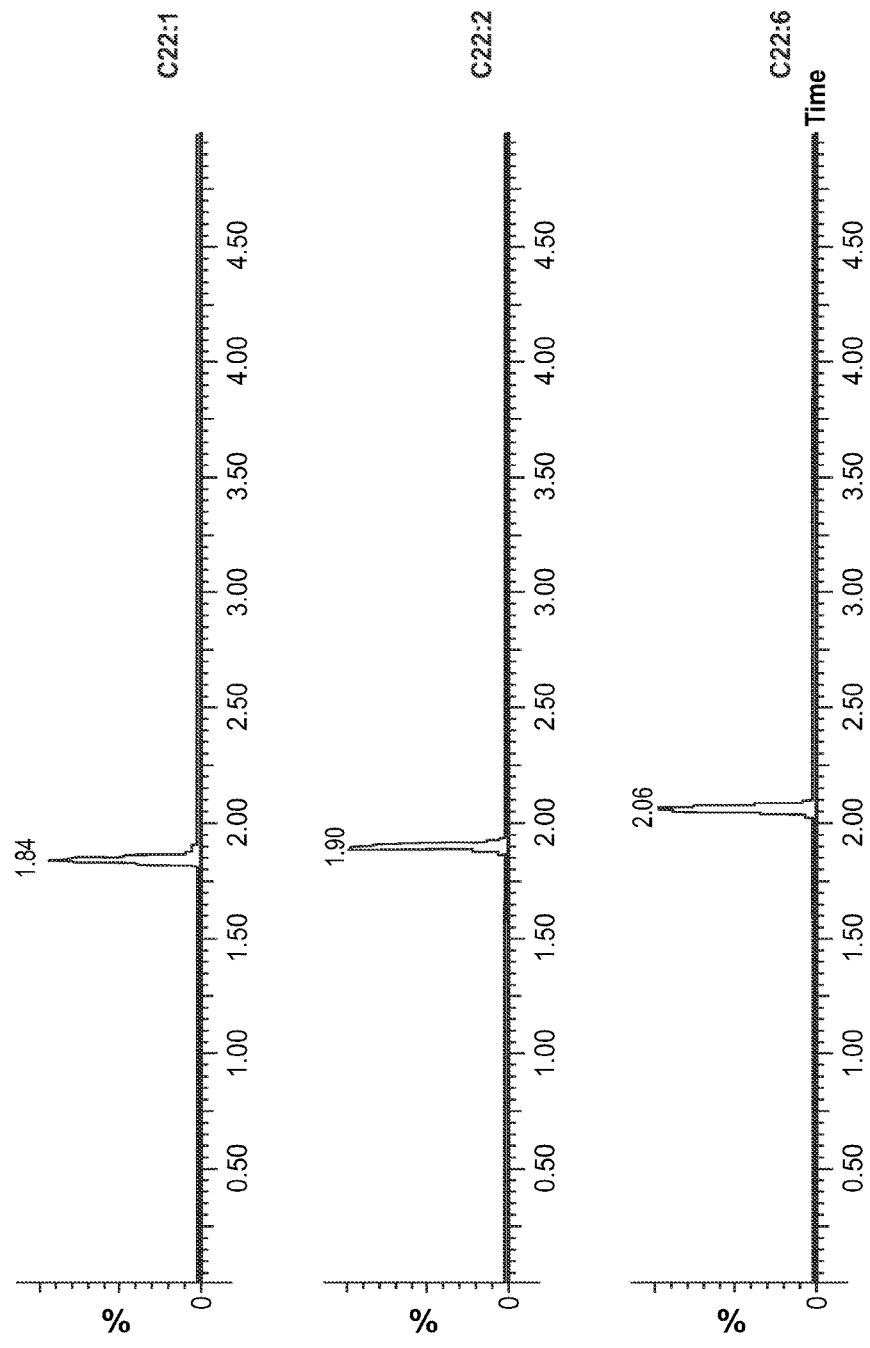
FIG. 22B shows chromatograms of C22:1, C22:2 and C22:6 using a aniline based stationary phase as described in Examples 3 and 10.
Figure 23A:
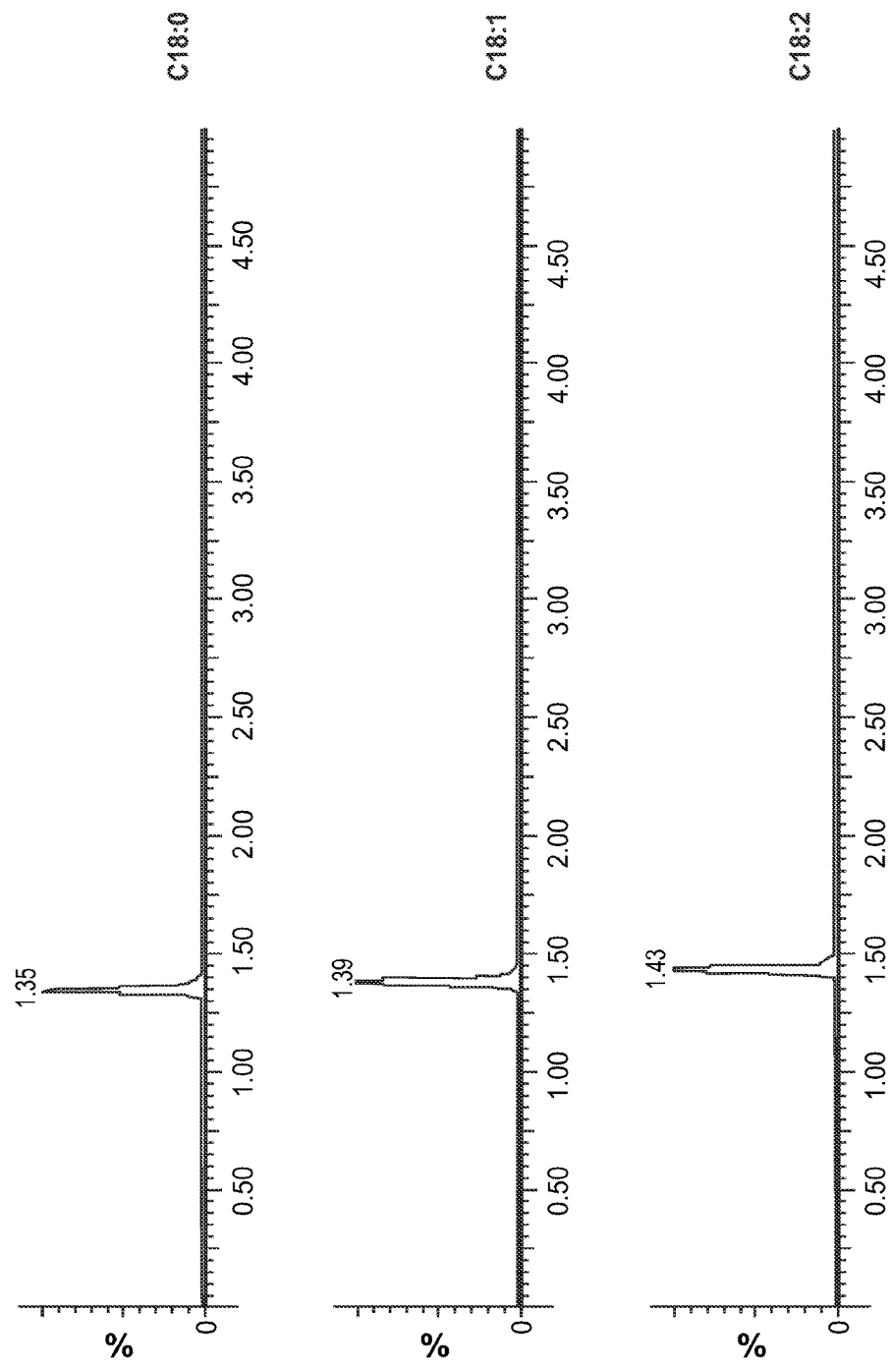
FIG. 23A shows chromatograms of C18:0, C18:1 and C18:2 using a GPTMS based stationary phase as described in Examples 3 and 10.
Figure 23B:
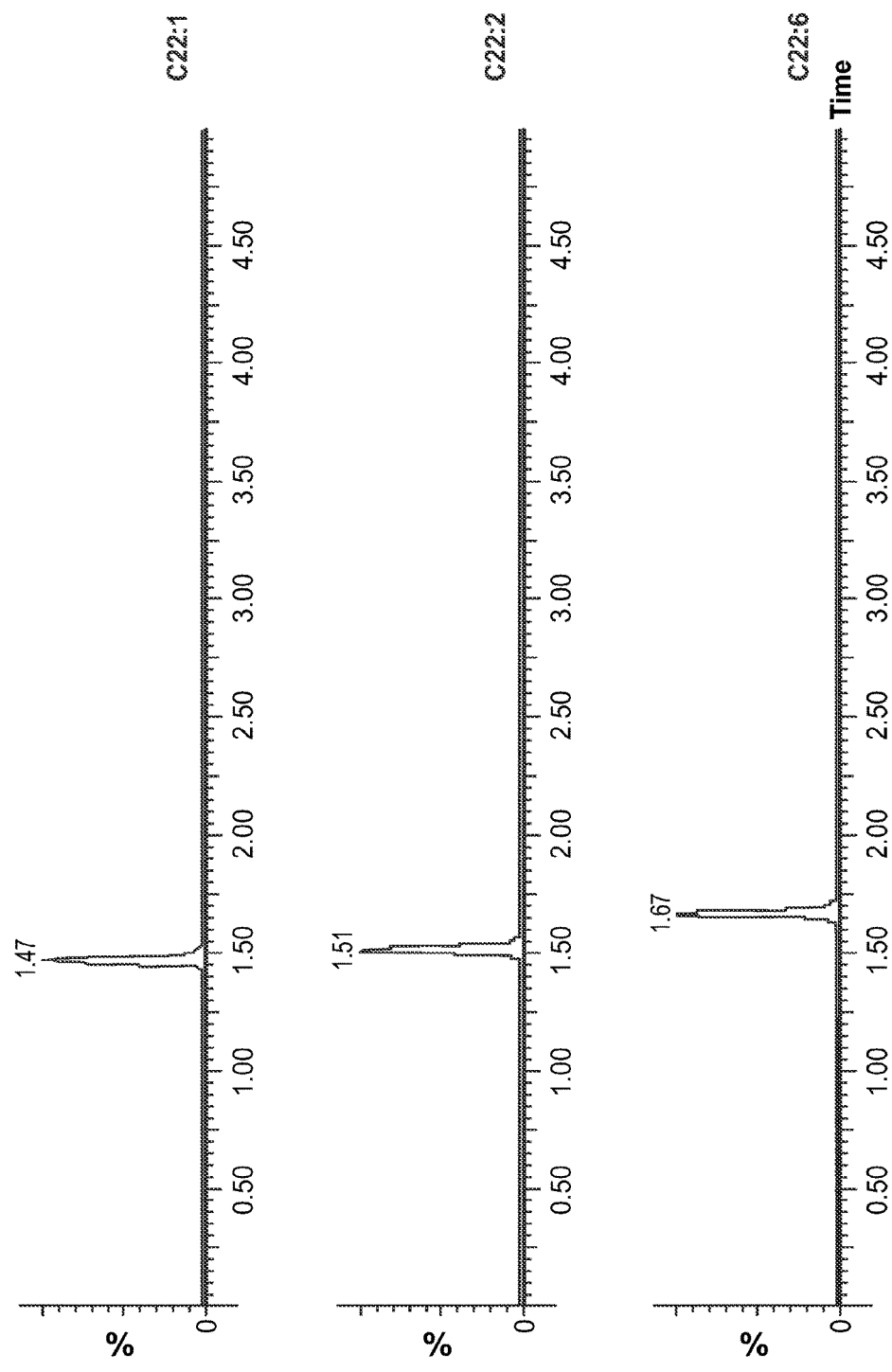
FIG. 23B shows chromatograms of C22:1, C22:2 and C22:6 using a GPTMS based stationary phase as described in Examples 3 and 10.
Figure 24A:
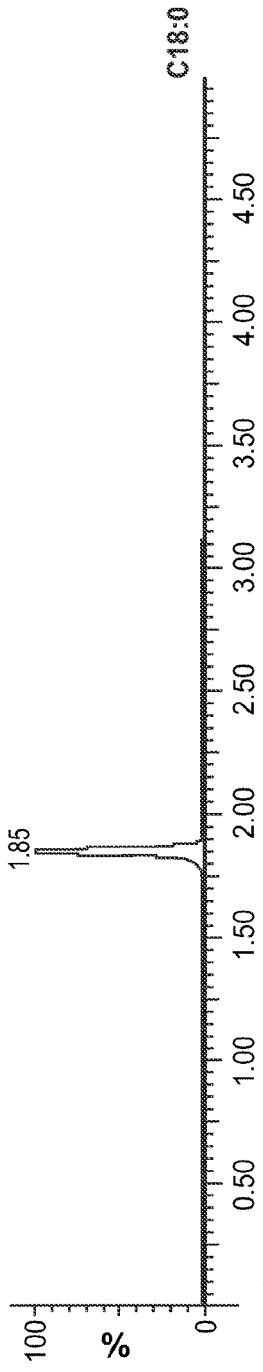
FIGS. 24A-24F show chromatograms of C18:0, C18:1, C18:2, C22:1, C22:2 and C22:6 using a 4-n-octylaniline based stationary phase as described in Examples 3 and 10
Figure 24B:
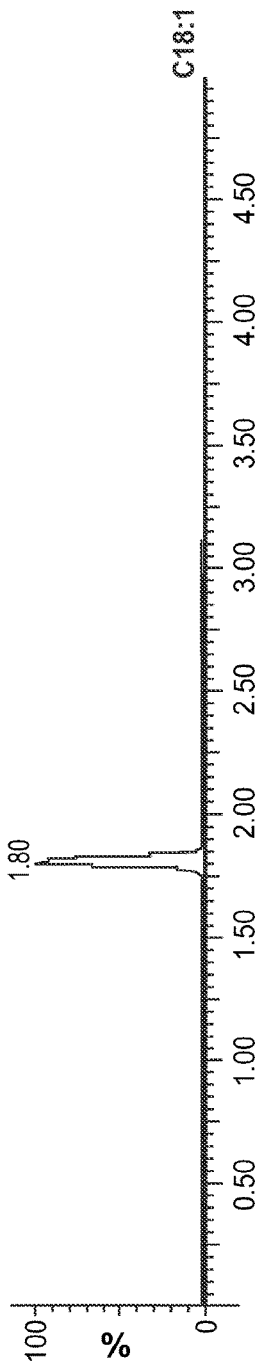
Figure 24C:
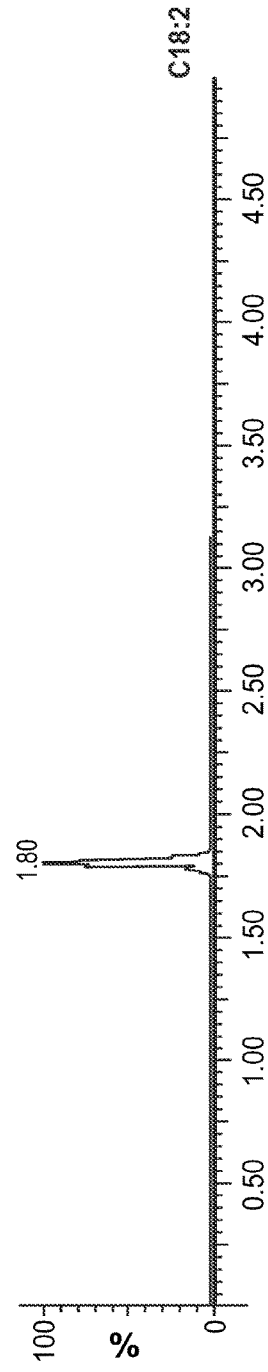
Figure 24D:
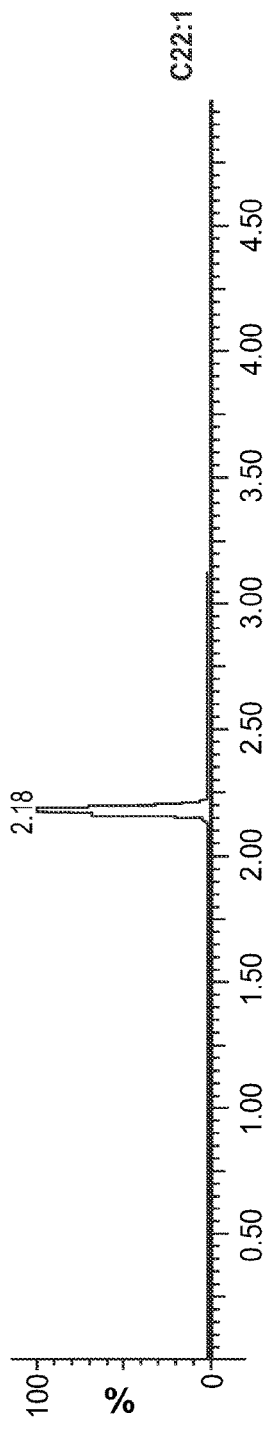
Figure 24E:
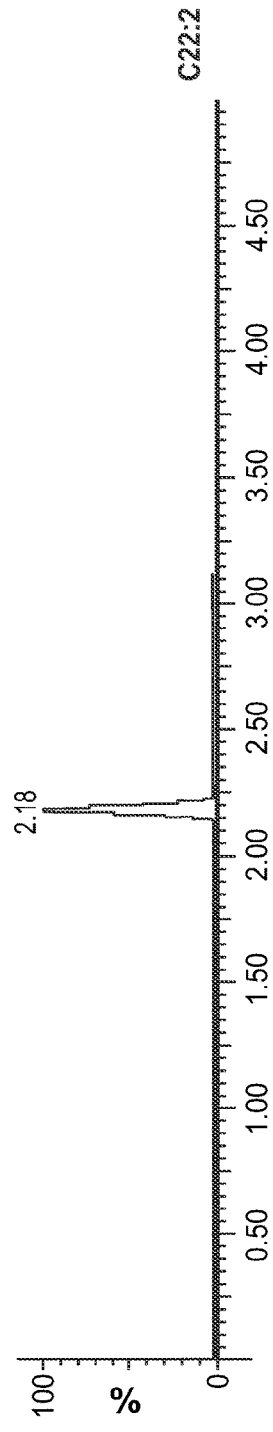
Figure 24F:
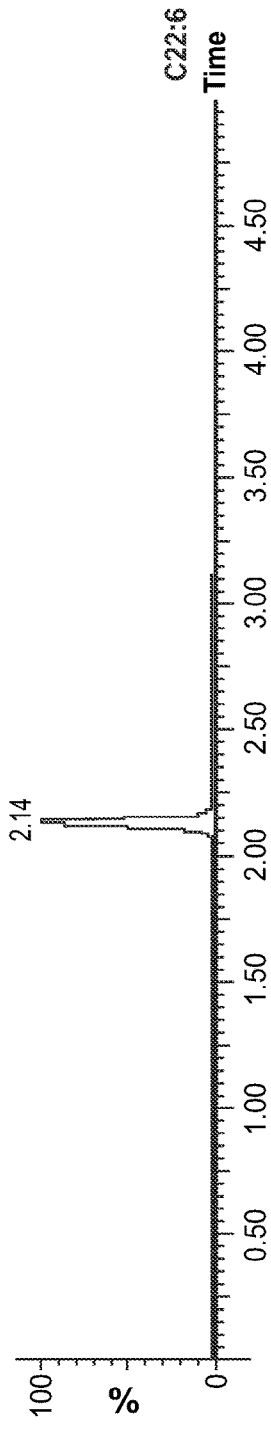

An ACQUITY UPC²® system equipped with: Convergence Chromatography Binary Solvent Manager (ccBSM), Sample Manager (SM), Convergence Chromatography Manager (CCM), Column Manager (CM-A), and Photodiode Array (PDA) was used. The system and separation conditions are provided as follows:

Example 8 GPTMS Bonding on Organic-Inorganic Hybrid Mitigates Retention Drift or Change As shown in FIG. 6, treatment of a bridged ethylene hybrid (BEH) stationary phase with glycidoxypropyltrimethoxysilane (GPTMS) followed by a subsequent epoxide opening reaction to give a diol can significantly mitigate the effects of retention drift. Graph 600 shows a plot of the % Original Retention of unfunctionalized 3 μm BEH particles (605) compared with diol-functionalized 3 μm BEH particles (610). The % original retention is given as a function of time, with days on the x axis. The results indicate that, in at least some preferred embodiments, functionalizaiton of a chromatographic surface with GPTMS and subsequent epoxide opening to give a diol can mitigate retention drift. The results also show that the GPTMS coating alone addresses the issue of retention drift and also provides significant retention.

Example 9 Separation of Compounds of Interest Using 1-Aminoanthracene Based Stationary Phase Using simple chromatographic conditions, the methodology and stationary phases of the present disclosure provides superior separation of compounds of interest, e.g. lipids and fat-soluble Vitamins, compared to current, state-of-the-art methodology. They also deliver different selectivity, as well, which is advantageous for revolving different classes of compounds.

Peak detection and structural determination was also provided using an ACQUITY® SQD2 Mass Spectrometer: 3.46 kV capillary; 25V cone; 350° C. source; 500 L/hr desolvation gas; 10 L/hr cone gas; LM Res 11.8; HM Res 15.1; −0.2 Ion Energy.

First conditions: Flow Rate: Gradient: 3-20% methanol in $CO_2$ in 2 mins; 20% methanol in CO2 for 0.5 mins; 20-3% methanol in $CO_2$ in 0.5 mins. ABPR setting: 2175 psi. Column Temperature: 40° C. Detection: 235 nm compensated 400-500 nm (320 nm compensated 400-500 nm for vitamin A, as needed). Column Dimensions: 3.0×50 mm. Stationary Phase: 1-aminoanthracene modified diol, 2.5 μm as provided in Example 7.

Second conditions: Flow Rate: 2.0 mL/min. Gradient: 3-8% methanol in $CO_2$ in 3 mins (#8 curve); 8-35% methanol in $CO_2$ in 0.5 mins (#1 curve); 35% methanol in $CO_2$ for 1 minute; 35-3% methanol in $CO_2$ in 0.5 mins (#1 curve). ABPR:1800 psi. Column Temperature: 50° C. Sample: GLC85 lipids standard (Nu-chek Prep, Elysian, Minn., USA), 1 g/L in $CHCl_3$ stock diluted 20× with 1:1 heptane:IPA. Column Dimensions: 3.0×50 mm. Stationary Phase: 1-aminoanthracene modified diol, 2.5 μm as provided in Example 7.

These results are surprising because the mixing of a hydrophobic and hydrophilic groups on the same ligand is not only challenging, but an atypical motif for stationary phases. Oftentimes, pi-electron rich ligands are used for very specialized separations and used to give slightly different selectivity from C18 bonded phases. It was found that very different selectivity exists between 1-aminoanthracene based stationary phase and, for example, an ACQUITY UPC$^2$® HSS C18 SB (used for comparison purposes in the present disclosure).

FIGS. 7-16 show lipid separations achieved using the methodology and stationary phases of the present disclosure. The results of these separations show that 1-aminoanthracene coupling is exceptional at retaining and separating fat-soluble vitamins, lipids and metabolites. The 1-aminoanthracene coupling enhances the shape/isomeric selectivity compared to C18 bonded phases.

In the case of fat-soluble vitamins, as their name suggests, these molecules are nonpolar and often have few ionizable groups. In some embodiments, the stationary phase can contain residual amines which may not enhance the separation of nonpolar compounds. In some embodiments, these groups can control the surface pH of the ligand. The presence of these groups would not indicate the separation of fat soluble vitamins is possible. Usually, vitamins, lipid and metabolite separations are performed on C18 bonded phases, such as ACQUITY UPC$^2$® HSS C18 SB. On that material, alkyl chains are the retention selectors resulting in high methylene/hydrophobic selectivity, but little shape/isomeric selectivity. Materials of the present disclosure, such as those containing 1-aminoanthracene, are exceptional at retaining and separating fat-soluble vitamins, lipids and metabolites. These materials also enhance the shape/isomeric selectivity as compared to C18 bonded phases.

Working with lipids resulted in a similar conclusion that the 1-aminoanthracene coupling is superior to ACQUITY UPC$^2$® HSS C18 SB. When using optimized methods, more lipid peaks are resolved on the 1-aminoanthracene coupled prototype. The increased number of peaks observed is related to the selectivity of carbon chain length and degree of saturation of fatty acids. The 1-aminoanthracene prototype addresses a problem noted from "Fast and Simple Free Fatty Acids Analysis Using UPC$^2$/MS" (Library Number: APTNT134753626; Part Number 720004763en) which states that "Reversed-phase chromatography separates lipids according to both chain-length and degree of unsaturation. The problem lies in the fact that the dual nature of the reversed-phase separation process (a double bond in the fatty acyl chain reduces the retention time and the fatty acyl chain length increases the retention time) can hamper the analysis of real samples; the number of components is often so great that identification becomes difficult due to coelution." The stationary phase of the present disclosure results in more retention for unsaturated fatty acid chains (more double bonds yield longer retention times) and longer chain lengths. The separation is based on the number of carbon atoms and the number of double bonds to increase the retention, an exceptional improvement compared to alkyl bonded stationary phases.

Those skilled in the art will understand that the present disclosure can be used to develop and tune methods in other application areas of: fine chemicals/materials (OLEDs, agrochemicals, dyes/organic dyes, conformational polymers, polymer additives and surfactants), food and environmental (pesticides, glycerides, edible oils, tobacco, food adulteration), pharmaceutical/life sciences (lipid profiling, natural products, DMPK/bioanalysis, impurity profiling, medicinal chemistry) and forensics/research (opiates, drugs of abuse, steroids, fatty acids, anit-depressants, gun powder components, explosives).

In addition, these materials and methods could be used as part of a multidimensional experiment (2D-SFC, SFC-LC, etc). Other materials to combine these with include Argentation (silver impregnated materials) and existing lipid methods, such as those on CSH brand columns.

Example 10 Separation of Compounds of Interest Using Various Stationary Phases of the Present Disclosure Additional chromatographic materials were prepared according to the prior Examples using different selectors. Lipid analysis was performed on these additional stationary phases. The materials tested include stationary phases using the following selectors: 1-Aminoanthracene, 2-Picolylamine, Pyridine, 6-aminoquinoline, Aniline, Diol, and 4-n-octylaniline.

The general chromatographic conditions are provided as follows: Sample: GLC85 lipids (Nu-chek Prep), 1 g/L in CHCl$_3$; diluted 20× with 1:1 IPA:Heptane. System: UPC2 w/SQD2, ESI-ionization. Mobile phase: 97.5/2.5 MeOH/H2O w/0.1M NH3 make-up flow. 3.0×50 mm columns. The sample contained a mixture of C$_4$-C$_{24}$ lipids (m/z: 87; 115.1; 143.1; 171.1; 185.1; 199.2; 213.2; 227.2; 241.2; 255.2; 269.2; 283.3; 311.3; 339.3; 225.2; 239.2; 253.2; 267.2; 277.2; 279.2; 281.2; 303.2; 305.2; 307.3; 309.3; 327.2; 335.3; 337.3; 365.3).

FIGS. 17-24 show the lipid separations, both profiles and per individual lipid based on carbon bond number, using these stationary phases. In general, stationary phases containing 1-Aminoanthracene and 4-n-octylaniline show sufficient resolution of the mixture, as well as, an increase in retention based on the number of double bonds. Stationary phases using 2-picolylamine, pyridine, 6-aminoquinoline and aniline couplings and diol are unable to resolve most lipid peaks in sample. Table 9 provides a summary the performance of these stationary phases.

TABLE 9

Performance of the various Stationary Phases of the present disclosure

| Material | Ret. Window (87 to 365.3) | Peak Capacity | t$_R$ (min) C18:0 | C18:1 | C22:1 | C22:6 | Range C18 | C22 | Total DB |
|---|---|---|---|---|---|---|---|---|---|
| 3G | 1.042 | 21.4 | 1.63 | 1.67 | 1.84 | 2.06 | 0.1 | 0.22 | 0.43 |
| 3M | 0.657 | 11.3 | 2.56 | 2.6 | 2.72 | 3.28 | 0.1 | 0.56 | 0.72 |
| 2F | 0.622 | 11.3 | 1.35 | 1.39 | 1.47 | 1.67 | 0.08 | 0.2 | 0.32 |
| 3A | 2.354 | 23.7 | 1.94 | 1.96 | 2.65 | 2.97 | 0.11 | 0.32 | 1.03 |
| 3E | 1.674 | 29.6 | 1.85 | 1.8 | 2.18 | 2.14 | −0.05 | −0.04 | 0.38 |
| 3F | 0.731 | 9.5 | 2.23 | 2.26 | 2.39 | 2.87 | 0.1 | 0.48 | 0.64 |
| 3L | 0.737 | 12.5 | 2.01 | 2.06 | 2.18 | 2.6 | 0.11 | 0.42 | 0.59 |
| HSSC18SB | 1.176 | 24.5 | 1.29 | 1.23 | 1.51 | 1.28 | −0.11 | −0.23 | 0.33 |

Table 9 provides a summary of the results. The retention window is measured as the time difference between the first and last eluting peak of the lipids mixture. It is desirable to maximize this value as it represents the separation space. Material 3A provides the highest retention window value, 200% larger than that of HSS C18 SB (comparable). The peak capacity is measured as the retention window divided by the average peak width of all the peaks eluted in the retention window. Material 3E provides a significant improvement over HSS C18 SB with a 20% greater peak capacity. The retention values for C18:0, C18:1, C22:1 and C22:6 represent retention times of lipids with carbon chain lengths of 18 and 22, respectively, and 0, 1 and 6 double bonds in the chains, respectively. Materials 3E and HSS C18 SB show decreasing retention as the number of double bonds increases, while all others show increasing retention. The (retention) range of all C18 and C22 lipids in the mixture are calculated by subtracting retention time of the lipid having the highest level of unsaturation (most double bonds), C18 or C22, respectively, from the retention time of the saturated lipid C18 or C22, respectively. A negative value in either of these columns represents a decrease in retention based on the number of double bonds present in the chain. The positive C18 and C22 range values for materials in this list represent a unique selectivity for compared to HSS C18 SB. The total double bond (DB) range is the total range of C18 and C22 lipid species, calculated from the absolute value of the sum of the C18 and C22 ranges. It is desirable to maximize this value, which is noted for material 3A. In some embodiments, the materials of the present disclosure provide a DB value of greater than 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4 or 1.5 under normal or routine chromatographic conditions.

It is observed that the best peak capacities are provided by N-octyl-aniline, HSS C18 SB (comparative column), 1-aminoanthracene and aniline based stationary phases. Peak capacity is the retention window divided by the average peak width at 13.4% (4 sigma width). The best C18 and C22 ranges are provided by pyridine, 6-aminoquinoline, 2-picolylamine and 1-aminoanthracene. The C18 range is the time difference between C18:2 and C18:0. A negative number indicates that C18:2 eluted before C18:0. Same for C22 range. And, the best total double bond ranges are provided by 1-aminoanthracene, pyridine, 6-aminoquinoline and 2-picolylamine. C18:0 has 18 carbons and 0 double bonds; C18:1 has 18 carbons and 1 double bond; etc. Total DB (double bond) range is the difference between the maximum and minimum retention times of the C18 and C22 series.

Example 11 Separation of Vitamins D and K Using Various Stationary Phases of the Present Disclosure Two critical pairs, Vitamins K1 and K2 and Vitamins D2 and D3, were tested using the stationary phases of the present disclosure to determine if these materials improve the resolution of these pairs. The chromatographic conditions are provided in Table 10. Table 11 provides a summary the results. For each of the materials tested, the resolutions of two critical pairs, Vitamins K1 and K2 and Vitamins D2 and D3, respectively, were measured. Materials 3J, 3H and 3P significantly improve the resolution of the critical pairs, particularly for Vitamins K1 and K2, compared to HSS C18 SB (comparison). The percent improvement is calculated as follows:

$$\% \text{ improvement} = \frac{Rs_{prototype} - Rs_{HSS\ C18\ SB}}{Rs_{HSS\ C18\ SB}} \times 100$$

It is expected that a smaller particle size of materials 3J, 3H and 3P would further increase the resolution of the critical pairs. For example, it is expected that reducing the particle size of material 3P would increase the observed resolution by and additional 44%. It is believed that the conjugated moieties of materials 3J, 3H and 3P increase the interactions between the chromatographic surface and the vitamins driving a unique selectivity, compared to HSS C18 SB.

In some embodiments, the materials of the present disclosure provide an Rs value for Vitamins D3/D4 greater than 1.0, 1.5, 2.0, 2.5, 3.0, 3.5, 4.0 or 4.5 under normal or routine chromatographic conditions. In some embodiments, the materials of the present disclosure provide an Rs value for Vitamins K1/K2 greater than 1.0, 1.5, 2.0, 2.5, 3.0, 3.5, 4.0 or 4.5 under normal or routine chromatographic conditions.

TABLE 10

Chromatographic Conditions

| | |
|---|---|
| Co-Solvent | Methanol |
| Gradient | 3-20% co-solvent in 2 minutes |
| Samples | Vitamins: A, A acetate, E, E acetate, K1, K2, D2, D3 (0.2 mg/mL each) |
| Column Dimension | 3.0 × 50 mm |
| Flow Rate | 1.2 mL/min |
| Column Temperature | 40° C. |
| Back Pressure | 2175 psi |
| Detector | ACQUITY ® PDA with SFC Flow Cell |
| Detector Setting | 235 nm 40 spec/sec (320 nm for vit. A) |
| Weak Needle Wash | iso-propanol |
| Injection | 0.5 µL (2.0 µL loop with PLUNO injection mode) |
| Instrument | UPC$^2$ ® |
| Software | Empower |

TABLE 11

Performance of the various Stationary Phases of the present disclosure on the separation of Vitamins D and K

| Material | Vitamin k Rs | Vitamin D Rs | % improvement Vit D Rs (compared to HSS C18 SB) |
|---|---|---|---|
| HSS C18SB | 0.23 | 0.74 | 0 |
| 2F | 2.09 | 0.26 | −64 |
| 3L | 3.40 | 0.46 | −38 |
| 3O | 2.20 | 0.22 | −71 |
| 3N | 0.30 | 0.32 | −57 |
| 3F | 2.77 | 0.43 | −42 |
| 3I | 3.86 | 0.67 | −9 |
| 3G | 3.54 | 0.54 | −27 |
| 3M | 2.65 | / | / |
| 3E | 2.01 | 0.00 | −100 |
| 3J | 3.49 | 0.86 | 16 |
| 3H | 3.97 | 0.79 | 7 |
| 3P | 3.81 | 0.99 | 34 |

Unless indicated otherwise, all techniques, including the use of kits and reagents, can be carried out according to the manufacturers' information, methods known in the art.

Recitation of ranges of values herein is merely intended to serve as a shorthand method of referring individually to each separate value falling within the range. Unless otherwise indicated, each individual value is incorporated into the specification as if it were individually recited. Each of the documents cited herein (including all patents, patent applications, scientific publications, manufacturer's specifications, and instructions), are hereby incorporated by reference in their entirety.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration and not limitation.

The invention claimed is:

1. A method of separating a compound of interest from a mixture, the method comprising:
   (a) providing the mixture containing the compound of interest;
   (b) introducing a portion of the mixture to a chromatographic system having a chromatographic column; and
   (c) eluting the separated compound of interest from the chromatographic column;
wherein the chromatographic column has a stationary phase comprising

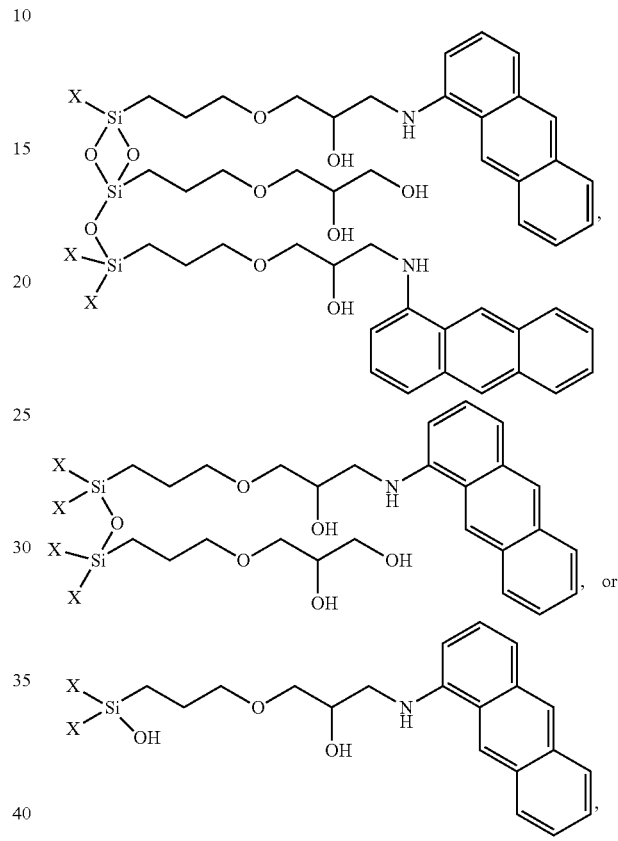

or a mixture thereof;
   wherein X is a chromatographic substrate containing silica, metal oxide, an inorganic-organic hybrid material, a group of block copolymers, or a combination thereof.

2. The method of claim 1, wherein the compound of interest is a lipid, vitamin, or polycyclic aromatic hydrocarbon.

3. The method of claim 2, wherein the lipid is a saturated or an unsaturated fatty acid, monoacylglyceride, diacylglyceride, triacylglyceride, phospholipid, sphingolipid or steroid.

4. The method of claim 2, wherein the vitamin is a water soluble vitamin selected from the group consisting of vitamin C, vitamin B, or derivatives or combinations thereof.

5. The method of claim 2, wherein the vitamin is a fat soluble vitamin selected from the group consisting of vitamin A, vitamin D, vitamin K, vitamin E, betacarotene, or derivatives or combinations thereof.

6. The method of claim 1, wherein the chromatographic stationary phase is adapted for supercritical fluid chromatography.

7. The method of claim 1, wherein the chromatographic stationary phase is adapted for carbon dioxide based chromatography.

8. A method for mitigating or preventing retention drift in normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography comprising:
    chromatographically separating the mixture using the chromatographic system comprising the stationary phase according to claim 1, thereby mitigating or preventing retention drift.

* * * * *